(12) United States Patent
Geigle et al.

(10) Patent No.: US 8,790,705 B2
(45) Date of Patent: *Jul. 29, 2014

(54) SPHERICAL MICROCAPSULES COMPRISING GLP-1 PEPTIDES, THEIR PRODUCTION AND USE

(75) Inventors: Peter Geigle, Alzenau (DE); Christine Wallrapp, Grossostheim (DE); Eric Thoenes, Budingen (DE); Frank Thurmer, Alzenau (DE)

(73) Assignee: BioCompatibles UK Ltd., Farnham, Surrey (GB)

( * ) Notice: Subject to any disclaimer, the term of this patent is extended or adjusted under 35 U.S.C. 154(b) by 645 days.

This patent is subject to a terminal disclaimer.

(21) Appl. No.: 12/300,087

(22) PCT Filed: Apr. 27, 2007

(86) PCT No.: PCT/EP2007/003775

§ 371 (c)(1),
(2), (4) Date: Nov. 16, 2009

(87) PCT Pub. No.: WO2007/128443

PCT Pub. Date: Nov. 15, 2007

(65) Prior Publication Data

US 2010/0068289 A1 Mar. 18, 2010

(30) Foreign Application Priority Data

May 10, 2006 (EP) .................................... 06009678

(51) Int. Cl.
| | | |
|---|---|---|
| *C22C 9/10* | (2006.01) | |
| *C22C 9/05* | (2006.01) | |
| *C22C 38/16* | (2006.01) | |
| *A61K 38/00* | (2006.01) | |
| *A61K 38/28* | (2006.01) | |

(52) U.S. Cl.
USPC ........... 424/490; 424/493; 424/93.7; 514/1.1; 514/6.9

(58) Field of Classification Search
None
See application file for complete search history.

(56) References Cited

U.S. PATENT DOCUMENTS

| | | | | |
|---|---|---|---|---|
| 4,352,883 | A * | 10/1982 | Lim ............................... | 435/178 |
| 5,861,284 | A | 1/1999 | Nishimura et al. | |
| 6,267,954 | B1 | 7/2001 | Abitbol et al. | |
| 6,849,708 | B1 | 2/2005 | Habener | |
| 6,858,576 | B1 | 2/2005 | Young et al. | |
| 2003/0144206 | A1 | 7/2003 | Knudsen et al. | |
| 2003/0195154 | A1 | 10/2003 | Walker et al. | |
| 2003/0221201 | A1 | 11/2003 | Prior et al. | |
| 2004/0143104 | A1 | 7/2004 | Wadsworth et al. | |
| 2004/0146985 | A1 | 7/2004 | Sun et al. | |
| 2006/0030528 | A1 | 2/2006 | Hathaway et al. | |
| 2006/0084604 | A1 | 4/2006 | Kitaura et al. | |
| 2007/0050855 | A1 | 3/2007 | Prior et al. | |
| 2010/0068289 | A1 | 3/2010 | Geigle et al. | |
| 2010/0160556 | A1 | 6/2010 | Wallrapp et al. | |
| 2010/0256332 | A1 | 10/2010 | Wallrapp et al. | |
| 2011/0130329 | A1 | 6/2011 | Geigle et al. | |

FOREIGN PATENT DOCUMENTS

| | | |
|---|---|---|
| EP | 0891378 | 1/1999 |
| EP | 0941114 | 9/1999 |
| EP | 1454629 | 9/2004 |
| EP | 1529534 | 5/2005 |
| EP | 1767545 | 3/2007 |
| EP | 1854455 | 11/2007 |
| EP | 2163243 | 3/2010 |
| WO | WO94/28141 | 12/1994 |
| WO | WO97/31943 | 9/1997 |
| WO | WO 9808871 | 3/1998 |
| WO | WO98/20895 | 5/1998 |
| WO | WO 99/35255 | 7/1999 |
| WO | WO 9946283 | 9/1999 |
| WO | WO 99/53064 | 10/1999 |
| WO | WO01/66135 | 9/2001 |
| WO | WO 0246227 | 6/2002 |
| WO | WO02/067971 | 9/2002 |
| WO | WO 03/002136 | 1/2003 |
| WO | WO 03/010305 | 2/2003 |
| WO | WO 03011892 | 2/2003 |
| WO | WO 03020201 | 3/2003 |
| WO | WO 03058203 | 7/2003 |
| WO | WO 03/086444 | 10/2003 |
| WO | WO 2004/022004 | 3/2004 |

(Continued)

OTHER PUBLICATIONS

Drucker, 1988, Journal of Biological Chemistry, vol. 263, No. 27, pp. 13475-13478.*

(Continued)

*Primary Examiner* — Christine J Saoud
*Assistant Examiner* — Jegatheesan Seharaseyon
(74) *Attorney, Agent, or Firm* — Heslin Rothenberg Farley & Mesiti P.C.

(57) ABSTRACT

The present invention provides spherical microcapsules comprising at least one surface coating and a core, wherein the at least one surface coating comprises cross-linked polymers, and wherein the core comprises cross-linked polymers and cells capable of expressing and secreting a GLP-1 peptide, a fragment or variant thereof or a fusion peptide comprising GLP-1 or a fragment or variant thereof. The present application is furthermore directed to methods for production of these spherical microcapsules and to the use of these microcapsules e.g. in the treatment of type 2 diabetes, weight disorders and diseases or conditions associated thereto, neurodegenerative disorders and diseases or conditions associated thereto, or for the treatment of disorders and diseases or conditions associated to apoptosis.

11 Claims, 20 Drawing Sheets

(56) References Cited

FOREIGN PATENT DOCUMENTS

| WO | WO2005/014049 | 2/2005 |
|---|---|---|
| WO | WO2005/035553 | 4/2005 |
| WO | WO 2005058958 | 6/2005 |
| WO | WO 2005077072 | 8/2005 |
| WO | WO 2005097175 | 10/2005 |
| WO | WO 2006010143 | 1/2006 |
| WO | WO 2006044063 | 4/2006 |
| WO | WO 2007018619 | 2/2007 |
| WO | WO 2007039140 | 4/2007 |
| WO | WO2007/128443 | 11/2007 |

OTHER PUBLICATIONS

Sungwon, K., et al.: "Long-term insulinotropic activity of glucagon-like peptide-1/polymer conjugate on islet microcapsules", Tissue Engineering, vol. 10(11-12), pp. 1607-1616, 2004.

Kim, S., et al.: "Synthesis, bioactivity and specificity of glucagon-like peptide-1 (7-37) polymer conjugate to isolated rat islets", Biomaterials, Elsevier Science Publishers BV, vol. 26(17), p. 3600, 2005.

Kim, S., et al.: "Insulinotropic activity of sulfonylurea/pullulan conjugate in rate islet microcapsule", Biomaterials, Elsevier Science Publishers BV, vol. 24(26), pp. 4843-4851, 2003.

Jork, A., et al.: "Biocompatible alginate from freshly collected laminaria pallida for implantation", Applied Microbiology and Biotechnology, vol. 53(2), pp. 224-229, 2000.

Winn, S. R., et al.: "Managing chronic pain with encapsulated cell implants releasing catecholamines and endogenous opiods", Frontiers in Bioscience, vol. 10, pp. 367-368, 2005.

Zimmerman, H., et al.: "Towards a medically approved technology for alginate-based microcapsules allowing long-term immunoisolated transplantation", Journal of Materials Science: Materials in Medicine, vol. 16(6), pp. 492-501, 2005.

Chae, S. Y., et al "Bioactive polymers for biohybrid artificial pancreas", Journal of Drug Targeting, vol. 9(6), pp. 473-484, 2001.

Brinker, T.: Tennis: Tissue Engineering von Neuro-Implantation zur Schmerztherapie; Teilprojekt 1: In vivo Modelle fur gekapselte Zellen und in-vivo Validierungi:, [Online], pp. 1-137, 2006.

Malpique, et al.: "118. Cryopreservation of neuroblastoma N2a cells in an alginate environment: strategies to improve cell recovery and neuronal differentiation after thawing", Cryobiology, vol. 55(3), pp. 363-364. 2007.

Kieffer, T.J. et al., "The Glucagon-Like Peptides", Endocrine Reviews, Baltimore, Md., vol. 20(6), pp. 876-913, 1999.

Drucker, D.J., "Glucagon-Like Peptides: Regulators of Cell Proliferation, Differentiation, and Apoptosis", Molecular Endocrinology, vol. 17(2), pp. 161-171, 2003.

Perry, T.A. et al., "Enhancing Central Nervous System Endogenous GLP-I Receptor Pathways for Intervention in Alzheimer's Disease", Current Alzheimer Research, vol. 2(3), pp. 377-385, 2005.

International Search Report and Written Opinion issued on Jan. 25, 2007 in International Application No. PCT/EP2006/009226.

International Search Report and Written Opinion issued on Nov. 17, 2008 in International Application No. PCT/EP2008/002414.

Busby et al., "Proglucagon (Fragment)", Uniprot, Q6RYB1, May 7, 2004.

Chen et al., "Glucagon precursor [contains: Glicentin-related polypeptide (GRPP); Glucagon; Glucagon-like peptide 1 (GLP-1); Glucagon-like peptide 1(7-37) (GLP-1(7-37)); Glucagon-like peptide (7-36) (GLP-1(7-36)); Glucagon-like peptide 2(GLP-2)]", Uniprot, 012956, Jul. 1, 2007.

International Preliminary Report on Patentability issued on Oct. 8, 2009 in International Application No. PCT/EP2008/002414.

International Preliminary Report on Patentability issued on Jul. 24, 2008 in International Application No. PCT/EP2008/002278.

Office Action in related co-pending U.S. Appl. No. 12/531,411 mailed Dec. 20, 2011.

Drucker, et al.: Journal of Biological Chemistry, vol. 263(27) pp. 13475-13478, 1986.

Kim, S., et al.: "Insulinotropic Activity of Sulfonylurea/Pullulan Conjugate in Rat Islet Microcapsule," Biomaterials, vol. 24(26), pp. 4643-4651, 2003.

Heile, Anna, et al.: "Clinical Translation of Stem Cell Therapy in Traumatic Brain Injury: the Potential of Encapsulated Mesenchymal Cell Biodelivery of Glucagon-Like Peptide-1," Dialogues in Clinical Neuroscience, vol. 13(3), 2011, pp. 279-286.

Kolchanov, N. A., et al.: "Single Amino Acid Substitutions Producing Instability of Globular Proteins Calculation of Their Frequencies in the Entire Mutational Spectra of the $\alpha$- and $\beta$-Subunits of Human Hemoglobin," Journal of Molecular Evolution, vol. 27, 1988, pp. 154-162.

Pasquo, Alessandra, et al.: "Structural Stability of Human Protein Tyrosine Phosphatase $\rho$ Catalytic Domain: Effect of Point Mutations," PLOS ONE, 2012, vol. 7, Issue 2, e32555.

Zhang, Wujie, et al.: "Microencapsulating and Banking Living Cells for Cell-Based Medicine," J Healthc Eng. vol. 2(4), 2011, 427-446.

Notice of Allowance in related co-pending U.S. Appl. No. 11/991,562 mailed Jan. 17, 2013.

Anonymous: "Vascular Disease," XP002619794, Wikipedia 2011.

Bartsch: "Evalulerung von alginatverkapselten Endostatin sezernierenden Stammzellen zur Behandlung des Glioblastomas," Dissertation, Hannover XP002549494.

During, M.J., et al.: "Glucagon-like Peptide-1 Receptor is involved in Learning and Neuroprotection," Nature Medicine, vol. 9(9), 2003.

Erdogdu, O., et al.: "Exendin-4 Stimulates Proliferation of Human Coronary Artery Endothelial Cells Through eNOS-, PKA- and P13K/Akt-Dependent Pathways and Requires GLP-1 Receptor," Molecular and Cell Endocrinology, vol. 325, pp. 26-35, 2010.

Gundewar, et al.: "A Degradation Product of GLP-1 Confers Protection Against Acute Myocardial Ischemia Reperfusion Injury in Diabetes Mellitus," Journal of the American College of Cardiology, vol. 51(10), p. A378 (XP002519012).

Heile, A., et al.: "GLP-1 Secreting Encapsulated Human Mesnechymal Stem Cells for Neuroprotection," Cerebrospinal Fluid Research, vol. 4(Suppl.1), p. S47, 2007.

Heile, Anna M. B., et al.: "Cerebral Transplantation of Encapsulated Mesenchymal Stem Cells Improves Cellular Pathology After Experimental Traumatic Brain Injury," Neuroscience Letter, vol. 463, pp. 176-181, 2009.

Kleinschmidt: "Untersuchung von Endostatin freisetzenden Stammzellimplantaten zur Behandlung des Glioblastoms im Ranttenmoddell," Dissertation, Hannover XP002549495.

Liu, H., et al.: "A Long-Acting Glucagon-Like Peptide-1 Analogue Attenuates Induction of Plaminogen Activator Inhibitor Type-1 and Vascular Adhesion Molecules," Journal of Endocrinology, vol. 201, pp. 59-66, 2009.

Malik, et al.: "Early Evaluation of Genetically Engineered Mesenchymal Stromal Stem Cell Therapy for the Prevention of Left Ventricular Dysfunction in Pigs," Heart, vol. 95(Suppl. 1), pp. A65-A66, XP002619792.

Marneros, A.G., et al.: "Endogenous Endostatin Inhibits Choroidal Neovascularization," The FASEB Journal, vol. 21, pp. 3809-3818, 2007.

McKnight, et al.: "Synthesis of Chitosan-Alginate Microcapsule Membranes," Journal of Bioactive and Compatible Polymers, vol. 3, pp. 334-355, 1988, (XP002112137).

Nikolaidis, L. A., et al.: "Effects of Glucagon-Like Peptide-1 in Patients with Acute Myocardial Infarction and Left Ventricular Dysfunction after Successful Reperfusion," Circulation, vol. 109, pp. 962-965, 2004.

Takahashi, K., et al.: "Intraocular Expression of Endostatin Reduces VEGF-Induced Retinal Vascular Permeability, Neovascularization, and Retinal Detachment," The FASEB Journal, vol. 17(8), pp. 896-898, 2003.

Zhang, R., et al.: "Intraocular Cell-Based Production of Glucagon-Like Peptide-1 in the Anterior Chamber," Acta Ophthalmologica, vol. 86(6), pp. e348-e349, 2010.

\* cited by examiner

A)

B)

```
                        SEQUENCE LISTING

<160> NUMBER OF SEQ ID NOS: 30

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Asp Phe Pro Glu Glu Val Ala Ile Val Glu Glu Leu Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Asp Phe Pro Glu Glu Val Ala Ile Ala Glu Glu Leu Gly
1               5                   10                  15

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg Lys
        35

<210> SEQ ID NO 5
<211> LENGTH: 35
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 5

His Ala Asp Gly Ser Phe Ser Asp Glu Met Ser Thr Ile Leu Asp Asn
1               5                   10                  15

Leu Ala Thr Arg Asp Phe Ile Asn Trp Leu Ile Gln Thr Lys Ile Thr
            20                  25                  30

Asp Lys Lys
        35

<210> SEQ ID NO 6
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Ala Glu Glu Leu Gly Arg Arg
        35                  40                  45

His Ala Glu Gly Thr Phe Thr Ser Asp Val Ser Ser Tyr Leu Glu Gly
    50                  55                  60

Gln Ala Ala Lys Glu Phe Ile Ala Trp Leu Val Lys Gly Arg Gly
65                  70                  75

<210> SEQ ID NO 7
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Ala Glu Glu Leu Gly Arg Arg
        35                  40                  45

His Ala Asp Gly Ser Phe Ser Asp Glu Met Ser Thr Ile Leu Asp Asn
    50                  55                  60

Leu Ala Thr Arg Asp Phe Ile Asn Trp Leu Ile Gln Thr Lys Ile Thr
65                  70                  75                  80

Asp Lys Lys

<210> SEQ ID NO 8
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

-continued

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Ala Glu Glu Leu Gly
        35                  40                  45

<210> SEQ ID NO 9
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Pro Ala Ala Trp Leu Arg Ser Ala Ala Arg Ala Leu Leu
1               5                   10                  15

Pro Pro Met Leu Leu Leu Leu Leu Gln Pro Pro Leu Leu Ala Arg
            20                  25                  30

Ala Leu Pro Pro Asp Val His His Leu His Ala Glu Arg Arg Gly Pro
        35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg

<210> SEQ ID NO 10
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Arg Asp Phe Pro Glu Glu Val Ala Ile Val Glu Glu Leu Gly Arg Arg
        35                  40                  45

His Ala Glu Gly Thr Phe Thr Ser Asp Val Ser Ser Tyr Leu Glu Gly
    50                  55                  60

Gln Ala Ala Lys Glu Phe Ile Ala Trp Leu Val Lys Gly Arg Gly
65                  70                  75

<210> SEQ ID NO 11
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

His Ala Glu Gly Thr Phe Thr Ser Asp Val Ser Ser Tyr Leu Glu Gly
```

```
1               5                   10                  15
Gln Ala Ala Lys Glu Phe Ile Ala Trp Leu Val Lys Gly Arg Gly Arg
                20                  25                  30

Arg Asp Phe Pro Glu Glu Val Ala Ile Val Glu Glu Leu Gly Arg Arg
                35                  40                  45

His Ala Asp Gly Ser Phe Ser Asp Glu Met Asn Thr Ile Leu Asp Asn
            50                  55                  60

Leu Ala Ala Arg Asp Phe Ile Asn Trp Leu Ile Gln Thr Lys Ile Thr
65                  70                  75                  80

Asp Arg Lys

<210> SEQ ID NO 12
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
                20                  25                  30

Arg Asp Phe Pro Glu Glu Val Ala Ile Val Glu Glu Leu Gly
                35                  40                  45

<210> SEQ ID NO 13
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Pro Ala Ala Trp Leu Arg Ser Ala Ala Ala Arg Ala Leu Leu
1               5                   10                  15

Pro Pro Met Leu Leu Leu Leu Leu Gln Pro Pro Pro Leu Leu Ala Arg
                20                  25                  30

Ala Leu Pro Pro Asp Val His His Leu His Ala Glu Arg Arg Gly Pro
            35                  40                  45

Gln Pro Trp His Ala Ala Leu Pro Ser Ser Pro Ala Pro Ala Pro Ala
        50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg His Ala Glu Gly Thr Phe Thr Ser Asp Val Ser Ser Tyr Leu Glu
                100                 105                 110

Gly Gln Ala Ala Lys Glu Phe Ile Ala Trp Leu Val Lys Gly Arg Gly
            115                 120                 125

Arg Arg Asp Phe Pro Glu Glu Val Ala Ile Val Glu Glu Leu Gly Arg
        130                 135                 140

Arg His Ala Glu Gly Thr Phe Thr Ser Asp Val Ser Ser Tyr Leu Glu
145                 150                 155                 160

Gly Gln Ala Ala Lys Glu Phe Ile Ala Trp Leu Val Lys Gly Arg Gly
                165                 170                 175
```

<210> SEQ ID NO 14
<211> LENGTH: 815
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (11)..(118)
<220> FEATURE:
<221> NAME/KEY: CDS
<222> LOCATION: (387)..(806)

<400> SEQUENCE: 14

```
gatatccacc atg gcc ccc gcc gcc tgg ctg agg agc gcc gcc gcc agg         49
           Met Ala Pro Ala Ala Trp Leu Arg Ser Ala Ala Ala Arg
             1               5                  10 gcc ctg ctg cca ccc atg ctg ctg ctg ctg cag ccc cca cct ctg            97
Ala Leu Leu Pro Pro Met Leu Leu Leu Leu Gln Pro Pro Pro Leu
 15                  20                  25 ctg gcc cgg gcc ctg ccc ccg gtgagtgccc gccactcgcc gtccgctcct          148
Leu Ala Arg Ala Leu Pro Pro
 30                  35 cgctgagggg gcgccgggca cgcgggctgg gcccagcggc gtatccggac gccaagaaac     208
cagagagcca gccagatgcc aaagggcccct gccatgtgcc ggtgcccttt ccctctccat    268
ttgccctgcc acacagtggg ctggggttgc acgtgtgttt gctgacaggc cacatctcta    328
actgtgggcc atgtggacct taggcctgac cagaccctca tgtcttcctc cttcccag     386 gac gtg cac cac ctg cac gcc gag agg cgc ggc cct cag ccc tgg cac       434
Asp Val His His Leu His Ala Glu Arg Arg Gly Pro Gln Pro Trp His
             40                  45                  50 gcc gcc ctg cca agc agc cct gcc cct gcc cca gcc acc cag gag gcc       482
Ala Ala Leu Pro Ser Ser Pro Ala Pro Ala Pro Ala Thr Gln Glu Ala
                 55                  60                  65 ccc agg cct gcc agc agc ctg agg cca ccc agg tgc ggc gtg cct gat       530
Pro Arg Pro Ala Ser Ser Leu Arg Pro Pro Arg Cys Gly Val Pro Asp
 70                  75                  80 ccc tcc gat ggc ctg agc gct cgg aat cgg cag aag agg cac gcc gag       578
Pro Ser Asp Gly Leu Ser Ala Arg Asn Arg Gln Lys Arg His Ala Glu
 85                  90                  95                 100 ggc acc ttc acc tcc gac gtg agc agc tac ctg gag ggc cag gcc gcc       626
Gly Thr Phe Thr Ser Asp Val Ser Ser Tyr Leu Glu Gly Gln Ala Ala
                105                 110                 115 aag gag ttc atc gcc tgg ctg gtg aag ggc agg ggc cgc agg gac ttc       674
Lys Glu Phe Ile Ala Trp Leu Val Lys Gly Arg Gly Arg Arg Asp Phe
                120                 125                 130 cct gag gag gtg gcc atc gtg gag gag ctg ggc cgg cga cac gcc gag       722
Pro Glu Glu Val Ala Ile Val Glu Glu Leu Gly Arg Arg His Ala Glu
135                 140                 145 ggc acc ttc acc tcc gac gtg agc agc tac ctg gag ggc cag gcc gcc       770
Gly Thr Phe Thr Ser Asp Val Ser Ser Tyr Leu Glu Gly Gln Ala Ala
                150                 155                 160 aag gag ttc atc gcc tgg ctg gtg aag ggc agg ggc tgagcgcgc              815
Lys Glu Phe Ile Ala Trp Leu Val Lys Gly Arg Gly
165                 170                 175
```

<210> SEQ ID NO 15
<211> LENGTH: 180
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 15

Met Ala Pro Ala Ala Trp Leu Arg Ser Ala Ala Arg Ala Leu Leu
1               5                   10                  15

Pro Pro Met Leu Leu Leu Leu Gln Pro Pro Leu Leu Ala Arg
            20                  25                  30

Ala Leu Pro Pro Asp Val His Leu His Ala Glu Arg Gly Pro
        35              40                  45

Gln Pro Trp His Ala Ala Leu Pro Ser Ser Pro Ala Pro Ala
50              55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg His Ala Glu Gly Thr Phe Thr Ser Asp Val Ser Ser Tyr Leu Glu
                100                 105                 110

Gly Gln Ala Ala Lys Glu Phe Ile Ala Trp Leu Val Lys Gly Arg Gly
                115                 120                 125

Arg Arg Asp Phe Pro Glu Glu Val Ala Ile Val Glu Glu Leu Gly Arg
130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
        180

<210> SEQ ID NO 16
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (11)..(118)
<220> FEATURE:
<221> NAME/KEY: CDS
<222> LOCATION: (387)..(818)

<400> SEQUENCE: 16
gatatccacc atg gcc ccc gcc gcc tgg ctg agg agc gcc gcc gcc agg         49
           Met Ala Pro Ala Ala Trp Leu Arg Ser Ala Ala Ala Arg
           1               5                   10 gcc ctg ctg cca ccc atg ctg ctg ctg ctg cag ccc cca cct ctg            97
Ala Leu Leu Pro Pro Met Leu Leu Leu Leu Leu Gln Pro Pro Leu
15                  20                  25 ctg gcc cgg gcc ctg ccc ccg gtgagtgccc gccactcgcc gtccgctcct          148
Leu Ala Arg Ala Leu Pro Pro
30                  35 cgctgagggg gcgccgggca cgcgggctgg gcccagcggc gtatccggac gccaagaaac    208
cagagagcca gccagatgcc aaagggccct gccatgtgcc ggtgcccttt ccctctccat    268
ttgccctgcc acacagtggg ctggggttgc acgtgtgttt gctgacaggc acatctcta    328 actgtgggcc atgtggacct taggcctgac cagacccctca tgtcttcctc cttcccag     386
```

```
gac gtg cac cac ctg cac gcc gag agg cgc ggc cct cag ccc tgg cac       434
Asp Val His His Leu His Ala Glu Arg Arg Gly Pro Gln Pro Trp His
         40                  45                  50 gcc gcc ctg cca agc agc cct gcc cct gcc cca gcc acc cag gag gcc       482
Ala Ala Leu Pro Ser Ser Pro Ala Pro Ala Pro Ala Thr Gln Glu Ala
             55                  60                  65 ccc agg cct gcc agc agc ctg agg cca ccc agg tgc ggc gtg cct gat       530
Pro Arg Pro Ala Ser Ser Leu Arg Pro Pro Arg Cys Gly Val Pro Asp
 70                  75                  80 ccc tcc gat ggc ctg agc gct cgg aat cgg cag aag agg cac gcc gag       578
Pro Ser Asp Gly Leu Ser Ala Arg Asn Arg Gln Lys Arg His Ala Glu
 85                  90                  95                 100 ggc acc ttc acc tcc gac gtg agc agc tac ctg gag ggc cag gcc gcc       626
Gly Thr Phe Thr Ser Asp Val Ser Ser Tyr Leu Glu Gly Gln Ala Ala
                    105                 110                 115 aag gag ttc atc gcc tgg ctg gtg aag ggc agg ggc cgc agg gac ttc       674
Lys Glu Phe Ile Ala Trp Leu Val Lys Gly Arg Gly Arg Arg Asp Phe
                120                 125                 130 cct gag gag gtg gcc atc gtg gag gag ctg ggc cgg cga cac gcc gac       722
Pro Glu Glu Val Ala Ile Val Glu Glu Leu Gly Arg Arg His Ala Asp
            135                 140                 145 ggc agc ttc agc gac gag atg aac acc atc ctg gac aac ctg gcc gcg       770
Gly Ser Phe Ser Asp Glu Met Asn Thr Ile Leu Asp Asn Leu Ala Ala
150                 155                 160 cgc gac ttc atc aac tgg ctg atc cag acc aag atc acc gat cgg aag       818
Arg Asp Phe Ile Asn Trp Leu Ile Gln Thr Lys Ile Thr Asp Arg Lys
165                 170                 175                 180 tgagcgcgct gatatc                                                     834

<210> SEQ ID NO 17
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Pro Ala Ala Trp Leu Arg Ser Ala Ala Ala Arg Ala Leu Leu
1               5                   10                  15

Pro Pro Met Leu Leu Leu Leu Leu Gln Pro Pro Leu Leu Ala Arg
            20                  25                  30

Ala Leu Pro Pro Asp Val His His Leu His Ala Glu Arg Arg Gly Pro
            35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160
```

Asn Leu Ala Ala Arg
165

<210> SEQ ID NO 18
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (11)..(118)
<220> FEATURE:
<221> NAME/KEY: CDS
<222> LOCATION: (387)..(773)

<400> SEQUENCE: 18

```
gatatccacc atg gcc ccc gcc gcc tgg ctg agg agc gcc gcc gcc agg         49
           Met Ala Pro Ala Ala Trp Leu Arg Ser Ala Ala Ala Arg
             1               5                  10 gcc ctg ctg cca ccc atg ctg ctg ctg ctg cag ccc cca cct ctg              97
Ala Leu Leu Pro Pro Met Leu Leu Leu Leu Gln Pro Pro Pro Leu
 15                  20                  25 ctg gcc cgg gcc ctg ccc ccg gtgagtgccc gccactcgcc gtccgctcct            148
Leu Ala Arg Ala Leu Pro Pro
 30                  35 cgctgagggg gcgccgggca gcgggctgg gcccagcggc gtatccggac gccaagaaac       208
cagagagcca gccagatgcc aaagggccct gccatgtgcc ggtgcccttt ccctctccat       268
ttgccctgcc acacagtggg ctggggttgc acgtgtgttt gctgacaggc acatctcta       328 actgtgggcc atgtggacct taggcctgac cagaccctca tgtcttcctc cttcccag        386 gac gtg cac cac ctg cac gcc gag agg cgc ggc cct cag ccc tgg cac        434
Asp Val His His Leu His Ala Glu Arg Arg Gly Pro Gln Pro Trp His
                 40                  45                  50 gcc gcc ctg cca agc agc cct gcc cct gcc cca gcc acc cag gag gcc        482
Ala Ala Leu Pro Ser Ser Pro Ala Pro Ala Pro Ala Thr Gln Glu Ala
             55                  60                  65 ccc agg cct gcc agc agc ctg agg cca ccc agg tgc ggc gtg cct gat        530
Pro Arg Pro Ala Ser Ser Leu Arg Pro Pro Arg Cys Gly Val Pro Asp
         70                  75                  80 ccc tcc gat ggc ctg agc gct cgg aat cgg cag aag agg cac gcc gag        578
Pro Ser Asp Gly Leu Ser Ala Arg Asn Arg Gln Lys Arg His Ala Glu
 85                  90                  95                 100 ggc acc ttc acc tcc gac gtg agc agc tac ctg gag ggc cag gcc gcc        626
Gly Thr Phe Thr Ser Asp Val Ser Ser Tyr Leu Glu Gly Gln Ala Ala
                105                 110                 115 aag gag ttc atc gcc tgg ctg gtg aag ggc agg ggc cgc agg gac ttc        674
Lys Glu Phe Ile Ala Trp Leu Val Lys Gly Arg Gly Arg Arg Asp Phe
            120                 125                 130 cct gag gag gtg gcc atc gtg gag gag ctg ggc cgg cga cac gcc gac        722
Pro Glu Glu Val Ala Ile Val Glu Glu Leu Gly Arg Arg His Ala Asp
        135                 140                 145 ggc agc ttc agc gac gag atg aac acc atc ctg gac aac ctg gcc gcg        770
Gly Ser Phe Ser Asp Glu Met Asn Thr Ile Leu Asp Asn Leu Ala Ala
    150                 155                 160 cgc tgatatc                                                             780
Arg
165
```

<210> SEQ ID NO 19
<211> LENGTH: 143

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Pro Ala Ala Trp Leu Arg Ser Ala Ala Arg Ala Leu Leu
1               5                   10                  15

Pro Pro Met Leu Leu Leu Leu Gln Pro Pro Leu Leu Ala Arg
            20                  25                  30

Ala Leu Pro Pro Asp Val His His Leu His Ala Glu Arg Arg Gly Pro
            35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg His Ala Glu Gly Thr Phe Thr Ser Asp Val Ser Ser Tyr Leu Glu
                100                 105                 110

Gly Gln Ala Ala Lys Glu Phe Ile Ala Trp Leu Val Lys Gly Arg Gly
            115                 120                 125

Arg Arg Asp Phe Pro Glu Glu Val Ala Ile Val Glu Glu Leu Gly
        130                 135                 140

<210> SEQ ID NO 20
<211> LENGTH: 716
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (11)..(118)
<220> FEATURE:
<221> NAME/KEY: CDS
<222> LOCATION: (387)..(707)

<400> SEQUENCE: 20
gatatccacc atg gcc ccc gcc gcc tgg ctg agg agc gcc gcc gcc agg        49
           Met Ala Pro Ala Ala Trp Leu Arg Ser Ala Ala Ala Arg
           1               5                   10 gcc ctg ctg cca ccc atg ctg ctg ctg ctg cag ccc cca cct ctg            97
Ala Leu Leu Pro Pro Met Leu Leu Leu Leu Leu Gln Pro Pro Leu
       15                   20                  25 ctg gcc cgg gcc ctg ccc ccg gtgagtgccc gccactcgcc gtccgctcct         148
Leu Ala Arg Ala Leu Pro Pro
30                  35 cgctgagggg cgccgggca cgcgggctgg gcccagcggc gtatccggac gccaagaaac      208
cagagagcca gccagatgcc aaagggccct gccatgtgcc ggtgcccttt ccctctccat     268
ttgccctgcc acacagtggg ctggggttgc acgtgtgttt gctgacaggc cacatctcta    328
actgtgggcc atgtggacct taggcctgac cagaccctca tgtcttcctc cttcccag      386 gac gtg cac cac ctg cac gcc gag agg cgc ggc cct cag ccc tgg cac       434
Asp Val His His Leu His Ala Glu Arg Arg Gly Pro Gln Pro Trp His
        40                  45                  50 gcc gcc ctg cca agc agc cct gcc cct gcc cca gcc acc cag gag gcc       482
Ala Ala Leu Pro Ser Ser Pro Ala Pro Ala Pro Ala Thr Gln Glu Ala
        55                  60                  65

```
ccc agg cct gcc agc agc ctg agg cca ccc agg tgc ggc gtg cct gat         530
Pro Arg Pro Ala Ser Ser Leu Arg Pro Pro Arg Cys Gly Val Pro Asp
        70                  75                  80 ccc tcc gat ggc ctg agc gct cgg aat cgg cag aag agg cac gcc gag         578
Pro Ser Asp Gly Leu Ser Ala Arg Asn Arg Gln Lys Arg His Ala Glu
 85                  90                  95                 100 ggc acc ttc acc tcc gac gtg agc agc tac ctg gag ggc cag gcc gcc         626
Gly Thr Phe Thr Ser Asp Val Ser Ser Tyr Leu Glu Gly Gln Ala Ala
                    105                 110                 115 aag gag ttc atc gcc tgg ctg gtg aag ggc agg ggc cgc agg gac ttc         674
Lys Glu Phe Ile Ala Trp Leu Val Lys Gly Arg Gly Arg Arg Asp Phe
                120                 125                 130 cct gag gag gtg gcc atc gtg gag gag ctg ggc tgagcgcgc                   716
Pro Glu Glu Val Ala Ile Val Glu Glu Leu Gly
        135                 140
```

<210> SEQ ID NO 21
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30
```

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Arg Arg Asp Phe Pro Glu Glu Val Ala Ile
 1               5                  10
```

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Arg Arg Asp Phe Pro Glu Glu Val Ala Ile Val Glu Glu Leu
 1               5                  10
```

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Arg Arg Asp Phe Pro Glu Glu Val Ala Ile Ala Glu Glu Leu
 1               5                  10
```

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Gly or not present

<400> SEQUENCE: 25

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 26
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Pro Ala Ala Trp Leu Arg Ser Ala Ala Arg Ala Leu Leu
1               5                   10                  15

Pro Pro Met Leu Leu Leu Leu Leu Gln Pro Pro Leu Leu Ala Arg
            20                  25                  30

Ala Leu Pro Pro Asp Val His His Leu His Ala Glu Arg Arg Gly Pro
        35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Glu Gly Thr Phe Thr Ser Asp Val Ser Ser Tyr Leu Glu
145                 150                 155                 160

Gly Gln Ala Ala Lys Glu Phe Ile Ala Trp Leu Val Lys Gly Arg Gly
                165                 170                 175

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Gln Lys Arg
1

```
<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-histidine, D-histidine, desamino-histidine,
      2-amino-histidine, 3-hydroxy-histidine, homohistidine, N-acetyl-
      histidine, a-fluoromethyl-histidine, a-methyl-histidine,
      3-pyridylalanine, 2-pyridylalanine or 4-pyridylalanine
<220> FEATURE:
<221> NAME/KEY: MOD_RES
<222> LOCATION: (2)..(2)
<223> OTHER INFORMATION: Ala, Gly, Val, Leu, Ile, Lys, aminoisobutyric
      acid, (1-aminocyclopropyl), (1-aminocyclobutyl),
      (1-aminocyclopentyl), (1-aminocyclohexyl), (1-aminocycloheptyl),
      or (1-aminocyclooctyl) carboxylic acids
<220> FEATURE:
<221> NAME/KEY: MOD_RES
<222> LOCATION: (10)..(10)
<223> OTHER INFORMATION: Val or Leu
<220> FEATURE:
<221> NAME/KEY: MOD_RES
<222> LOCATION: (12)..(12)
<223> OTHER INFORMATION: Ser, Lys or Arg
<220> FEATURE:
<221> NAME/KEY: MOD_RES
<222> LOCATION: (13)..(13)
<223> OTHER INFORMATION: Tyr or Gln
<220> FEATURE:
<221> NAME/KEY: MOD_RES
<222> LOCATION: (14)..(14)
<223> OTHER INFORMATION: Leu or Met
<220> FEATURE:
<221> NAME/KEY: MOD_RES
<222> LOCATION: (16)..(16)
<223> OTHER INFORMATION: Gly, Glu or aminoisobutyric acid
<220> FEATURE:
<221> NAME/KEY: MOD_RES
<222> LOCATION: (17)..(17)
<223> OTHER INFORMATION: Gln, Glu, Lys or Arg
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Lys, Glu or Arg
<220> FEATURE:
<221> NAME/KEY: MOD_RES
<222> LOCATION: (21)..(21)
<223> OTHER INFORMATION: Glu or Leu
<220> FEATURE:
<221> NAME/KEY: MOD_RES
<222> LOCATION: (24)..(24)
<223> OTHER INFORMATION: Ala, Glu or Arg
<220> FEATURE:
<221> NAME/KEY: MOD_RES
<222> LOCATION: (27)..(27)
<223> OTHER INFORMATION: Val or Lys
<220> FEATURE:
<221> NAME/KEY: MOD_RES
<222> LOCATION: (28)..(28)
<223> OTHER INFORMATION: Lys, Glu, Asn or Arg
<220> FEATURE:
<221> NAME/KEY: MOD_RES
<222> LOCATION: (29)..(29)
<223> OTHER INFORMATION: Gly or aminoisobutyric acid
<220> FEATURE:
<221> NAME/KEY: MOD_RES
<222> LOCATION: (30)..(30)
<223> OTHER INFORMATION: Arg, Gly, Lys or not present
```

-continued

```
<220> FEATURE:
<221> NAME/KEY: MOD_RES
<222> LOCATION: (31)..(31)
<223> OTHER INFORMATION: Gly, Ala, Glu, Pro, Lys or not present

<400> SEQUENCE: 28

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-histidine, D-histidine, desamino-histidine,
      2-amino-histidine, 3-hydroxy-histidine, homohistidine, N-acetyl-
      histidine, a-fluoromethyl-histidine, a-methyl-histidine,
      3-pyridylalanine, 2-pyridylalanine or 4-pyridylalanine
<220> FEATURE:
<221> NAME/KEY: MOD_RES
<222> LOCATION: (2)..(2)
<223> OTHER INFORMATION: Ala, Gly, Val, Leu, Ile, Lys, aminoisobutyric
      acid, (1-aminocyclopropyl), (1-aminocyclobutyl),
      (1-aminocyclopentyl), (1-aminocyclohexyl), (1-aminocycloheptyl),
      or (1-aminocyclooctyl) carboxylic acids
<220> FEATURE:
<221> NAME/KEY: MOD_RES
<222> LOCATION: (12)..(12)
<223> OTHER INFORMATION: Ser, Lys or Arg
<220> FEATURE:
<221> NAME/KEY: MOD_RES
<222> LOCATION: (16)..(16)
<223> OTHER INFORMATION: Gly, Glu or aminoisobutyric acid
<220> FEATURE:
<221> NAME/KEY: MOD_RES
<222> LOCATION: (17)..(17)
<223> OTHER INFORMATION: Gln, Glu, Lys or Arg
<220> FEATURE:
<221> NAME/KEY: MOD_RES
<222> LOCATION: (20)..(20)
<223> OTHER INFORMATION: Lys, Glu or Arg
<220> FEATURE:
<221> NAME/KEY: MOD_RES
<222> LOCATION: (24)..(24)
<223> OTHER INFORMATION: Ala, Glu or Arg
<220> FEATURE:
<221> NAME/KEY: MOD_RES
<222> LOCATION: (28)..(28)
<223> OTHER INFORMATION: Lys, Glu or Arg
<220> FEATURE:
<221> NAME/KEY: MOD_RES
<222> LOCATION: (29)..(29)
<223> OTHER INFORMATION: Gly or aminoisobutyric acid
<220> FEATURE:
<221> NAME/KEY: MOD_RES
<222> LOCATION: (30)..(30)
<223> OTHER INFORMATION: Arg, Lys or not present
<220> FEATURE:
<221> NAME/KEY: MOD_RES
<222> LOCATION: (31)..(31)
<223> OTHER INFORMATION: Gly, Ala, Glu, Lys or not present

<400> SEQUENCE: 29

Xaa Xaa Glu Gly Thr Phe Thr Ser Asp Val Ser Xaa Tyr Leu Glu Xaa
1               5                   10                  15

Xaa Ala Ala Xaa Glu Phe Ile Xaa Trp Leu Val Xaa Xaa Xaa Xaa
            20                  25                  30
```

```
<210> SEQ ID NO 30
<211> LENGTH: 584
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (31)..(558)

<400> SEQUENCE: 30
aattcagata attcgatagc cccgggcacc atg gct ccc gct gca tgg ctg aga        54
                                 Met Ala Pro Ala Ala Trp Leu Arg
                                  1               5 tct gcg gcc gcg cgc gcc ctc ctg ccc ccg atg ctg ctg ctg ctc            102
Ser Ala Ala Ala Arg Ala Leu Leu Pro Pro Met Leu Leu Leu Leu
     10                  15                  20 cag ccg ccg ccg ctg ctg gcc cgg gct ctg ccg ccg gac gtc cac cac        150
Gln Pro Pro Pro Leu Leu Ala Arg Ala Leu Pro Pro Asp Val His His
 25                  30                  35                  40 ctc cat gcc gag agg agg ggg cca cag ccc tgg cat gca gcc ctg ccc        198
Leu His Ala Glu Arg Arg Gly Pro Gln Pro Trp His Ala Ala Leu Pro
                 45                  50                  55 agt agc ccg gca cct gcc cct gcc acg cag gaa gcc ccc cgg cct gcc        246
Ser Ser Pro Ala Pro Ala Pro Ala Thr Gln Glu Ala Pro Arg Pro Ala
             60                  65                  70 agc agc ctc agg cct ccc cgc tgt ggc gtg ccc gac cca tct gat ggg        294
Ser Ser Leu Arg Pro Pro Arg Cys Gly Val Pro Asp Pro Ser Asp Gly
         75                  80                  85 ctg agt gcc cgc aac cga cag aag agg cat gcc gaa ggg acc ttt acc        342
Leu Ser Ala Arg Asn Arg Gln Lys Arg His Ala Glu Gly Thr Phe Thr
 90                  95                 100 agc gat gtg agc tct tat ctg gaa ggc cag gct gcc aag gag ttc att        390
Ser Asp Val Ser Ser Tyr Leu Glu Gly Gln Ala Ala Lys Glu Phe Ile
105                 110                 115                 120 gct tgg ctg gtg aaa ggc cgg gga agg cgg gat ttc cca gag gag gtg        438
Ala Trp Leu Val Lys Gly Arg Gly Arg Arg Asp Phe Pro Glu Glu Val
                125                 130                 135 gcc atc gtg gag gag ctg ggc cgg cga cat gcc gaa ggg acc ttt acc        486
Ala Ile Val Glu Glu Leu Gly Arg Arg His Ala Glu Gly Thr Phe Thr
            140                 145                 150 agc gat gtg agc tct tat ctg gaa ggc cag gct gcc aag gag ttc att        534
Ser Asp Val Ser Ser Tyr Leu Glu Gly Gln Ala Ala Lys Glu Phe Ile
        155                 160                 165 gct tgg ctg gtg aaa ggc cgg gga tgaattgcca agggcgaatt atcagg          584
Ala Trp Leu Val Lys Gly Arg Gly
    170                 175
```

SPHERICAL MICROCAPSULES COMPRISING GLP-1 PEPTIDES, THEIR PRODUCTION AND USE

CROSS REFERENCE TO RELATED APPLICATIONS

This application is a U.S. National Phase Application of International Application No. PCT/EP2007/003775 filed Apr. 27, 2007, which claims the benefit of European Patent Application No. 06009678.1, filed May 10, 2006, each of which is incorporated by reference in its entirety.

SEQUENCE LISTING

The instant application contains a Sequence Listing which has been submitted via EFS-Web and is hereby incorporated by reference in its entirety. Said ASCII copy, created on Nov. 13, 2009, is named 067802-5018-SequenceListing.txt, and is 36,963 bytes in size.

The present application refers to spherical microcapsules comprising at least one surface coating and a core, wherein the at least one surface coating comprises cross-linked polymers, and wherein the core comprises cross-linked polymers and cells capable of expressing and secreting a GLP-1 peptide, a fragment or variant thereof or a fusion peptide comprising GLP-1 or a fragment or variant thereof. The present application is furthermore directed to methods thr producing these spherical microcapsules and to the use of these microcapsules e.g. in the treatment of type 2 diabetes, weight disorders and diseases or conditions associated thereto, neurodegenerative disorders and diseases or conditions associated thereto, or for the treatment of disorders and diseases or conditions associated to apoptosis.

The glucagon gene is well studied, see e.g. White, J. W. et al., 1986 Nucleic Acid Res. 14(12) 4719-4730. The preproglucagon molecule as a high molecular weight precursor molecule is synthesized in pancreatic alpha cells and in the jejunum and colon L cells. Preproglucagon is a 180 amino acid long prohormone and its sequence contains, in addition to glucagon, two sequences of related structure: glucagon-like peptide-1 (GLP-1) and glucagon-like peptide-2 (GLP-2). In the preproglucagon molecule, between GLP-1 and GLP-2 is a 17 amino acid peptide sequence (or rather a 15 amino acid sequence plus the C-terminal RR cleavage site), intervening peptide 2 (IP2). The IP2 sequence (located between GLP-1 and -2 the precursor molecule) is normally cleaved proteolytically after aa 37 of GLP-1. The preproglucagon module is therefore cleaved into various peptides, depending on the cell, and the environment, including GLP-1 (1 -37), a 37 amino acid peptide in its unprocessed form. Generally, this processing occurs in the pancreas and the intestine. The GLP-1 (1-37) sequence can be further proteolytically processed into active GLP-1 (7-37), the 31 amino acid processed form, or GLP-1 (7-36) amide. Accordingly, the designation GLP-1 (7-37) means that the fragment in question comprises the amino acid residues from (and including) number 7 to (anti including) number 37 when counted from the N-terminal end of the parent peptide, GLP-1. The amino acid sequence of GLP-1 (7-36)amide and of GLP-1 (7-37) is given in formula I (SEQ ID NO: 25):

(I)

His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-Gly-Arg-X which shows GLP-1 (7-36)amide when X is $NH_2$ and GLP-1 (7-37) when X is Gly-OH.

GLP-1 is a gut hormone and the most potent endogenous insulinotropic agent with actions that include stimulating adenylate cyclase and protein kinase activity in the beta-cell. Physiologically, together with gastric inhibitory polypeptide from the upper gut, it functions as an incretin hormone lowering the blood glucose level. Accordingly, GLP-1, secreted in response to food intake, has e.g. multiple effects on the stomach, liver, pancreas and brain that work in concert to regulate blood sugar. Consequently, Glucagon-like peptide GLP-1 (7-36)amide, and its non-amidated analogue GLP-1 (7-37) have attracted considerable interest because of their potent actions on carbohydrate metabolism and its potential applicability to the treatment of diabetes, including type 2 diabetes. Type 2 diabetes is characterized by insulin resistance, since cells do not respond appropriately when insulin is present. This is a more complex problem than type 1 diabetes. Type 2 diabetes may go unnoticed for years in a patient before diagnosis, since the symptoms are typically milder (no ketoacidosis) and can be sporadic. Though, severe complications can result from unnoticed type 2 diabetes, including renal failure and coronary heart disease. This leads to increased morbidity and mortality.

However, GLP-1 (7-36)amide or GLP-1 (7-37) is short-lived in serum. The peptide is cleaved by dipeptidyl peptidase IV (DPP-IV) between residues 8 and 9 resulting in an inactive peptide. Thus GLP-1, administered exogenously, is extremely short-lived in the patient treated and, therefore, does not exert its physiological effects in therapeutic applications.

Various attempts have been made to synthesize stabilized (against DPP-IV) analogues of naturally occurring GLP-1 (GLP-1 (7-37)). In particular, the $8^{th}$ residue, which in vivo is Ala, was replaced by another residue, for instance, Gly, Ser or Thr (Burcelin, R. et al. (1999) Metabolism 48, 252-258). The Gly8 or G8 analogue has been extensively tested, both as synthesized molecule, and produced by cell lines genetically engineered to secrete the mutant polypeptide (Burcelin, R., et al (1999) Annals of the New York Academy of Sciences 875: 277-285). Various other modifications have been introduced into GLP-1 (7-37) to enhance its in vivo stability without compromising its biological activity. However, all of these approaches did not achieve any therapeutic significance due to considerable problems involved.

Furthermore, none of these approaches allows a long-term provision of GLP-1 in vivo. This is due to proteolytical degradation as discussed above, to metabolism of GLP-1 and normal protein degradation typically occurring in the body. Thus, the patient, in need of GLP-1, has to receive one or even multiple doses of GLP-1 or its analogs or variants within short intervals during a long period of time or, even worse, for a whole life span or, anyhow, as long as he suffers from the disease to be treated. Accordingly, doses of GLP-1 have to be administered either by a medical doctor or by the patient himself in order to circumvent this problem, GLP-1 may be administered by providing cells to a patient containing a nucleic acid encoding and expressing GLP-1. Implantation of such cells would ensure a longer provision of GLP-1 in vivo and, due to secretion of GLP-1 from the grafted cells, provide GLP-1 directly at the site of interest.

E.g. WO 99/53064 discloses a strategy for creating a multimeric GLP-1 expression cassette which can be incorporated into a variety of cell types which are publicly available immortalized cell lines and dividing primary cell cultures. Examples include EGF-responsive neurospheres, bFGF-responsive neural progenitor stem cells from the CNS of mammals, while the worked example uses baby hamster kidney (BHK) cells. The implanted transfected cells were said to have been used to treat successfully diabetic mice, allowing glucose control equivalent substantially to non-diabetic controls. However, this kind of implantation technique does not comply with the requirements for a routine treatment for e.g. diabetes patients.

Moreover, it is e.g. known in the art that the immune system typically recognizes foreign cells and triggers an immune response in order to protect the organism from external material, such as foreign cells. Implantation of cells capable of expressing GLP-1 or any of its variants or derivatives may thus lead to an immune response in the organism. Such a defense response may cause considerable and undesirable side effects during treatment and may lead to severe complications or even death of the treated organism.

In summary, at present there is no efficient diabetes type 2 therapy available in the art, which allows to lower the blood glucose level on the basis of GLP-1 over a long-lasting time period. In other words, the prior art fails to provide a therapy which reflects the entire spectrum of beneficial effects known for GLP-1, e.g. its activity to powerfully reduce the entry of nutrients into the circulation in obese subjects or its insulin stimulating activity without the need of repeated administration of GLP-1 peptide(s) and/or the risk of an undesired immune response against e.g. implanted GLP-1 expressing allogenic cells.

Therefore, it is an object of the present invention to provide GLP-1 based peptide molecules, which are biologically active in vivo over a long-lasting time period without the need of repeated administration of GLP-1 peptide(s) or the risk of evoking an undesired immune response.

The object underlying the present invention is solved by providing a spherical microcapsule comprising at least one surface coating and a (spherical) core, wherein the at least one surface coating comprises or consists of cross-linked polymers, and wherein the (spherical) core comprises or consists of cross-linked polymers and cells capable of expressing and secreting GLP-1, a fragment or variant thereof or a fusion peptide comprising GLP-1 or a fragment or variant thereof.

The (spherical) core of the inventive spherical microcapsule typically comprises or consists of cross-linked polymers and cells capable of expressing and secreting GLP-1, a fragment or variant thereof or a fusion peptide comprising GLP-1 or a fragment or variant thereof.

In the context of the present invention, the cross-linked polymers of the (spherical) core, i.e. the core may be spherical or not, form a scaffold structure embedding the cell(s) in its cavities. The cells may be embedded in the scaffold structure individually or, typically, as aggregates, e.g. as (a pool of) aggregated cells of about 10 to about 10,000 cells, e.g. about 10 to about 500, about 10 to about 1000 or about 10 to about 10000 cells. Preferably, the (spherical) core comprises a homogenous distribution of the cross-linked polymers and of embedded cells capable of expressing and secreting GLP-1, a fragment or variant thereof or a fusion peptide comprising GLP-1 or a fragment or variant thereof. Preferably, the core, including the scaffold structure and the embedded cells as defined above, is prepared according to a method as disclosed below.

Cells may be present in the core of the inventive spherical microcapsule in a concentration of $0.5 \times 10^7$ cells/ml cross-linked scaffold polymer to $5 \times 10^8$ cells/ml cross-linked scaffold polymer, more preferably in a concentration of $1 \times 10^7$ cells/ml cross-linked scaffold polymer to $5 \times 10^7$ cells/ml cross-linked scaffold polymer and most preferably in a concentration of $2 \times 10^7$ cells/ml cross-linked scaffold polymer to $4 \times 10^7$ cells/ml cross-linked scaffold polymer.

Advantageously, the diameter of the core of the inventive spherical microcapsule may vary considerably depending on the specific treatment. Typically, the diameter of the core of the inventive spherical microcapsule ranges from about 20 to about 4000 μm, preferably from about 20 to about 3000 μm and most preferably from about 20 to about 2000 μm.

When preparing inventive spherical microcapsules it is of critical importance to embed the encapsulated (allogenic) cells entirely in the polymer matrix. The term "spherical" is understood in its broadest meaning. A spherical particle is understood to have a sphere-like shape, whereby the shape may be symmetrical or asymmetrical. E.g. a spherical microcapsule may have ellipsoidal shape. In a less preferred embodiment the inventive microcapsule may not be spherical within the above meaning, but may arbitrary shape with e.g. protruding or invading segments on the surface of the microcapsule. Wherever in the present disclosure "spherical" microcapsules are mentioned, "non-spherical" microcapsules may be provided, prepared or used as well.

(Allogenic) cells being located at the core periphery or cells protruding out of the scaffold structure may evoke immunological problems, since the immune system will recognize these microcapsules as foreign components and, thus, these microcapsules will be attacked by the immune system. Although this effect may be avoided by lowering the cell concentration in the initial solution, the present invention allows to improve the efficacy of the microcapsule by increasing the core's cell number. The higher the concentration of encapsulated cells, the smaller the total volume of the resultant microcapsules to be transplanted. In order to avoid immunological problems when using high concentrations of cells in the core the invention provides at least one surface coating applied on the (spherical) core of the inventive spherical microcapsule. This surface coating does not allow an immune response to occur, even if cells are located very closely to the core periphery, since these cells are not accessible for the host's immune system due to the surface coating acting as barrier. This surface coating is typically composed of a cross-linked polymer as defined above without containing any cells. According to a particular embodiment the afore defined (spherical) core is coated with at least one or more than one surface coatings, e.g. 1, 2, 3, 4, 5, 5-10 or more surface coating(s). Typically, each surface coating comprises a uniform thickness around the core. The thickness of the surface coating(s) of the inventive microcapsule may be varied almost arbitrarily and is typically in a range of about 10 to about 4000 μm, preferably in a range of about 10 to about 3000 μm and even more preferably in a range of about 10 to about 2000 μm.

Any (cross-linkable) polymer known in the art as being suitable for encapsulation may be used for the formation of the (spherical) core and the surface coating(s) of the inventive spherical microcapsule. Preferably, such polymers are used, which, on the one hand, are permeable in their cross-linked state far supply of oxygen and nutrients, and, on the other hand, allows diffusion of the peptide expressed and secreted by core cells from the microcapsule into the patient's tissue or body fluids. Furthermore, the cross-linked polymers prevent intrusion of components of the body's immune system through the matrix. By way of example, polymers may be used such as synthetic, semi-synthetic and natural water-soluble (bio)polymers, e.g. from natural polymers such as selected proteins or polymers based on proteins (e.g. collagens, albumins etc.), polyamino acids (e.g. poly-L-lysine, poly-L-glutamic acid, etc.), polysaccharides and their derivatives (e.g. carboxyl methyl cellulose, cellulose sulfate, agarose, alginates including alginates of brown algae (e.g. of species Laminarales, Ectocarpales, Fucales), carrageenans, hyaluronic acid, heparin and related glycosamino sulfates, dextranes and its derivatives, chitosan and its derivatives). Synthetic polymers may also be used such as e.g. aliphatic polyesters (e.g. polylactic acid, polyglycolic acid, polyhydroxybuyrates, etc.), polyamides, polyanhydrides, polyorthoesters, polyphosphazenes, thermoplastic polyurethanes, polyvinyl alcohols, polyhydroxyethylmethacrylates, polymethylmethacrylates and polytetrafluoroethylenes, etc. Furthermore, block polymers may be used herein accordingly, i.e. polymers derived by combination of two or more of the aforementioned polymers. Such block polymers may be selected by a skilled person depending on the desired properties, e.g. pore size, cross-linking status, toxicity, handling, biocompatibility, etc. Any of the above polymers is defined as a "chemically different polymer" in the context of the present invention, i.e. each of these polymers typically does not exhibit an identical molar mass and structure with any other of the above polymers. In contrast, "chemically identical polymers" means, that the polymers exhibit an identical molar mass and structure. Finally, mixtures of the above polymers are also encompassed herein, wherein the amounts of polymers contained in such a mixture may be selected by a skilled person depending on the desired properties, e.g. as outlined above. In this respect, mixtures of polymers may be regarded as chemically identical to another polymer mixture ("chemically identical polymers"), if the overall molar mass of the resultant polymer mixture and the corresponding molar percentage of the single polymers of the mixture is identical to the other polymer mixture.

Preferably, alginate is used according to present invention as a polymer for the formation of the (spherical) core and/or of the surface coating(s) due to their biocompatibility and their cross-linking properties. From a chemical point of view alginates are anionic polysaccharides derived from homopolymeric groups of β-D-mannuronic acid and α-L-guluronic acid, separated by heteropolymeric regions of both acids. Alginates are water soluble and form high viscosity solutions in the presence of monovalent cations such as sodium or potassium. A cross-linked water insoluble hydrogel is formed upon interaction of single alginate chains with bi-, tri- or multivalent cations (such as calcium, barium or polylysin). Preferably, purified alginates (e.g. according to DE 198 36 960, the disclosure of which is incorporated herein by reference) are used for encapsulation, more preferably potassium or sodium alginates in physiological saline solution. Such alginates typically exhibit an average molar mass of about 20 kDa to about 10,000 kDa, more preferably a molar mass of about 100 kDa to about 1,200 kDa. Alginates used for the formation of the core and/or of the surface coating(s) of the inventive microcapsule preferably may be provided as a solution, more preferably as an aqueous solution. E.g. the viscosity of a 0.1% (w/v) aqueous alginate solution of the alginate to be used may be in the range of about 3 to about 100 mPa s, more preferably in the range of about 10 to about 60 mPa s.

If alginates are used according to the present invention, alginates, which are rich in β-D-mannuronic acid (e.g. as disclosed in Biomaterials, Vol. 8, 1997, pp. 707 to 713) are preferred. Alginates suitable for preparing inventive spherical microcapsules are obtainable by extraction from certain algae species including, without being limited thereto, brown algae, e.g. Laminarales, Ectocarpales, Fucales, etc., and other species of algae containing alginates. Alginates may be isolated from fresh algae material or dried material according to any method for preparing alginates known to a skilled person. Preferably the method according to EP 1109837 is applied here, the disclosure of which is incorporated herein by reference. Briefly, the method according to EP 1109837 comprises following steps: The initial algae material is first of all extracted in the presence of complexing agents, where appropriate in soda solution. Next, any cell components and particles present in the solution are brought to sedimentation by adding a granulate, and if required, by adding ion exchangers (such as e.g. Amberlite). The solution is then filtered. The filter step can include multiple filtering with a pore size which decreases with each step, e.g. from 20 μm to 0.2 μm. The alginate is precipitated from the filtered solution by means of a suitable precipitant. The precipitation is preferably carried out with an alcohol (e.g. ethanol). Alternatively, an acid or another suitable precipitant may be used for precipitation. The alcohol concentration in the precipitation solution is typically in the range of between 10% (v/v) and 50% (v/v), preferably in the range of between 30% (v/v) and approximately 50% (v/v). Within this concentration range, impurities due to immunologically active polysaccharides, such as e.g. Fucoidan, remain in solution, and, thus, can be separated from the alginate. During the precipitation, a propellant (e.g. air) preferably flows through the solution. The precipitated alginate is impelled upwards by the injected air, and can easily be separated from the solution surface with a suitable device (e.g. a net, sieve or similar). The collected alginate may then be dried with a filter press. The afore mentioned method steps may be carried out as disclosed above or, additionally, by repeating one or more steps, once or more than once, where appropriate. Furthermore, the afore mentioned method steps may be repeated in partially modified form, dependent upon the application. After the final run, the highly purified alginate is washed in ethanol, and additionally in water, if appropriate, and air-dried at room temperature. Dependent upon the initial material, the purified alginate has a monomeric ratio of mannuronic acid and guluronic acid in the range of 0.1-9 (corresponding to 1% to 90% mannuronic acid) and an average molecular weight of between approximately 10 kD and more than 1,000 kD. This type of purified alginate, implanted in an autoimmune diabetic BB/OK rat does not trigger any immune response, or only a very weak reaction 3 weeks after implantation.

The above defined cross-linked polymers used for preparation of the (spherical) core and the at least one surface coating of the inventive spherical microcapsule may be identical or different. According to a first embodiment the cross-linked polymers used for preparation of the core and the at least one surface coating may comprise chemically identical polymers in identical or differing concentrations. Preferably, the polymers present in the core and the at least one surface coating are prepared using a non-cross-linked polymer solution selected from any of the polymers a defined above. In the polymer solution, the non-cross-linked polymers are typically present in a concentration of about 0.1% (w/v) to about 8% (w/v) of the non-cross-linked polymer, more preferably in a concentration of about 0.1% (w/v) to about 4% (w/v), even more preferably in a concentration of about 0.5% (w/v) to about 2.5% (w/v) and most preferably in a concentration of about 1% (w/v) to about 2% (w/v). If alginates as disclosed above are used as polymers the concentration of the polymer solution for preparing the (spherical) core and the at least one surface coating of the inventive microcapsule furthermore may be selected from 0.1 to 4% (w/v), preferably from 0.4 to 2% (w/v). Different alginate concentrations may be used for preparing the (spherical) core and the at least one surface coating of the inventive microcapsules. Preferably, the non-cross-linked polymers used for preparation of the core and/or the at least one surface coating comprise chemically identical polymers, more preferably in identical concentrations, e.g. in concentrations as defined above with polymers as defined above. In this context the term "% (w/v)" refers to the concentration of non-cross-linked polymers is typically determined on the basis of a certain amount of a polymer in its dry form versus the total volume of the polymer solution, e.g. after solubilizing the non-cross-linked polymer in a suitable solvent (before the cross-linkage). However, the above concentrations may also be indicated in the corresponding "% v/v" concentrations, if applicable, e.g. if polymers are used, which are present in a fluid aggregate state at standard conditions (room temperature, normal pressure, etc.).

According to a second embodiment the cross-linked polymers used for preparation of the core and/or the at least one surface coating may comprise chemically different polymers in identical or differing concentrations. Thereby, concentrations y be chosen as defined above.

Furthermore, polymers may be chosen from polymers as defined above, including e.g. natural polymers, synthetic polymers, and combination of polymers, i.e. block polymers.

Additionally, the polymers in each surface coating may be identical or different, i.e. the cross-linked polymers of each surface coating may comprise chemically identical or different polymers in identical or differing concentrations. E.g. the inventive spherical microcapsule may comprise at least one surface coating, as defined above, consisting of any polymer as defined above, and an additional external surface coating consisting of polycations, e.g. polyamino acids as defined above, e.g. poly-L-lysine, poly-L-glutamic acid, etc. Difference in nature of the polymers used may further be due to different molecular weight of the polymers used and/or due to different cross-linkage of identical polymers, etc.

As shown above, the core of the inventive spherical microcapsule further comprises GLP-1 peptide expressing and secreting cells. These GLP-1 peptide expressing and secreting cells may be selected from any type of cells being capable to express and secrete GLP-1. Such cells are typically obtainable by stably transfecting a cell with a nucleic acid or rather a vector containing a nucleic acid coding for GLP-1, a fragment or variant thereof or a fusion peptide comprising GLP-1 or a fragment or variant thereof, as defined below.

Suitable cells may be chosen from (non-differentiated) stem cells including totipotent, pluripotent, or multipotent stem cells, Stem cells used in the present context preferably comprise embryonic stem cells or stem cells derived from the ektoderm, the mesoderm or the endoderm, or adult stem cells such as (human) mesenchymal stem cells (MSC, hMSC) (e.g. derived from human bone marrow or from fat tissue), hematopoietic stern cells, epidermal stem cells, neural stem cells and immature fibroblasts, including fibroblasts from the skin (myofibroblasts), etc. These (undifferentiated) stein cells are typically capable of symmetric stern cell division, i.e. cell division leading to identical copies. Stem cells maintain the capacity of transforming into any cell type. Moreover, stern cells are capable of dividing asymmetrically leading to a copy of the stem cell and another cell different from the stem cell copy, e.g. a differentiated cell.

Inventive spherical microcapsules may alternatively contain cells which are chosen from (differentiated) cells, e.g. obtainable from the above stern cells, e.g. cells of the connective tissue family, e.g. (mature) fibroblasts, cartilage cells (chondrocytes), bone cells (osteoblasts/osteocytes, osteoclasts), fat cells (adipocytes), or smooth muscle cells, or blood cells including lymphoid progenitor cells or cells therefrom, e.g. NK cells, T-cells, B-cells or dendritic cells, or common myeloid progenitor cells or cells derived therefrom, e.g. dendritic cells, monocytes, macrophages, osteoclasts, neutrophils, eosinophils, basophils, platelets, megakaryocytes or erythrocytes, or macrophages, neuronal cells including astrocytes, oligodendrocytes, etc., or epithelial cells, or epidermal cells. These differentiated cells are typically capable of symmetric cell division, i.e. cell division leading to identical copies of the differentiated parent cell. Moreover, in some cases these differentiated cells may be capable of dividing asymmetrically leading to an identical copy of the parent cell and another cell different from the parent cell, i.e. a cell being further differentiated than the parent cell. Alternatively, in some cases differentiated cells as defined above may be capable of differentiating further without the need of cell division, e.g. by adding selective differentiation factors.

Furthermore, cells embedded in the inventive spherical microcapsule may either be cells taken from the patient to be treated himself (autologous cells) or may be taken from allogenic cells (e.g. taken from an established cell line cultivated in vitro, e.g. HEK293 cells, hTERT-MSC cells, etc.). Due to the surface coating embedding the core in the inventive spherical microcapsule the present invention allows to use allogenic cells without evoking any undesired immune response by the patient to be treated.

A combination of cell types may be present in the core of the inventive spherical microcapsule. E.g. the core of the inventive spherical microcapsule as defined herein may contain human mesenchymal stem cells, wherein a portion of these cells may be differentiated in vitro or in vitro into a cell type as defined above, e.g. adipocytes (suitable for transplantation into fat tissue), etc. Accordingly, various cell types (derived e.g. from a specific stem cell type) may be allocated in the core, e.g. sharing a common lineage.

In summary, cells used according to the present invention for preparing the core of the inventive spherical microcapsule may be selected from non-differentiated or differentiated cells. According to one embodiment non-differentiated cells as defined above may be preferred. Such non-differentiated cells may provide advantageous properties, e.g. a prolonged effect of the inventive spherical microcapsules, e.g. the prolonged capability to express and secrete GLP-1 peptides, e.g. due to a longer life span of such non-differentiated cells. In an alternative embodiment, differentiated cells as defined above may be preferred for preparing the core of the inventive spherical microcapsule, since they typically do not proliferate any more and, thus, do not lead to any undesired proliferation of cells within the core of the inventive spherical microcapsule. Specific differentiation of cells may be carried out by a person in vitro according to methods known in the art adding selected differentiation factors to precursor cells.

Preferably, cells are differentiated in such a way that a vast majority of cells (or at least 90%, more preferably at least 95% and most preferably at least 99%) embedded in the core of the inventive spherical microcapsule belongs to the same cell type. In particular, mesenchymal stem cells as defined above may be differentiated in vitro e.g. into osteoblasts, chondrocytes, adipocytes such as fat cells, neuron-like cells such as brain cells, etc., and used herein accordingly. As to whether non-differentiated or differentiated cells are used for preparing the core of the inventive spherical microcapsule may be dependent on specific requirements of the disease to be treated, e.g. the site of affliction, the administration mode, the tissue chosen for implant, etc. A selection of appropriate cells may be carried out by a skilled person evaluating these criteria.

Furthermore, cells used for preparing the core of the inventive spherical microcapsule may be immortalized or non-immortalized cells, preferably immortalized cells. If immortalized cells are used, these cells preferably retain their capability of symmetric and/or asymmetric cell division as discussed above. According to the present invention cells are defined as immortal when they exceed the double life span of normal cells (i.e. of non-immortalized cells). The maximum life span of normal diploid cells in vitro varies dependent on the cell type (e.g. fetal versus adult cell) and culture conditions. Thus, the maximum life span of cultured normal cells in vitro is approximately 60-80 population doublings. For example, keratinocytes may divide around 80 times, fibroblasts more than 50 times, and lymphocytes about 20 times. Normal bone marrow stromal cells may exhibit a maximum life span of 30-40 population doublings. Preferably, a cell line used for preparation of the core of an inventive spherical microcapsule may continuously grow past 350 population doublings and may still maintain a normal growth rate characteristic of young cells.

Methods for immortalizing cells are widely known in the art and may be applied here accordingly (see e.g. WO 03/010305 or WO 98/66827, which are incorporated herein by reference). An exemplary method (according to WO 03/010305) comprises e.g. following steps:
a) culturing cells e.g. stem cells, in particular stem cells derived from human bone marrow (e.g. (human) mesenchymal stem cells (MSC, hMSC)), in accordance with standard conventional cell culturing methods known to the skilled person;
b) transducing said cell cultures with a retroviral vector, comprising at least a fragment of the human telomeric repeat subunit (hTRT) gene or a variant thereof, by
  b1) culturing a packaging cell line (e.g. PA317 cells, PG13 cells, Phenix, etc.), wherein the packaging cell line are cells in which the retroviral vector is produced,
  b2) constructing a retroviral vector (derived from Moloney murine leukemia virus, etc.), wherein the retroviral vector comprises at least a fragment of the catalytic subunit of the human telomeric repeat (hTRT) gene or a variant thereof, more preferably a hTERT cDNA fragment, e.g. a 3452 base pair EcoRI fragment from pGRN 145 (Geron Corporation),
  b3) transfecting said packaging cell line, with said retroviral vector,
  b4) transducing said packaging cell line with said transfected cells, preferably by centrifuging the cells with the retroviral vector
  b5) transducing cultured cells according to step a) above with the packaging cells of step b4), said cells comprising said retroviral vector.
c) obtaining an immortal cell line, wherein said immortalized cell line has substantially identical characteristics and properties compared to the cells of step a). As a result the inserted polynucleotide sequence derived from the human telomeric subunit (hTRT) gene may be transcribed and translated to produce a functional telomerase. One of skill will recognize that due to codon degeneracy a number of polynucleotide sequences will encode the same telomerase. In addition, telomerase variants are included, which have sequences substantially identical to a wildtype telomerase sequence and retain the function of the wildtype telomerase polypeptide (e.g. resulting from conservative substitutions of amino acids in the wildtype telomerase polypeptide).

A GLP-1 peptide expressed and secreted by a cell contained in the inventive spherical microcapsule may be selected from any known GLP-1 peptide sequence. In this context, cells embedded in the core of the inventive spherical microcapsule are typically transfected prior to preparing the core with nucleic acid sequences encoding such a GLP-1 peptide such that these cells express and secrete the GLP-1 peptide. Preferably a GLP-1 peptide expressed and secreted by a cell contained in the inventive spherical microcapsule may be selected from a group consisting of a peptide comprising aa 7-35 of GLP-1 and a peptide showing a homology of at least 80%, 90%, 95% or even 99% with this peptide. More preferably, the peptide GLP-1 may be selected from group consisting of a peptide comprising aa 1-37 of GLP-1, a peptide comprising aa 7-35, 36 or 37 of GLP-1, GLP-1 (7-36) amide and a peptide showing a homology of at least 80%, 90%, 95% or even 99% with any of these peptides, including modified peptides. In this context, a "modified GLP-1 peptide" is intended to mean any GLP-1 variant or a GLP-1 fragment, including combinations, e.g. a fragment of a variant. Variants and fragments are categorized as modifications of the unmodified sequence, e.g. GLP-1 (7-35, 36 or 37). Within the meaning of the present invention any variant or fragment has to be functional, e.g. has to exert the same or a similar biological activity as the unmodified (GLP-1) peptide. The term "activity" refers to the biological activity (e.g. one or more of the biological activities comprising receptor binding, activation of the receptor, exhibition of insulinotrophic activity, i.e. the ability to promote insulin secretion, the ability to lower glucagon secretion, the ability to affect weight loss, etc.), which may be compared under the same conditions for the naturally occurring GLP-1 peptide as defined herein and any fragment or variant thereof. Preferably, a variant or fragment of a GLP-1 peptide as defined herein exerts at least 25% activity of a GLP-1 (7-35, 36 or 37), more preferably at least 50% (biological) activity, even more preferably 60, 70, 80 or 90% (biological) activity and most preferably at least 95 or 99% (biological) activity of a GLP-1 (7-35, 36 or 37).

According to an alternative embodiment, a GLP-1 peptide expressed and secreted by cells embedded in the core of the inventive spherical microcapsule may be selected from a GLP-1 fusion peptide or a variant or fragment thereof. The GLP-1 fusion peptides as defined herein have at least two components, e.g. components (I) and (II), components (I) and (III) or components (I), (II) and (III), exhibit GLP-1's biological activity and, simultaneously, confer stability to component (I) of GLP-1 fusion peptides by a C-terminal elongation. Component (I) of GLP-1 fusion peptides as defined herein contains a sequence having at least 80%, more preferably at least 85% and even more preferably at least 90% sequence homology with SEQ ID NO: 1. SEQ ID NO:1 represents the native amino acid sequence of GLP-1 (7-37) (length of 31 amino acids), which is strictly conserved among mammalians.

Component (II) of the GLP-1 fusion peptide expressed and secreted by cells embedded in the core of the inventive spherical microcapsule (or more generally any GLP-1 peptide including fragments or variants of fusion peptides) typically contains a peptide sequence having at least nine amino acids. Component (II) of the GLP-1 fusion peptide furthermore may contain at least one proline residue in its sequence. Proline residues are common amino acids within a β-turn forming tetrameric amino acid sequence. Thus, component (II) of the GLP-1 fusion peptide may form a β-turn like structure. A β-turn structure is a typical secondary structure element of proteins or peptides. It is typically formed by four amino acids, which revert the direction of the peptide's or protein's backbone chain direction. If present, the praline residue is commonly located at position 2 or 3, preferably at position 2, of a tetrameric β-turn sequence occurring in component (II) of the GLP-1 fusion peptide.

Cells embedded in the core of the inventive spherical microcapsule are typically transfected prior to preparing the core with nucleic acid sequences encoding such a GLP-1 fusion peptide such that these cells express and secrete the GLP-1 fusion peptide. Particularly preferred in this context is a GLP-1 fusion peptide as defined herein, wherein component (II) is a peptide sequence containing a sequence according to SEQ ID NO: 22 (RRDFPEEVAI) (all peptide sequences given in the one-letter-code) or a sequence having at least 80% sequence homology with SEQ ID NO: 22. SEQ ID NO: 22 is a partial sequence of the hill-length IP-2 (intervening peptide 2) sequence, which contains the 10 N-terminal amino acids of the 15 amino acid long full-length IP-2 sequence. IP-2 is a preferred example of a component (II) as used herein. Accordingly, other stronger preferred sequences being contained in component (II) are longer partial amino acid sequences of IP-2, such as the 14 N-terminal amino acid sequence occurring in humans (SEQ ID NO: 23 (RRDFPE-EVAIVEEL)) or its murine counterpart (SEQ ID NO: 24 (RRDFPEEVAIAEEL)) or a sequence having at least 80% sequence homology with SEQ ID NOs: 23 or 24. Most preferred as elements being contained in component (II) of the fusion peptide are full-length IP-2 sequences having all 15 amino acids of the naturally occurring IP-2 sequence (SEQ ID NO: 2 (RRDFPEEVAIVEELG), human, or SEQ ID NO: 3 (RRDFPEEVAIAEELG), murine) or a sequence having at least 80% sequence homology with SEQ ID NOs: 2 or 3. Within the scope of the present invention are also all mammalian isoforms of IP2 (natural variants of IP2 among mammalians). More than one copy of a sequence being included into component (II) may be provided, e.g. 2, 3 or even more copies of IP2 or a fragment or variant of IP2.

Accordingly, a GLP-1 fusion peptide, expressed and secreted by cells embedded in the core of the inventive spherical microcapsule, preferably contains sequences according to SEQ ID NO: 8 (HAEGTFTSDVSSYLEGQAAKEFI-AWLVKGRGRRDFPEEVAIAEELG), i.e. GLP-1 (7-37) linked without any linker sequence via its C-terminus to murine IP2 or according to SEQ ID NO: 12 (HAEGTFTSD-VSSYLEGQAAKEFIAWLVKGRGRRDEPE-EVAIVEELG), i.e. GLP-1 (7-37) linked without any linker sequence via its C-terminus to human IP2. Variants or fragments thereof having a sequence homology of at least 80% with SEQ ID NOs: 8 and 12 or fragments or variants thereof may be used herein as well. Preferred GLP1-fusion peptides in this context may further comprise sequences according to SEQ ID NOs: 13, 14, 19 and 20.

Without being bound to any theory, it is concluded by the inventors of the present invention that the instability of GLP-1 (7-35, 36 or 37), if secreted in vivo by cells embedded in the core or the implanted inventive spherical microcapsule into the patients surrounding tissue, is due to its unprotected 3-dimensional structure. Proteases may cleave the GLP-1 (7-35, 36 or 37) peptide and abolish its physiological activity rapidly in vivo. By linking a peptide sequence to the C-terminus of GLP-1(7-35, 36 or 37) its structure gains stability towards enzymatic degradation. Such gain In stability may be enhanced, if the additional C-terminal peptide sequence (being contained component (II) the fusion peptide according to the invention) folds back, e.g. due to the presence of a β-turn structural element formed by its primary structure and providing rigidity to component (II). The GLP-1 peptide as defined above, by virtue of its C-terminal peptide extension preferably containing a β-turn structural element, is found to have improved resistance to DPP-IV inactivation. The C-terminal peptide is either not cleaved from the GLP-1 (7-35, 36 or 37) sequence prior to acting on its receptor in target cells or it may be cleaved enzymatically to form GLP-1 (7-35, 36 or 37) in vivo. Irrespective of the exact form of the GLP-1 peptide bound at the site of the GLP-1 receptor, an GLP-1 peptide as defined above exerts its function as an active insulinotropic compound.

GLP-1 peptide sequences, which are considered to be suitable for being contained in component (II) of a GLP-1 fusion peptide as defined above due to a primary structure forming a β-turn element may readily be identified by adequate e.g. spectroscopic methods, e.g. circular dichroism, or other methods known to the skilled person.

Component (II) and component (I) of a GLP-1 fusion peptide expressed and secreted by cells embedded in the core of the inventive spherical microcapsule may be directly linked or linked via a linker sequence. Preferably, both components are directly linked with each other. In case they are linked via a linker (or spacer), the linker is preferably a peptide linker. A peptide linker typically has a length of 1 to 10 amino acids, preferably 1 to 5, even more preferably 1 to 3 amino acids, in some cases the linker sequence may be even longer comprising 11 to 50 amino acids. A peptide linker may be composed of various (naturally occurring) amino acid sequences. Preferably, a peptide linker will introduce some structural flexibility between components to be linked. Structural flexibility is achieved e.g. by having a peptide linker containing various glycine or proline residues, preferably at least 30%, more preferably at least 40% and even more preferably at least 60% proline and glycine residues within the linker sequence. Irrespective of the specific sequence the peptide linker may preferably be immunologically inactive.

GLP-1 fusion proteins expressed and secreted by cells embedded in the core of the inventive spherical microcapsule may additionally contain a component (III). Generally, component (III) comprises at least four amino acid residues, preferably at least 10 additional amino acid residues, more preferably at least 20, or at least 30. In functional terms, component (III) is intended to further enhance the stability of an GLP-1 peptide. Component (III) is expected not to interfere with the biological function of the GLP-1 fusion peptide which is approximately comparable to the biological activity of GLP-1 (7-37). Generally spoken, any C-terminal elongation of component (I) defined herein, whether it is component (II), component (III) or a combination of components (II) and (III) as defined herein, enhances stability of component (I), i.e. a GLP-1 (7-37) or its fragment or variant as defined herein.

Preferably, component (III) of the GLP-1 fusion peptide encoded by nucleic acids transfected into cells used according to the present invention for preparing the core of the inventive spherical microcapsule comprises at least 4, preferably at least 10, more preferably at least 20 additional amino acid residues of the N-terminal sequence of an isoform of GLP-2 of any mammalian organism (other naturally occurring variant of GLP-2 among mammalian), e.g. murine or human isoforms as shown in SEQ ID NOs: 4 and 5. GLP-2 occurs in pro-glucagon and is also involved in carbohydrate metabolism. In the context of the present invention, the term "GLP-2 peptide" preferably means GLP-2 (1-33, 34, or 35), whereas "modified GLP-2 peptide" is intended to mean any GLP-2 fragment or variant, or a fragment or variant of GLP-2 (1-33, 34 or 35). Variants or fragments are categorized as modifications of the unmodified sequence, e.g. GLP-2 (1-33, 34 or 35). As with the biologically active sequence included in component (I) (GLP-1 peptide), component (III) may also comprise variants or fragments of naturally occurring forms of GLP-2. Alternatively, component (III) may also comprise at least 4, preferably at least 10, more preferably at least 20 additional amino acid residues of the N-terminal sequence of GLP-1 (7-37), correspondingly including all mammalian isoforms or—as disclosed herein—all functional fragments or variants thereof. Generally speaking, component (III) may contain any form of a GLP-1 peptide or a modified GLP-1 peptide, which is disclosed herein as suitable for component (I) of the GLP-1 fusion peptide. In a further alternative, component (III) may also contain chimeric forms of GLP-1 (7-37) and GLP-2. A chimeric form may be produced by coupling GLP-1 (7-37) and GLP-2 (or fragments or variants) with each other and by subsequently introducing this chimeric form as component (III) into the GLP-1 fusion peptide. Preferably, the chimeric form is composed of a partial sequence of GLP-1 (7-37) and a partial sequence of GLP-2 linked together. E.g. the chimeric form may include the N-terminal 5 to 30 amino acids of GLP-1 and the C-terminal 5 to 30 amino acids of GLP-2 or vice versa, e.g. amino acids 7 or 8 to 22, 23, 24, 25, 26, 27, or 28 of GLP-1 (7-37) and amino acid sequence from position 15, 16, 17, 18, 19, 20, 21, 22, 23 or 24 to e.g. the C-terminus of GLP-2.

If modifications of naturally occurring forms of GLP-2 or GLP-1 (7-37), respectively, are contained as component (III), component (III) preferably contains the sequence of SEQ ID NOs: 4 or 5 or SEQ ID NO: 1, respectively, or a sequence having at least 80% sequence homology with SEQ ID NOs: 4 or 5 or SEQ ID NO: 1.

In another embodiment, component (III) of the GLP-1 fusion peptide expressed and secreted by cells embedded in the core of the inventive spherical microcapsule may contain a plurality of sequences as described above. E.g. component (III) may contain at least two, preferably 2, 3, or 4 copies of GLP-1 (7-37) and/or GLP-2 or at least two copies of sequences having at least 80% sequence homology with SEQ ID NOs: 1, 4 or 5. Also, component (III) may contain more than one copy of a chimeric version of GLP-1 (7-37) or GLP-2, as disclosed above, e.g. eventually forming a combination of chimeric version(s) together with GLP-1 (7-37) and/or GLP-2 or its modifications with at least 80% sequence homology. A GLP-1 fusion peptide encoded by nucleic acids transfected into cells used according to the present invention for preparing the core of the inventive spherical microcapsule may also comprise two or more, preferably two, components (III), which may e.g. be (1) linked by its N-terminus to the C-terminus of component (I) or (II) and (2) linked by its C-terminus to the N-terminus of component (I) via a linker or directly. If two components (III) are provided, these may be identical or different.

According to a preferred embodiment, cells (embedded in the core of the inventive spherical microcapsules) are preferred, which are transfected with nucleic acids encoding GLP-1 fusion peptides containing three components (I), (II) and (III). Four specific embodiments containing all of these components are selected from a group consisting of SEQ ID NO: 6 (N-GLP-1 (7-37)-IP2(murine)-RR-GLP-1 (7-37)-C, also designated murine CM1 herein), SEQ ID NO: 7 (N-GLP)-1(7-37)-IP2(murine)-RR-GLP2-C, also designated marine CM2 herein), SEQ ID NO: 10 (N-GLP-1(7-37)-IP2 (human)-RR-GLP-1 (7-37)-C, also designated human CM1), and SEQ ID NO: 11 (N-GLP-1 (7-37)-IP2 (human)-RR-GLP-2-C), also designated human CM2 herein) or a sequence having at least 80% sequence homology with SEQ ID NOs: 6, 7, 10, or 11 or a fragment or variant thereof. All sequences according to SEQ ID NOs, 6, 7, 10 and 11 contain an RR-Linker (two arginine residues) at the C-terminus of IP2 (component (II)), which may alternatively also be discarded. Component (I) in each of the embodiments according to SEQ ID NOs: 6, 7, 10 or 11 is GLP-1 (7-37), whereas component (III) (in each of these embodiments linked to the C-terminus of component (II)) is either GLP-1 (7-37) or GLP-2. Preferred GLP1-fusion peptides in this context may further comprise sequences according to SEQ ID NOs: 15, 16, 17, 18 and 26.

In another preferred embodiment of the present invention, a GLP-1 fusion peptide expressed and secreted by cells embedded in the core of the inventive spherical microcapsule contains in addition to component (I) a component (III) (without any component (II) as defined above) which is either (inked to the C-terminus of component (I) and/or to the N-terminus of component (I). Preferably, component (III) is located at the C-terminus of component (I). Irrespective of whether component (III) is linked to the N-terminus of component (I) (by its C-terminus) or to the C-terminus of component (I) (by its N-terminus), the coupling may be direct or indirect via a linker sequence. With regard to the linker sequence it is referred to the above disclosure for a linker connecting component (I) and component (II).

In an alternative preferred embodiment of the present invention, a GLP-1 fusion peptide expressed and secreted by cells embedded in the core of the inventive spherical microcapsule contains in addition to components (I) and (II) a component (III) which is either linked to the C-terminus of component (II) and/or to the N-terminus of component (I). Preferably, component (III) is located at the C-terminus of component (II). Irrespective of whether component (III) is linked to the N-terminus of component (I) (by its C-terminus) or to the C-terminus of component (II) (by its N-terminus), the coupling may be direct or indirect via a linker sequence. With regard to the linker sequence it is again referred to the above disclosure for a linker connecting component (I) and component (II).

Finally, the GLP-1 fusion protein embedded in the core of the inventive spherical microcapsule may comprise in addition to any of the afore mentioned combinations of components of the fusion protein (i.e. components (I) and (II), components (I) and (III) or components (I), (II) and (III)) a carrier protein, in particular transferrin or albumin, as component (IV). Such a component (IV) may be linked to the N- and/or C-terminus of any of the afore mentioned combinations of components of the fusion protein, i.e. components (I) and (II), components (I) and (III) or components (I), (II) and (III), either directly or using a linker as defined above.

The GLP-1 peptides as defined above, encoded by nucleic acids transfected into cells used according to the present invention for preparing the core of the inventive spherical microcapsule, may occur in various modified forms. These modified forms are disclosed in the following and described in more detail.

A "fragment" of a GLP-1 peptide expressed and secreted by a cell as embedded in the inventive spherical microcapsule refers to any subset of the above disclosed GLP-1 peptides including GLP-1 fusion peptides, that is, a shorter peptide which retains the desired biological activity. Fragments may readily be prepared by removing amino acids from either end of time molecule and testing the resultant for its properties as a incretin. Proteases for removing one amino acid at a time from either the N-terminal end and/or the C-terminal end of a polypeptide are known, and so determining fragments which retain the desired biological activity involves only routine experimentation. Conclusively, fragments may be due to deletions of amino acids at the peptide termini and/or of amino acids positioned within the peptide sequence.

Additionally, the GLP-1 peptide as defined herein which has anti-diabetes type 2 activity, be it a fusion peptide itself, a functional variant and/or fragment thereof, can also contain additional amino acid residues flanking the GLP-1 peptide. As long as the resultant molecule retains its resistance or stability towards proteases and its ability to act as incretin, one can determine whether any such flanking residues affect the basic characteristics of the core peptide, e.g. by its effects on pancreas cells, by routine experimentation. The term "consisting essentially of", when referring to a specified sequence, means that additional flanking residues can be present which do not affect the basic characteristic of the specified GLP-1 peptide. This term does not comprehend substitutions, deletions or additions within the specified sequence.

A "variant" of a GLP-1 peptide expressed and secreted by a cell as embedded in the inventive spherical microcapsule refers to a molecule which is substantially similar to either the entire GLP-1 peptide defined above or a fragment thereof. Variant peptides may be conveniently prepared using methods well known in the art. Of course, such variant of a GLP-1 peptide would have similar anti-diabetic, e.g. insulin stimulating activity as the corresponding naturally-occurring GLP-1 peptide. E.g. amino acid sequence variants of the GLP-1 peptides defined above can be prepared by mutations in the DNA sequences which encode the synthesized variants. Such variants include, for example, deletions from, or insertions or substitutions of, residues within the amino acid sequence. Any combination of deletion, insertion, and substitution may also contained in GLP-1 peptides expressed and secreted by a cell as embedded in the inventive spherical microcapsule, provided that the final construct possesses the desired activity. Obviously, the mutations that will be made in the DNA encoding the variant peptide must not alter the reading frame and preferably will not create complementary regions that could produce secondary mRNA structure.

The types of substitutions which may be contained in the GLP-1 peptide expressed and secreted by a cell embedded in the inventive spherical microcapsule, may be based on analysis of the frequencies of amino acid changes between a homologous protein/peptide of different species. Based upon such analysis, conservative substitutions may be defined herein as exchanges within one of the following five groups:

I. Small, aliphatic, non-polar or slightly polar residues Ala, Ser, Thr, Pro, Gly, II. Polar, negatively-charged residues their amides: Asp, Asn, Glu, Gln; III. Polar, positively-charged residues: His, Arg, Lys; IV. Large, aliphatic non-polar residues: Met, Len, Ile, Val, Cys; V. Large aromatic residues: Phe, Try, Trp.

Within the foregoing groups, the following substitutions are considered to be "highly conservative": Asp/Glu; His/Arg/Lys; Phe/Tyr/Trp; Met/Leu/Ile/Val. Semi-conservative substitutions are defined to be exchanges between two of groups (I)-(IV) above which are limited to supergroup (A), comprising (I), (II), and (III) above, or to supergroup (B), comprising (IV) and (V) above. Substitutions are not limited to the genetically encoded or even the naturally-occurring amino acids.

In general, variants of the GLP-1 peptides (and GLP-1 fission peptides) defined above may also contain amino acid substitutions, made e.g. with the intention of improving solubility (replacement of hydrophobic amino acids with hydrophilic amino acids).

In one embodiment the (modified) GLP-1 peptide as expressed and secreted by a cell as embedded in the inventive spherical microcapsule, including a GLP-1 fusion peptide as defined above (occurring in component (I) and/or (III) of the GLP-1 fusion peptide), is characterized by one or more substitution(s) at positions 7, 8, 11, 12, 16, 22, 23, 24, 25, 27, 30, 33, 34, 35, 36, or 37 of the GLP-1 peptide. As an example for the following nomenclature [Arg34-GLP-1 (7-37)] designates a GLP-1 analogue wherein the naturally occurring lysine at position 34 has been substituted with arginine.

Specifically, a GLP-1 peptide or component (I) and/or (III) of a GLP-1 fusion peptide as defined herein may correspond to variants of GLP-1 (7-35, 36, 37 or 38) including, for example, Gln9-GLP-1 (7-37), D-Gln9-GLP-1 (7-37), acetyl-Lys9-GLP-1 (7-37), Thr16-Lys18-GLP-1 (7-37), and Lys18-GLP-1 (7-37), Arg34-GLP-1 (7-37), Lys38-Arg26-GLP-1 (7-38)-OH, Lys36-Arg26-GLP-1 (7-36), Arg26,34-Lys38-GLP-1 (7-38), Arg26,34-Lys38-GLP-1 (7-38), Arg26,34-Lys38-GLP-1(7-38), Arg26,34-Lys38-GLP-1 (7-38), Arg26, 34-Lys38-GLP-1 (7-38), Arg26-Lys38-GLP-1(7-38), Arg26-Lys38-GLP-1 (7-38). Arg26-Lys38-GLP-1 (7-38), Arg34-Lys38-GLP-1 (7-38), Ala37-Lys38-GLP-1 (7-38), and Lys37-GLP-1 (7-37).

In a particular preferred embodiment of the invention the GLP-1 peptide as expressed and secreted by a cell as embedded in the inventive spherical microcapsule including a GLP-1 fusion peptide as defined above (with respect to component (I) or (III)) is/contains a (modified) GLP-1 peptide, which is selected from GLP-1 (7-35), GLP-1 (7-36), GLP-1 (7-36)-amide, GLP-1 (7-37) or a fragment or variant thereof.

Preferably, the variant of the GLP-1 peptide (including a variant of a GLP-1 fusion peptide (with respect to component (I) or (III))), expressed and secreted by a cell embedded in the inventive spherical microcapsule, will have a core sequence, which is the same as that of the "native" sequence, e.g. GLP-1 (7-37) or GLP-2 or biologically active fragment thereof or any IP2 isoform, which has an amino acid sequence having at least 70% identity to the native amino acid sequence and retains the biological activity thereof. More preferably, such a sequence exhibits at least 80% identity, at least 90% identity, or most preferably at least 95% identity to the native sequence.

The term "sequence identity" as defined herein means that the sequences are compared as follows. To determine the percent identity of two amino acid sequences, the sequences can be aligned for optimal comparison purposes (e.g., gaps can be introduced in the sequence of a first amino acid sequence). The amino acids at corresponding amino acid positions can then be compared. When a position in the first sequence is occupied by the same amino acid as the corresponding position in the second sequence, then the molecules are identical at that position. The percent identity between the two sequences is a function of the number of identical positions shared by the sequences. E.g. where a particular peptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria. Such a determination of percent identity of two sequences can be accomplished using a mathematical algorithm. A preferred, non-limiting example of a mathematical algorithm utilized for the comparison of two sequences is the algorithm of Karlin et al. (1993), PNAS USA, 90:5873-5877. Such an algorithm is incorporated into the NBLAST program, which can be used to identify sequences having the desired identity to the amino acid sequence of the invention. To obtain gapped alignments for comparison purposes, Gapped BLAST can be utilized as described in Altschul et al. (1997), Nucleic Acids Res, 25:3389-3402. When utilizing BLAST and Gapped BLAST programs, the default parameters of the respective programs (e.g., NBLAST) can be used. The sequences further may be aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence. The described methods of determination of the percent identity of two amino acid sequences can be applied correspondingly to nucleic acid sequences.

The GLP-1 peptides secreted from cells embedded in the inventive spherical microcapsules, particularly GLP-1 fusion peptides, may be protected against proteolytic cleavage as outlined above. They may be preferably protected against dipeptidyl aminopeptidase-IV (DPP-IV). GLP-1 peptides as defined herein as well as their fragments and variants, particularly GLP-1 fusion peptides, may contain a sequence of GLP-1, e.g. GLP-1 (7-35, 36 or 37) (in case of GLP-1 fusion peptides as part of component (I) and/or (III)), resistant to the plasma peptidase (DPP-IV).

Resistance of a peptide to degradation by dipeptidyl aminopeptidase IV is determined e.g. by the following degradation assay: Aliquots of the peptides are incubated at 37° C. with an aliquot of purified dipeptidyl aminopeptidase IV for 4-22 hours in an appropriate buffer at pH 7-8 (buffer not being albumin). Enzymatic reactions are terminated by the addition of trifluoroacetic acid, and the peptide degradation products are separated and quantified using HPLC or LC-MS analysis. One method for performing this analysis is The mixtures are applied onto a Zorbax300SB-C18 (30 nm pores, 5 µm particles) 150×2.1 mm column and eluted at a flow rate of 0.5 ml/min with a linear gradient of acetonitrile in 0.1% trifluoroacetic acid (0%-100% acetonitrile over 30 min). Peptides and their degradation products may be monitored by their absorbance at 214 nm (peptide bonds) or 280 nm (aromatic amino acids), and are quantified by integration of their peak areas. The degradation pattern can be determined by using LC-MS where MS spectra of the separated peak can be determined. Percentage intact/degraded compound at a given time is used for estimation of the peptides DPP-IV stability.

A GLP-1 (fusion) peptide as defined herein and as secreted from cells embedded in the inventive spherical microcapsules, is defined as DPP-IV stabilized when it is 10 times more stable than the non-modified peptide sequence of GLP-1 (7-37) based on percentage intact compound at a given time. Thus, a DPP-IV stabilized GLP-1 peptide is preferably at least 10, more preferably at least 20 times more stable than e.g. GLP-1 (7-37). Stability may be assessed by any method known to the skilled person, e.g. by adding DPP-IV to a solution of the peptide to be tested and by determining the degradation of the peptide (see above), e.g. over a period of time, by e.g. a spectroscopic method, Western-Blot analysis, antibody screening etc. In parallel, a GLP-1 peptide (e.g. fragment and/or variant or a GLP-1 peptide) as defined above is defined as a compound, which exerts the effect of GLP-1 (7-37) by e.g. binding to its native receptor (GLP-1 receptor). Preferably, a GLP-1 (fusion) peptide as defined above has a binding affinity to the GLP-1 receptor, which corresponds to at least 10%, preferably at least 50% of the binding affinity of the naturally occurring GLP-1 peptide. The binding affinity may be determined by any suitable method, e.g. surface plasmon resonance etc. Moreover, it is preferred, if the GLP-1 (fusion) peptide as defined herein evokes formation of intracellular cAMP by its binding to its extracellular receptor, which transmits the signal into the cell.

For in vitro control purposes the GLP-1 (fusion) peptide as defined herein may be isolated from the cells from which it is expressed, for instance using conventional separation techniques. Thus cells may be grown under appropriate conditions, for instance including support and nutrients, in vitro, and secreted protein, i.e. the GLP-1 peptide as defined above, is recovered from the extracellular medium. The sequences engineered into cells thus preferably include signal (peptide) sequences (see below) allowing secretion of the GLP-1 peptide as defined above (see below). The cells preferably express a protease capable of cleaving the signal sequences, either naturally endogenously or after transfection of introduced into the cell by genetic engineering methods. In an alternative, the engineered gene sequences encoding an GLP-1 peptide do not include such signal peptide sequences, whereby the intracellularly expressed GLP-1 peptide will typically not be secreted, and is recovered from cells by processes involving cell lysis. In such methods the coding sequences may include purification tags allowing efficient extraction of the product peptide from the medium; tags may be cleaved off to release isolated GLP-1 peptide. However, this alternative is generally irrelevant to cells of an inventive microcapsule, which are implanted into the patient and require delivery of a GLP-1 peptide into the surrounding tissue.

The GLP-1 peptides as defined above are produced in cells as defined above, i.e. expressed and secreted in cells embedded in the core of the inventive spherical microcapsule. For this purpose, GLP-1 peptides as defined above or its fragments or variants are encoded by nucleic acid sequences being contained in these cells. These nucleic acid sequences may occur naturally in the cells or may be introduced into the cells by cell transfection techniques prior to the preparation of the inventive spherical microcapsule. According to the present invention any suitable nucleic acid sequence coding for a GLP-1 peptide as defined above may be used. Due to degeneracy of the genetic code a plurality of nucleic acid sequences may code for such a GLP-1 peptide. According to a preferred embodiment of the present invention a nucleic acid sequence used for transfection of cells as defined herein may comprise a nucleic acid sequence coding for the GLP-1 peptide(s) as defined above aid additional (functional) nucleotide sequences. The present invention provides preferably a nucleic acid sequence suitable for transfection of a cell as defined herein which may code (a) for the entire GLP-1 aa sequence (GLP-1 (1-37) or functional GLP-1 (7-35, 36 or 37) (variant) sequences or any other GLP-1 peptide, including GLP-1 fusion peptides as defined above, (b) optionally for a protease cleavage sequence at the N-terminus of the GLP-1 sequence according to (a) and, optionally, for a signal peptide sequence upstream from (b). Preferably, the signal (peptide) sequence is selected from a sequence as defined below.

The nucleic acid sequence as defined above may be contained in a vector. This vector may be used to transfect a cell as defined herein suitable for preparing the inventive spherical microcapsule. Typically, such a vector, in particular an expression vector, contains at least one nucleic acid sequence as defined above. A "vector" within the meaning of the present invention advantageously comprises at least one nucleic acid sequence encoding a GLP-1 peptide as defined above and, if necessary, additional elements suitable for directing expression of the encoded GLP-1 peptide sequences. One class of vectors as used herein utilizes DNA elements that provide autonomously replicating extrachromosomal plasmids derived from animal viruses (e.g. bovine papilloma virus, polyomavirus, adenovirus, or SV40, etc.). A second class of inventive vectors as used herein relies upon the integration of the desired gene sequences into the host cell chromosome.

Vectors, as defined above, are typically prepared by inserting at least one GLP-1 peptide encoding nucleic acid sequence into suitable vectors. Such suitable vectors are known to a skilled person and may be reviewed e.g. in "Cloning Vectors" (Eds. Pouwels P. H. et al. Elsevier, Amsterdam-N.Y.-Oxford, 1985, ISBN 0 444 904018). Suitable vectors are also intended to include any vector known to a skilled person, such as plasmids, phages, viruses such as SV40, CMV, Baculo virus, Adeno virus, Sindbis virus, transposons, IS-elements, phasmids, phagemides, cosmides, linear or circular DNA. For integration in mammalian cells linear DNA is typically used. Preferably, the vector type used for the present invention corresponds to the specific host cell requirements. Suitable commercially available expression vectors, into which the inventive nucleic acids may be inserted, include pSPORT, pBluescriptIISK, the baculovirus expression vector pBlueBac, and the prokaryotic expression vector pcDNAII, all of which may be obtained from Invitrogen Corp., San Diego, Calif.

A vector as defined herein suitable for transfecting a cell which may be used as constituent of the inventive spherical microcapsule typically combines the GLP-1 encoding nucleic acid sequences with other regulatory elements, which e.g. control expression of the encoded (inventive) ammo acid sequences. Such regulatory elements are e.g. 1) specific to a tissue or region of the body; 2) constitutive; 3) glucose responsive; and/or 4) inducible/regulatable. Regulatory elements herein are preferably selected from regulation sequences and origins of replication (if the vectors are replicated autonomously). Regulation sequences in the scope of the present invention are any elements known to a skilled person having an impact on expression on transcription and/or translation of GLP-1 encoding nucleic acid sequences. Regulation sequences include, apart from promoter sequences so-called enhancer sequences, which may lead to an increased expression due to enhanced interaction between RNA polymerase and DNA. Further regulation sequences of inventive vectors are transcriptional regulatory and translational initiation signals, so-called "terminator sequences", etc. or partial sequences thereof.

Generally, any naturally occurring promoter may be contained in an expression vector suitable for transfecting a cell which may be used for preparing the inventive spherical microcapsule. Such promoters may be selected from any eukaryotic, prokaryotic, viral, bacterial, plant, human or animal, e.g. mammalian promoters. Suitable promoters include, for example, the cytomegalovirus promoter, the lacZ promoter, the gal 10 promoter and the AcMNPV polyhedral promoter, promoters such as cos-, tac-, trp-, tet-, trp-tet-, lpp-, lac-, lpp-lac-, lacIq-, T7-, T5-, T3-, gal-, trc-, ara-, SV40-, SP6, I-PR- or the I-PL-promoter, advantageously being found in gram-negative bacteria. Additionally, promoters may be obtained from gram-positive promoters such as array and SPO2, yeast promoters, such as ADC1, MFα, AC, P-60, CYC1, GAPDH or mammalian promoters such as the cytomegalovirus (CMV) promoter, muscle-specific promoters including mammalian muscle creatine kinase (MCK) promoter, mammalian desmin promoter, mammalian troponin I (TNNI2) promoter, or mammalian skeletal alpha-actin (ASKA) promoter, or liver type pyruvate kinase promoters, particularly those fragments which run ($-183$ to $+12$) or ($-96$ to $+12$) (Thompson, et al. J Biol Chem, (1991). 266:8679-82; Cuif, et al., Mol Cell Biol, (1992). 12:4852-61); the spot 14 promoter (S14, $-290$ to $+18$) (Jump, et al., J. Biol Chem, (1990). 265:3474-8); acetyl-CoA carboxylase (O'Callaghan, et al., J. Biol Chem, (2001). 276:16033-9); fatty acid synthase ($-600$ to $+65$) (Rufo, et al., J Biol Chem, (2001). 28:28); and glucose-6-phosphatase (rat and human) (Schmoll, et al., FEBS Left, (1996). 383:63-6; Argaud, et al., Diabetes, (1996). 45; 1563-71), or promoters from CaM-Kinasell, Nestin, L7, BDNF, NV, MBP, NSE, beta-globin, GFAP, GAP43, tyrosine hydroxylase, Kainat-receptor-subunit 1, glutamate-receptor-subunit B, or human ubiquitin promoter B (ubiB human), human ferritin H promoter (FerH), etc. Particularly preferred promoters are of human or mammalian origin. Finally, synthetic promoters may be used advantageously. Promoter sequences, as contained in an inventive vector, may also be inducible for in vitro control purposes, to allow modulation of expression (e.g. by the presence or absence of nutrients or other inducers in the growth medium). One example is the lac operon obtained from bacteriophage lambda plac5, which can be induced by IPTG. Finally, a promoter as defined above may be linked with GLP-1 encoding nucleic acid sequence such that the promoter is positioned 5' "upstream" of the GLP-1 encoding nucleic acid sequence. Preferably, human promoters are used, e.g. the human ubiquitin promoter B (ubiB human) or the human ferritin H promoter (FerH).

Enhancer sequences for upregulating expression of GLP-1 encoding nucleic acid sequences are preferably another constituent of a vector as defined above. Such enhancer sequences are typically located in the non-coding 3' region of the vector. Enhancer sequences as employed in a vector as defined above may be obtained from any eukaryotic, prokaryotic, viral, bacterial, plant, human or animal, e.g. mammalian hosts, preferably in association with the corresponding promoters as defined above. Enhancer elements which will be most useful in the present invention are those which are glucose responsive, insulin responsive and/or liver specific. Enhancer elements may include the CMV enhancer (e.g., linked to the ubiquitin promoter (Cubi)); one or more glucose responsive elements, including the glucose responsive element (G1RE) of the liver pyruvate kinase (L-PK) promoter ($-172$ to $-142$); and modified versions with enhanced responsiveness (Cuif et al., supra; Lou, et al., J. Biol Chem, (1999). 274:28385-94); G1RE of L-PK with auxiliary L3 box ($-172$ to $-126$) (Diaz Guerra, et al., Mol Cell Biol, (1993). 13:7725-33; modified versions of G1RE with enhanced responsiveness with the auxiliary L3 box; carbohydrate responsive element (ChoRE) of S14 ($-1448$ to $-1422$), and modifications activated at lower glucose concentrations (Shih and Towle, J Biol Chem, (1994). 269:9380-7; Shih, et al., J Biol Chem, (1995). 270:21991-7; and Kaytor, et al., J Biol Chem, (1997). 272:7525-31; ChoRE with adjacent accessory factor site of S14 ($-1467$ to $-1422$) [et al., supra]; aldolase ($+1916$ to $+2329$) (Gregori et al., J Biol Chem, (1998). 273:25237-43; Sabourin, et al., J. Biol Chem, (1996). 271:3469-73; and fatty acid synthase ($-7382$ to $-6970$) (Rufo, et al., supra.), more preferably insulin responsive elements such as glucose-6-phosphatase insulin responsive element ($-780$ to $-722$) [Ayala et al., Diabetes, (1999), 48:1885-9; and liver specific enhancer elements, such as prothrombin (940 to $-860$) [Chow et al., J Biol Chem, (1991) 266: 18927-33; and alpha-1-microglobulin ($-2945$ to $-2539$) [Rouet et al., Biochem J, (1998). 334:577-84), Muscle-specific enhancers such as mammalian MCK enhancer, mammalian DES enhancer, and vertebrate troponin I IRE (TNI IRE, herein after referred to as FIRE) enhancer. Finally, a SV40 enhancer sequence may also be included.

Enhancer elements may further be used along with promoters as defined above. E.g. such promoter/enhancer combinations include e.g. the cytomegalovirus (CMV) promoter and the CMV enhancer, the CMV enhancer linked to the ubiquitin promoter (Cubi), the group of liver-specific enhancer elements comprising human serum albumin [HSA] enhancers, human prothrombin [HPrT] enhancers, alpha-1 microglobulin [A1MB] enhancers, and intronic aldolase enhancers used in combination with their corresponding promoters, or HSA enhancers used in combination with a promoter selected from the group of a CMV promoter or an HSA promoter, enhancer elements selected from the group consisting of human prothrombin [HPrT] and alpha-1 microglobulin [A1MB] used in combination with the CMV promoter enhancer elements selected from the group consisting of human prothrombin [HPrT] and alpha-1 microglobulin [A1MB] used in combination with the alpha-1-anti trypsin promoter, etc.

Furthermore, a vector as defined above suitable for transfecting a cell which may be used as constituent of the inventive spherical microcapsule, may contain transcriptional and/or translational signals, preferably transcriptional and/or translational signals recognized by an appropriate host, such as transcriptional regulatory and translational initiation signals. Transcriptional and/or translational signals may be obtained from any eukaryotic, prokaryotic, viral, bacterial, plant, preferably human or animal, e.g. mammalian hosts, preferably in association with the corresponding promoters as defined above. A wide variety of transcriptional and translational regulatory sequences may be employed therefore, depending upon the nature of the host. To the extent that the host cells recognizes the transcriptional regulatory and translational initiation signals associated with a GLP-1 encoding nucleic acid sequence, the 5' region adjacent to the naturally occurring GLP-1 encoding nucleic acid sequence may be retained and employed for transcriptional and translational regulation in an inventive vector. This region typically will include those sequences involved with initiation of transcription and translation, such as the TATA box, capping sequence, CAAT sequence, and the like. Typically, this region will be at least about 150 base pairs long, more typically about 200 bp, and rarely exceeding about 1 to 2 kb.

Transcriptional initiation regulatory signals may be selected that allow to control repression or activation such that expression of the genes can be modulated. One such controllable modulation technique is the use of regulatory signals that are temperature-sensitive in order to repress or initiate expression by changing the temperature. Another controllable modulation technique is the use of regulatory signals that are sensitive to certain chemicals. Transcription and/or translational signals also include transcriptional termination regulatory sequences, such as a stop signal and a polyadenylated region. Preferably, transcriptional termination regulatory sequences are located in the non-coding 3' region of a vector as defined above containing the GLP-1 encoding nucleic acid sequence. Suitable termination sequences include, for example, the bovine growth hormone, SV40, lacZ, EF1 alpha and AcMNPV polyhedral polyadenylation signals.

The expression vectors suitable for transfecting a cell which may be used for preparing the inventive spherical microcapsule may also include other sequences for optimal expression of GLP-1 peptides as defined herein. Such sequences include sequences encoding signal (peptide) sequences, i.e. which encode N-terminally located peptide sequences that provide for passage of the secreted protein into or through a membrane; sequences, which provide for stability of the expression product; and restriction enzyme recognition sequences, which provide sites for cleavage by restriction endonucleases. All of these materials are known in the art and are commercially available (see, for example, Okayama (1983), Mol. Cell, Biol., 3: 280).

As defined herein "a signal sequence" is a signal (peptide) sequence which typically comprises about 15 to 30 amino acids located at the N-terminus of the expressed GLP-1 (fusion) peptide and enables the GLP-1 peptide to be secreted, i.e. to pass through a cell membrane. Such a signal sequence may include the signal sequence normally associated with the wild type GLP-1 precursor protein (i.e., the signal sequence(s) of the full length proglucagon precursor molecule), as well as signal (peptide) sequences which are not normally associated thereto, i.e. heterologous to the wild type GLP-1 precursor protein (i.e., the signal sequence(s) of the full length proglucagon precursor molecule). A "signal sequence" as defined herein can be, for example, a signal peptide sequence or a leader sequence (e.g. a secretory signal (and leader) sequence). Furthermore, signal (peptide) sequences as defined herein preferably provide for cleavage of the (GLP-1) precursor peptide by a protease, e.g. a signal sequence protease. Upon cleavage of the signal sequence from the (GLP-1) precursor peptide by the protease a biologically active GLP-1 peptide as defined above is produced. Such a signal sequence generally comprises a region which encodes a cleavage site recognized by a protease for cleavage. Alternatively, a region which encodes a cleavage site recognized by a protease for cleavage can be introduced into the signal sequence. Furthermore, additional (one or more) sequences which encodes a cleavage site recognized by a protease for cleavage can be added to the signal sequence.

Examples of signal sequences which can be encoded by a vector as defined above include a signal sequence derived from a secreted protein such as GLP-1 or other than GLP-1, such as a cytokine, a clotting factor, an immunoglobulin, a secretory enzyme or a hormone (including the pituitary adenylate cyclase activating polypeptide (PACAP)/glucagon superfamily) and a serum protein. For example, a signal sequence as defined herein can be derived from secreted matrix metalloproteinases (MMP), e.g. a stromelysin leader sequence, from secreted human alkaline phosphatase (SEAP), pro-exendin, e.g. a proexendin-4 leader sequence, pro-helodermin, pro-glucose-dependent insulinotropic polypeptide (GIP) pro-insulin-like growth factor IGF1), preproglucagon, alpha-1 antitrypsin, insulin-like growth factor 1, human factor IX, human lymphotoxin A (Genbank Accession No. BAA00064), or human clusterin (Genbank Accession No. AAP88927). Particular examples of signal sequences as defined herein are sequences which include a coding region for a signal for precursor cleavage by signal peptidase, furin or other prohormone convertases (e.g., PC3). For example, a signal which is cleaved by furin (also known as PACE, see U.S. Pat. No. 5,460,950), other subtilisins (including PC2, PC1/PC3, PACE4, PC4, PC5/PC6, LPC/PC7IPC8/SPC7 and SKI-1; Nakayama, Biochem. J., 327; 625-635(1997)); enterokinase (see U.S. Pat. No. 5,270,181) or chymotrypsin can be introduced into the signal sequence as defined herein. The disclosure of each of the above documents is hereby incorporated herein by reference. Furin is a ubiquitously expressed protease that resides in the trans-golgi and processes protein precursors before their secretion. Furin cleaves at the COOH-terminus of its consensus recognition sequence, Arg-X-Lys-Arg or Arg-X-Arg-Arg, (Lys/Arg)-Arg-X-(Lys/Arg)-Arg and Arg-X-X-Arg, such as an Arg-Gln-Lys-Arg (SEQ ID NO: 27). These amino acid sequences are a signal for precursor cleavage by the protease furin. Thus, a heterologous signal sequence can also be synthetically derived from a consensus sequence compiled from signal sequences (e.g., a consensus sequence compiled from secreted proteins that are cleaved by signal peptidase).

Additionally to regulation sequences as defined above, an autonomously replicating vector as define above typically comprises an origin of replication. Suitable origins of replication include, without being limited thereto, e.g. ColE1, pSC101, SV40, pMPI (ori pMPI) and M13 origins of replication, etc.

Preferably, a vector as defined above may additionally contain a suicide gene. In the context of the present invention "a suicide gene" is preferably capable to stop the therapy with inventive spherical microcapsules by killing the suicide gene harboring cell contained in the core of the inventive microcapsule upon administering a specific substance. E.g. a suicide gene suitable for the present invention may be activated by administering an exogenous activator that typically does not occur in the human or animal body. In this case, typically the suicide gene initiates a cascade causing the cell to undergo an apoptotic event. Alternatively, a suicide gene suitable for the present invention may metabolize an administered exogenous non-toxic prodrug that typically does not occur in the human or animal body. Metabolization of the exogenous non-toxic prodrug preferably renders the prodrug to a cell toxin. The suicide gene may be contained on the same vector encoding the GLP-1 peptide as defined above or alternatively on a second vector. Furthermore, the suicide gene may be regulated by control and regulatory elements of any kind, e.g. control and regulatory elements such as promoters, enhancers, etc. as mentioned herein as constituents expression vectors, or by their naturally occurring control and regulatory elements. Preferably, suicide genes are selected according to the present invention, which allow any of the above control mechanisms, e.g. suicide genes selected from cytosin deaminase (CD), uracil phosphoribosyl transferase (UPRTase), HSV thymidine kinase (HSV-Tk), suicide genes which may be induced by addition of tetracycline such as the bacterial Tet repressor protein (TetR), etc. As a particular example the cytosine desaminase (CD) may be used. The cytosine desaminase (CD) typically occurs in a variety of organisms and is capable of transforming 5-fluorocytosin (5-FC) into 5-fluorouracil (5-FU), which represents a common chemotherapeutical agent. 5-fluorouracil (5-FU) is highly toxic for the organism whereas its prodrug 5-fluorocytosin (5-FC) is not toxic to cells. 5-fluorouracil (5-FU) is subsequently phosphorylated by cellular kinases and is capable of abrogating the cells RNA synthesis. Thus, the prodrug 5-fluorocytosin (5-FC) represents an excellent tool for inducing suicide of a specific cell. Furthermore, 5-Fluoro-dUMP acts as antifolate agent and inhibits the enzyme thymidylat synthase, which catalyses methylation of dUMP to dTMP in the de novo synthesis path of desoxyribonukleotides. Thereby, inhibition of DNA synthesis in the cell may be inhibited. Also preferably, the HSV-1 thymidin kinase (ATP: Thymidin-5-phosphotransferase) and its corresponding prodrug ganciclovir (GCV) may be used. The guanosin analog GCV is specifically phosphorylated and inhibits elongation of DNA synthesis and thus leads to suicide of the cell.

Transfection of the vectors as defined above or, alternatively, of naked (GLP-1 peptide encoding nucleic acids into suitable cells used for preparation of inventive microcapsules, may be accomplished by any method known to a skilled person (see e.g. Maniatis et al. (2001) Molecular Cloning: A laboratory manual, Cold Spring Harbor Laboratory Press, Cold Spring Harbor, N.Y.). If vectors are transfected into suitable cells as defined above, the vector is preferably present in the form of a plasmid DNA, which carries a GLP-1 peptide encoding nucleic acid. The plasmid DNA is preferably a circular plasmid DNA. Suitable transfection methods include, without being limited thereto, e.g. electroporation techniques including modified electroporation techniques (e.g. nucleofection), calcium phosphate techniques, e.g. the calcium phosphate co-precipitation method, the DEAE-Dextran method, the lipofection method, e.g. the transferring-mediated lipofection method, etc. Preferably, transfection is carried out with plasmid DNA carrying a vector as defined above using a modified electroporation technique ('e.g. nucleofection).

In an alternative embodiment of the invention, the GLP-1 (fusion) peptide as defined herein and as secreted from cells embedded in the inventive spherical microcapsules contains as component (I) and/or (III) a modified GLP-1 peptide comprising the amino acid sequence of the following formula II:

```
                                        (SEQ ID NO: 28)
Xaa7-Xaa8-Glu-Gly-Thr-Phe-Thr-Ser-Asp-Xaa16-Ser-

Xaa18-Xaa19-Xaa20-Glu-Xaa22-Xaa23-Ala-Xaa25-Xaa26-

Xaa27-Phe-Ile-Xaa30-Trp-Leu-Xaa33-Xaa34-Xaa35-

Xaa36-Xaa37,
``` wherein Xaa7 is L-histidine, D-histidine, desamino-histidine, 2-amino-histidine, 3-hydroxy-histidine, homohistidine, N-acetyl-histidine, α-fluoromethyl-histidine, a-methyl-histidine, 3-pyridylalanine, 2-pyridylalanine or 4-pyridylalanine; Xaa8 is Ala, Gly, Val, Len, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid, whereby Gly is particularly preferred; Xaa16 is Val or Leu; Xaa18 is Ser, Lys or Arg; Xaa19 is Tyr or Gln; Xaa20 is Leu or Met; Xaa22 is Gly, Glu or Aib; Xaa23 is Gln, Glu, Lys or Arg; Xaa25 is Ala or Val; Xaa26 is Lys, Glu or Arg; Xaa27 is Glu or Leu; Xaa30 is Ala, Glu or Arg; Xaa33 is Val or Lys; Xaa34 is Lys, Glu, Asn or Arg; Xaa35 is Gly or Aib; Xaa36 is Arg, Gly or Lys or amide or absent; Xaa37 is Gly, Ala, Glu, Pro, Lys, amide or is absent.

In still another embodiment of the invention component (I) and/or (III) of the GLP-1 (fusion) peptide as used for the inventive microcapsules contains a modified GLP-1 peptide comprising the amino acid sequence of the following formula III:

```
                                        (SEQ ID NO: 29)
Xaa7-Xaa8-Glu-Gly-Thr-Phe-Thr-Ser-Asp-Val-Ser-

Xaa18-Tyr-Leu-Glu-Xaa22-Xaa23-Ala-Ala-Xaa26-Glu-

Phe-Ile-Xaa30-Trp-Leu-Val-Xaa34-Xaa35-Xaa36-Xaa37,
``` wherein Xaa7 is L-histidine, D-histidine, desamino-histidine, 2-amino-histidine, 3-hydroxy-histidine, homohistidine, N-acetyl-histidine, a-fluoromethyl-histidine, a-methyl-histidine, 3-pyridylalanine, 2-pyridylalanine or 4-pyridylalanine; Xaa8 is Ala, Gly, Val, Len, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid; Xaa18 is Ser, Lys or Arg; Xaa22 is Gly, Gln or Aib; Xaa23 is Gln, Gln, Lys or Arg; Xaa26 is Lys, Glu or Arg; Xaa30 is Ala, Glu or Arg; Xaa34 is Lys, Glu or Arg; Xaa35 is Gly or Aib; Xaa36 is Arg or Lys, amide or is absent; Xaa37 is Gly, Ala, Glu or Lys, amide or is absent.

In a particular preferred embodiment the spherical microcapsule of the invention contains a GLP-1 (fusion) peptide, component (I) and/or (III) of which contain a (modified) GLP-1 peptide, which is selected from GLP-1 (7-35), GLP-1 (7-36), GLP-1 (7-36)-amide, GLP-1 (7-37) or an variant, analogue or derivative thereof. Also preferred are GLP-1 (fusion) peptides comprising in their components (I) and/or (III) a modified GLP-1 peptide having a Aib residue in position 8 or an amino acid residue in position 7 of said GLP-1 peptide, which is selected from the group consisting of D-histidine, desamino-histidine, 2-amino-histidine, hydroxy-histidine, homohistidine, N-acetyl-histidine, a-fluoromethyl-histidine, a-methyl-histidine, 3-pyridylalanine, 2-pyridylalanine and 4-pyridylalanine.

Both embodiments of components (I) and/or (III) of the GLP-1 (fusion) peptide as defined above by formulae II and III and usable for the present invention may be combined with the disclosure given above for GLP-1 (fusion) peptide. In other words, general formulae II and III may be combined e.g. with the disclosure given above for component (II), linkers, process of manufacturing etc.

Furthermore, the GLP-1 (fusion) peptide expressed and secreted by the cells embedded in the core of the inventive microcapsule may preferably contain at least one synthetic polymer or a natural polymer, e.g. polyamino acids. The at least one polymer constituent is typically covalently coupled to the fission peptide subunit. "Conjugated" in the meaning of the present invention is intended to mean "chemically coupled". "Chemically coupled" is intended to mean coupled via covalent or non-covalent bondings. While covalent bonding is preferred, the polymer constituent may also be linked to the fusion peptide via complexation without covalent linkage, e.g. via hydrogen bonding or electrostatic, hydrophobic, etc. interaction. The entire complex containing the fusion peptide and the polymer is termed hereinafter "GLP-1 conjugate complex" or "GLP-1 conjugate molecule".

Thereby, the GLP-1 conjugate molecule is even further protected against the proteolytic degradation in vivo, mainly due to proteolytic endopeptidase IV activity. The conjugate complex having or comprising a GLP-1 (fusion) peptide of at least two components (I) and (II) and the synthetic polymer exhibits GLP-1's biologically activity and, simultaneously, confers stability to the GLP-1 as its component (I) by a C-terminal elongation. Accordingly, by conjugating the fusion peptide to a polymer its in vivo stabilisation is increased considerably.

The polymer used herein can be a physiologically acceptable polymer which includes polymers which are soluble in an aqueous solution or suspension and have no negative impact, such as side effects, to mammals upon administration of the fusion peptide in a pharmaceutically effective amount. There is no particular limitation to the physiologically acceptable polymer used according to the present invention. The polymer may be of synthetic nature or may be naturally occurring polymer (natural polymer, e.g. a protein).

One, two, or three polymer constituents may be covalently attached to the fusion peptide subunit, with one polymer constituent being preferred, to form the GLP-1 conjugate molecule. However.

in specific embodiments more than three polymer constituents may be provided per fusion peptide subunit. The constituents may be covalently coupled to either component or component (II) of the fusion peptide or both of them. It is preferred to couple at least one of the polymer constituents to component (II). If one or more polymer constituent(s) is/are coupled to component (I) it/they is/are preferred to be coupled to the N-terminus or to the side chains of serine, threonine, tyrosine, aspartate, glutamate, lysine car arginine residues. Preferably, the side chains of one or more of residues Thr 11, Thy 13, Asp 15, Ser 17, Ser 18, Tyr 19, Gln 21, Lys 26, Glu 27, Lys 34, Arg 36 of component (I) are used for coupling purposes. If the naturally occurring sequence of IP2 is used as component (II) one or more of its Arg, Glu and Asp residues will modified at their side chains by a polymer constituent(s).

The N-terminal binding of a polymer, in particular PEG, may offer advantages in purification of the conjugate molecule. It is also believed that the N-terminal binding of a polymer may better preserve the bioactivity compared with random polymer binding to any other residue, e.g. any other lysine residue. Accordingly, in a preferred embodiment, at least one polymer constituent is located at the N-terminus of the fusion peptide. If PEGylation is used, PEGylation of terminal or side chain carboxyl groups or the epsilon-amino group of lysine occurring in the inventive peptide, confers resistance to oxidation and is also within the scope of the present invention.

More generally, the synthetic polymer of a GLP-1 (fusion) peptide as used in the core of the inventive spherical microcapsule is preferably selected from alkylene glycols, such as polyethylene glycol (PEG), polypropylene glycol (PPG), copolymers of ethylene glycol and propylene glycol, polyoxyethylated polyol, polyolefinic alcohol, polyvinylpyrrolidone, polyhydroxyalkyl methacrylamide, polyhydroxyalkyl methacrylate, such as polyhydroxyethylen methycrylate, polyacrylate, polysaccharides, poly([alpha]-hydroxy acid), polyvinyl alcohol, polyphosphazene, polyoxazoline, poly(N-acryloylmorpholine), polyvinylethyl ether, polyvinlyacetale, polylactic glycolic acid, polylactic acid, lipid polymer, chitin, hyaluronuic acid, polyurethyne, polysialic acid cellulose triacetat, cellulose nitrate and combinations of any of the foregoing. Preferably natural polymers are peptide or proteins linked via side chains to the (GLP-1 (fusion) peptide or via terminal groups (amino and/or carboxy), preferably albumin and transferrin.

Inventive spherical microcapsules as defined above are preferably prepared according to two or more method steps. According to a method step 1) a core is prepared as disclosed above. According to a method step 2) the core as prepared according to method step 1) is encased by a surface coating. Further optional steps comprise preparation of additional surface coatings. Preferably, a step identical to method step 2) is carried out for each additional surface coating. Further optional steps may include washing steps.

Typically, a core as disclosed above is prepared according to method step 1) for preparing inventive spherical microcapsules. Such a core is composed of cross-linked polymer and GLP-1 expressing and secreting cells, which have been transfected according to a method as disclosed above. According to method step 1), a mixture (suspension) of the soluble form of the polymer, e.g. the soluble form of an alginate (e.g. calcium or sodium alginate in physiological saline solution), and of GLP-1-peptide expressing and secreting cells is typically prepared, preferably in a concentration of up to $5*10^7$ cells per ml polymer solution.

The homogenic cell/polymer suspension (e.g. cell/alginate suspension) is typically pressed via an air injected spray nozzle, consisting of three channels, which are arranged concentrically as three concentric rings around a common center: an inner channel, an intermediate channel and an outer channel (air ring). Preferably hollow needles are used for the inner channel having an inner diameter of 50 μm up to 2,000 μm. The intermediate channel typically has an inner diameter of 60 μm to 4,000 μm, and the outer channel (air ring) preferably has an inner diameter of 100 μm to 5,000 μm, Exclusively the inner channel and the outer channel (air ring) are used in method step 1) for preparing the core of the inventive microcapsule. Thus, a spray nozzle merely consisting of two channels (an inner and an outer channel) may be used in method step 1) as well. Typically, no material flows through the intermediate channel, an air injected spray nozzle with three channels is used. The suspension of the cell/polymer solution is typically pressed with a speed of 10 μl/min to 5 ml/min through the inner channel leading to droplets at the outlet of the channel, which tear off due to the air flow provided by the outer channel (air ring), having a speed of typically 0.5 l/min to 10 l/min. Droplets containing cells and non-cross-linked polymer solution fall down into a cross-linker containing solution (precipitation bath), which is typically positioned in a distance of about 4 cm to about 60 cm tinder the outlet of the air injected spray nozzle. The droplet preferably rounds during dropping down, thereby receiving a substantially spherical geometrical Corm. The cross-linker effects ionical cross-linking of the polymers and the core of the inventive spherical (water insoluble) microcapsule is initially formed having a diameter of about 20 μm to about 4,000 μm. The diameter of the core of the inventive spherical microcapsule is dependent on size and geometry of the chosen channels used in method step 1). The cross-linker containing solution (precipitation bath) is preferably composed of bivalent cations, e.g. calcium or barium ions (5-100 mM) or other bivalent or multivalent cations, if alginates are used as polymers. Furthermore, the precipitation bath preferably contains a buffer substance (e.g. 1 mM-10 mM histidine) and sodium chloride (e.g. 290 mOsmol±50 mOsmol). Other suitable cross-linkers and buffers known in the art may be used herein, if other polymers than alginates are used.

Method step 1) provides the core of the inventive microcapsule composed of cross-linked polymers and cells. Subsequent to method step 1) optional method step(s) may include a washing step. The core of the inventive spherical microcapsule is e.g. washed with a physiological saline solution or any other suitable washing solution and, if applicable, the core is incubated in a sodium sulfate solution, preferably in a sodium sulfate solution according to U.S. Pat. No. 6,092,880, the disclosure of which is incorporated herein by reference. Separation of the cores of the inventive spherical microcapsules from the precipitation bath and/or the washing bath is typically is carried out using a centrifuge or any other suitable method.

According to method step 2) the core of the inventive spherical microcapsule prepared by method step 1) is coated with a surface coating substantially of cross-linked polymer. Accordingly, the core of the inventive spherical microcapsule, prepared by step 1), is added to a polymer solution containing non-crosslinked polymers as disclosed above comprising no cells. Preferably, the polymers are provided in their non-cross-linked form in a concentration as defined above. Typically, this mixture containing the polymer solution and the core of the inventive spherical microcapsule is pressed through the inner channel of the above-described air injected spray nozzle, e.g. with a speed of 15 μl/min to 2 ml/min, preferably 10 μl/min to 5 ml/min. Simultaneously, a pure non-cross-linked polymer solution without cells, preferably a solution comprising about 0.1% to about 4% (w/v) polymer, e.g. an alginate solution without any cells, is pressed through the intermediate channel with a speed of typically 15 μl/min to 2 ml/min, preferably 10 μl/min to 5 ml/min. Thereby, droplets are formed at the end of the intermediate channel, containing the core and a surface of non-polymerized polymer. These droplets tear off due to the air flow provided via the outer channel (air ring) having a speed of typically 0.5 l/min to 10 l/min. The polymer concentration of the core of the inventive spherical microcapsule, the polymer solution, into which the core of the inventive microcapsules is added, and the polymer concentration of the surface coating may differ (see above). The droplets containing the core of the inventive spherical microcapsules (prepared according to method step 2)) fall into a solution containing the cross-linker (precipitation bath) as defined above. During dropping down, the droplet preferably rounds to an approximately spherical geometrical form. The cross-linker effects a ionic cross-linkage of the polymers analogous to method step 1). Thereby, water insoluble spherical microcapsules are formed having a diameter of 60 μm to 4,000 μm. The diameter of inventive spherical microcapsules obtainable by method step 2) are dependent from size and geometry of the chosen channels, as used herein. In order to prepare inventive microcapsules with more than one surface coating, i.e. inventive spherical microcapsules containing the core as defined above and 2, 3, 4, 5, 5-10 or more surface coatings, method step 2) may be repeated as often as necessary.

Subsequent to method step 2) one or more optional washing steps may follow as defined above.

According to a further aspect of the invention a method of treatment of an animal is provided, preferably a human being, by administration of an inventive spherical microcapsule. The invention encompasses use of such inventive spherical microcapsules for the manufacture of a product, e.g. for preparation of a pharmaceutical composition or a kit. Preferably, an inventive spherical microcapsule is used (for preparation of a pharmaceutical composition) for the treatment or prevention of a disease or condition associated with glucose metabolism. Non-limiting examples of glucose disorders include e.g. diabetes mellitus type I or type II (NIDDM), or insulin resistance, weight disorders and diseases or conditions associated thereto, wherein such weight disorders or associated conditions include obesity, overweight-associated conditions, satiety deregulation, reduced plasma insulin levels, increased blood glucose levels, or reduced pancreatic beta cell mass. Preferably, use of inventive spherical microcapsules (for the preparation of a pharmaceutical composition) for the treatment of type 2 diabetes (NIDDM) is disclosed herewith. As a consequence, the present invention refers to the use of the inventive spherical microcapsules (for the preparation of a pharmaceutical composition) e.g. for lowering weight of a subject, for reducing satiety of a subject, for post-prandially increasing plasma insulin levels in a subject, for reducing fasting blood glucose level in a subject, for increasing pancreatic beta cell mass in a subject or for treating diabetes type I or II in a subject.

Patients with other diseases or disorders may also be treated with inventive spherical microcapsules as well. Inventive spherical microcapsules may be used (for the preparation of a pharmaceutical composition) for the treatment of neurodegenerative disorders and diseases or conditions associated thereto and (for the preparation of a pharmaceutical composition) for the treatment of disorders and diseases or conditions associated to apoptosis. The use of the inventive spherical microcapsules having cells embedded to its core expressing and secreting GLP-1 (for the preparation of a pharmaceutical composition) for treating these disorder results from the following; GLP-1 receptors, which are coupled to the cyclic AMP second messenger pathway, are expressed throughout the brains of rodents and humans. The chemoarchitecture of receptor distribution in the brain does not only correlate with a central role for GLP-1 in the regulation of food intake and response to aversive stress. It was also shown that GLP-1 binding at its GLP-1 receptor exerts neurotrophic properties, and offers protection against glutamate-induced apoptosis and oxidative injury in cultured neuronal cells. Furthermore, GLP-1 was shown to modify processing of the amyloid β-protein precursor in cell culture and dose-dependently reduces amyloid β-peptide levels in the brain in vivo. GLP-1 is therefore also known as regulator of the central nervous system. GLP-1 peptides mimicking the biological activity of physiologically active GLP-1 have therapeutic relevance to the treatment of e.g. Alzheimer's disease (AD) and other central and peripheral neurodegenerative conditions e.g. amyotrophic lateral sclerosis (ALS), Alexander disease, Alper's disease, Ataxia telangiectasia, Canavan disease, Cockayne syndrome, Creutzfeldt-Jakob disease, Multiple Sclerosis, Sandhoff disease, Pick's disease, Spinocerebellar Ataxia, Schilder's disease and Parkinson's disease, as well as stroke, intracerebral haemorrhage (ICH), subarachnoid haemorrhage, adenoleukodystrophy (x-ALD) or other leukodystrophies, etc.

Moreover, it was shown that physiologically active GLP-1 exerts anti-apoptotic action on various cells, e.g. GLP-1 is beneficial to the preservation of mass and function of freshly isolated human islets or other cell types. Insofar, the inventive spherical microcapsules (expressing and secreting biologically active GLP-1 peptide) may be used to treat disorders, which are caused by cell or tissue apoptosis.

Another aspect of the present invention is a pharmaceutical composition containing inventive spherical microcapsules, which may be administered exogenously. Such a pharmaceutical composition may be applied to a patient suffering from the above disorders.

Preparation of pharmaceutical compositions which contain inventive spherical microcapsules as an "active ingredient", is generally well understood in the art, as e.g. exemplified by U.S. Pat. Nos. 4,608,251; 4,601,903; 4,599,231; 4,599,230; 4,596,792; and 4,578,770, all incorporated herein by reference.

The inventive pharmaceutical composition for the inventive spherical microcapsules) may be administered exogenously to a patient. Typical administration forms include, without being limited thereto, parenteral administration, e.g. by injection, for example, either subcutaneously, intradermally, subdermally, intramuscularly, or via intravenous, cutaneous or subcutaneous injection at the site of affliction. Other modes of administration, which may be suitable for treatment of any of the afore mentioned diseases or disorders, include transplantation of the inventive pharmaceutical composition or the inventive spherical microcapsules (preferably formulated in a suitable form, e.g. by addition of suitable pharmaceutical carriers, e.g. in the form of gels, capsules, tablettes, etc.). An inventive pharmaceutical composition for parenteral administration may, for example, be prepared as described in WO 03/002136, the disclosure of which is incorporated herein by reference.

Sites of administration suitable for the present invention include tissues of the patient to be treated, e.g. fat tissue, brain, liver, muscles, etc. as well as body liquids, e.g. blood, lymph, brain liquid, etc. Devices suitable thr administration of the inventive pharmaceutical composition include any device suitable for the selected administration mode and may be selected by a person skilled in the art. Without being limited thereto, the inventive pharmaceutical composition may be administered e.g. via injection by applying an appropriate injection needle such as injection needles having a size of from 12 to 26 G, more preferably of from 18 to 22 G or e.g. by transplanting the inventive pharmaceutical composition, preferably formulated in a suitable form, using surgical devices, such as scalpels, injection needles as defined above, etc. According to a particular example, which shall not be regarded as limiting to the present embodiment, a patient in need thereof, suffering from type 2 diabetes or any disease associated thereto or disclosed herein may receive a subcutaneous injection or implantation of the inventive pharmaceutical composition (containing inventive spherical microcapsules) into his fat tissue, etc. Such inventive pharmaceutical composition containing inventive spherical microcapsules may contain cells as defined above, e.g. selected from human mesenchymal stem cells differentiating in vivo or in vitro into adipocytes. Furthermore, a patient suffering from a neurodegenerative disease as defined herein, may receive an implantation of the inventive pharmaceutical composition into his brain tissue, e.g. into brain parenchyma etc.

Typically, pharmaceutical compositions are prepared as injectables either as liquid solutions or suspensions, preferably containing water (aqueous formulation) or may be emulsified. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

For intravenous, cutaneous or subcutaneous injection, or injection at the site of affliction, the inventive pharmaceutical compositions will be in the form of a parenterally acceptable aqueous solution which is pyrogen-free and has suitable pH, isotonicity and stability. Liquid pharmaceutical compositions generally include a liquid vehicle such as water. Preferably, the liquid vehicle will include a physiological saline solution, dextrose ethanol or other saccharide solution or glycols such as ethylene glycol, propylene glycol or polyethylene glycol or combinations thereof may be included. Further examples include other isotonic vehicles such as physiological salt solutions, e.g. Ringers solution or Lactated Ringer's solution.

If the inventive pharmaceutical composition comprises an aqueous solution of an inventive spherical microcapsule, and e.g. a buffer, said inventive spherical microcapsule is typically present in the pharmaceutical composition in a concentration from 0.1 mg/ml or above, and said pharmaceutical composition usually has a pH from about 2.0 to about 10.0, preferably from about 7.0 to about 8.5.

It is possible that other ingredients may be present in the inventive pharmaceutical composition. Such additional ingredients may include wetting agents, emulsifiers, antioxidants, bulking agents, pH buffering agents (e.g. phosphate or citrate or maleate buffers), preservatives, surfactants, stabilizers, tonicity modifiers, cheating agents, metal ions, oleaginous vehicles, proteins (e.g. human serum albumin, gelatin or proteins) and/or a zwitterion (e.g. an amino acid such as betaine, taurine, arginine, glycine, lysine and histidine). Such ingredients are selected by a skilled person according to the specific requirements of the cells embedded in the core of the inventive spherical microcapsule, i.e. the ingredients are not cytotoxic and ensure viability of the cells. Furthermore, such ingredients may stabilize GLP-1 peptides already expressed and secreted by the cells embedded in the core of the inventive spherical microcapsule.

With regard to buffers these are preferably selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethane, hepes, bicine, tricine, malic acid, succinate, maleic acid, fumaric acid, tartaric acid, aspartic acid or mixtures thereof. Each one of these specific buffers constitutes an alternative embodiment of the invention.

The use of all of the afore-mentioned additives in pharmaceutical compositions containing the inventive spherical microcapsule is well-known to the skilled person, in particular with regard to concentration ranges of the same. For convenience reference is made to Remington: The Science and Practice of Pharmacy, 19$^{th}$ edition, 1995.

Inventive pharmaceutical compositions containing the inventive spherical microcapsules are preferably administered in a manner compatible with the dosage formulation, and in such amount as will be therapeutically effective. The quantity of inventive spherical microcapsules to be administered with an inventive pharmaceutical composition (or, if required, alone), depends on the subject and the disease to be treated, including, e.g., the severity of the patient's disease. Suitable dosage ranges depend on the amount of biologically active GLP-1 peptide secreted by the inventive spherical microcapsules (as contained in the inventive pharmaceutical composition) during a predetermined time period and typically range in the order of one to several hundred micrograms per day. Typically, inventive spherical microcapsules as contained in the inventive pharmaceutical composition secrete about 0.5 µg GLP-1 per day per ml of inventive spherical microcapsules. Thus, a dosage range may be e.g. in the range from about 0.01 µg to 20 mg of secreted biologically active GLP-1 peptide per day (even though higher amounts in the range of 1-100 mg are also contemplated), such as in the range from about 0.01 µg to 10 mg per day, preferably in the range from 0.01 µg to 5 mg per day and even more preferably in the range from about 0.01 µg to 1 mg per day and most preferably in the range from about 0.01 µg to 500 µg per day.

DESCRIPTION OF FIGURES

FIGS. 4, 5: describe plasma stability tests (in vitro) carried out with GLP-1 peptides as used according to the present invention. Therefore, HEK293 and hTERT-MSC cells were transiently transfected with constructs GLP-1 (7-37) (1), GLP-1 (7-37)-IP2-extended with 11 AA (2) and GLP1 (7-37)-IP2-GLP 1(7-37) (3). The results are shown in FIG. 4 (HEK293 cells) and FIG. 5 (hTERT-MSC cells). HEK293 and hTERT-MSC cells are both effective hosts for the gene construct (see also Example 4).

FIG. 13; AtT20 cells: FIG. 14; or HEK293 cells: FIG. 15) and the clone number. The results show that the constructs of GLP-1/C terminal peptide are secreted from the transfected cell lines, i.e. the protein has the expected molecular weight. Additionally, it binds to anti-GLP-1 antibody which binds to the N terminal end of GLP-1 (7-37).

FIG. 13A: Secretion of GLP-1 from hTERT-MSC cell lines (1: 100 ng synthetic GLP-1$_{(7-37)}$ dissolved in supernatant of mock transfected hTERT-MSC cells, 2: supernatant of GLP$^{CM1}$ secreting hTERT-MSC cells (clone 79TM217/13), M: prestained protein marker [kDa])

FIG. 13B: Secretion of GLP-1 from hTERT-MSC cell lines (M: prestained protein marker [kDa], 1: 100 ng synthetic GLP1$_{7-37}$ dissolved in hTERT-MSC medium, 2: supernatant of analog GLP$^{CM1(G8)}$ secreting hTERT-MSC cells (clone 78TM216/2), 3: supernatant of GLP$^{CM1}$ secreting hTERT-MSC cells (clone 79TM217/13))

FIG. 14: GLP1 secreted from AtT20 cellines (1: supernatant of analog GLP$^{CM1(G8)}$ secreting AtT20 cells (clone 80-A-216/1), 2: supernatant of wildtype GLP$^{CM1}$ secreting AtT20 cells (clone 81-A-217/3))

FIG. 15: GLP1 secreted from transiently transfected HEK293 cells (1: supernatant of HEK293 cells transiently transfected with a Stromelysin-GLP1$_{7-37}$ construct (#103), 2: supernatant of HEK293 cells transiently transfected with a Stromelysin-GLP1$_{7-37}$-IP2-extended with 11 AA construct (#317), 3: supernatant of HEK293 cells transiently transfected with a Stromelysin-GLP1$^{CM1}$ construct (#217), 4: supernatant of HEK293 cells transiently transfected with a Stromelysin-GLP1$_{7-37}$-IP2 (4×) construct (#159))

Figure 18:
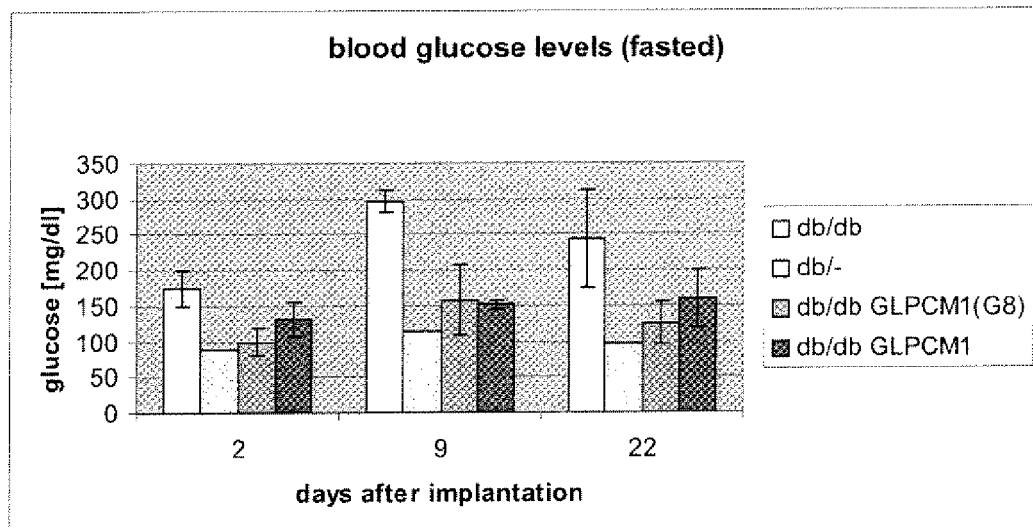

animal 7-10: db/db mice, treated with GLP1$^{CM1}$ secreting CellBead implants animal 13, 15: db/db mice, treated with a CellBead implant (without GLP1 secretion), animal db/–: non diabetic control mice, untreated;

FIG. 18: shows fasted blood glucose levels in diabetic C57/Ks-RJ db/db mice (db/db n=3) a non-diabetic heterozygous littermate (db/–n=1) and diabetic C57/Ks-RJ db/db mice treated with inventive spherical microcapsules (GLP-1 CellBeads) secreting GLPCMI (G8) (SEQ ID NO: 6 but with second residue G) (n=3) or GLPCM1 (SEQ ID NO: 6) (n=3), measured 2, 9 and 22 days after implantation.

Figure 19:
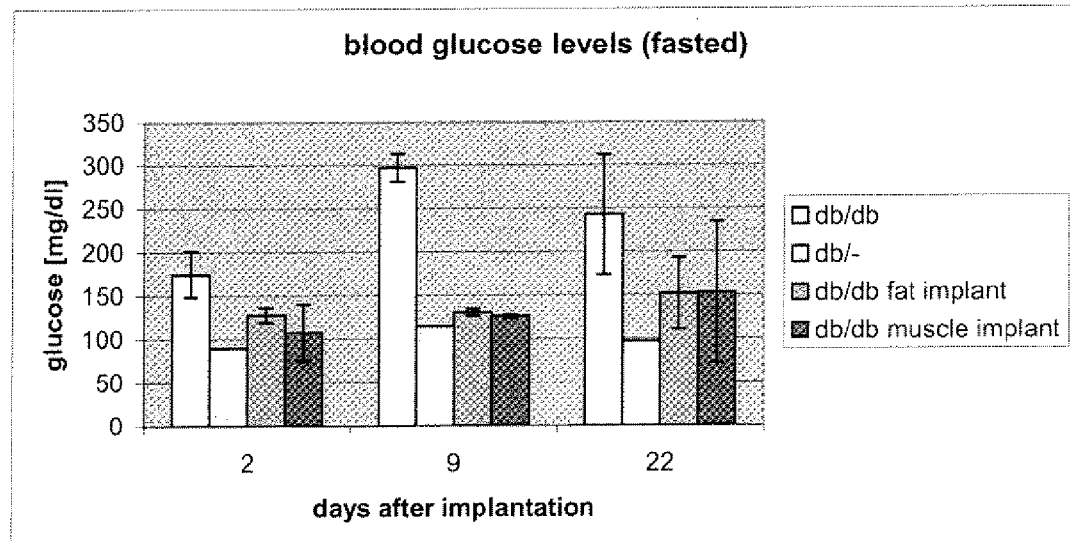

FIG. 19: depicts fasted blood glucose levels in diabetic C57/Ks-RJ db/db mice (db/db n=3), a non-diabetic heterozygous littermate (db/–n=1) and diabetic C57/Ks-RJ db/db mice treated with GLP$^{CM1(G8)}$ secreting inventive spherical microcapsules (CellBeads) implanted into the fat pad of the neck (n=2) or muscle (n=2), measured 2, 9 and 22 days after implantation.

Figure 20:
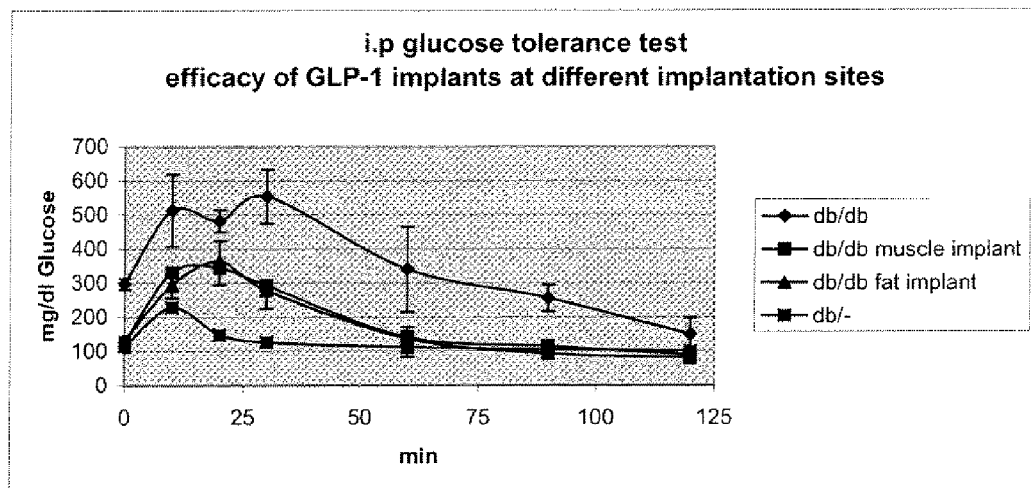

FIG. 20: illustrate IPGTT (i.p glucose tolerance tests). Overnight fasted mice received an i.p injection of a 20% glucose solution (1 mg glucose per g body weight). Measurement of blood glucose was performed before injection and in the following 2 h. FIG. 20 shows IPGTT for 14 week old diabetic C57/Ks-RJ db/db mice (db/db n=3), a non-diabetic heterozygous littermate (db/–n=1) and diabetic C57/Ks-RJ db/db mice treated with GLP$^{CM1(G8)}$ secreting inventive spherical microcapsules (CellBeads) implanted into the fat pad of the neck (n=2) or muscle (n=2) 9 days before the testing.

The invention is illustrated further in the accompanying examples. However, it is not intended to limit the scope of the invention to the content of the Examples as shown in the following.

EXAMPLES

Example 1

Creation of Genetic Constructs

Figure 1:
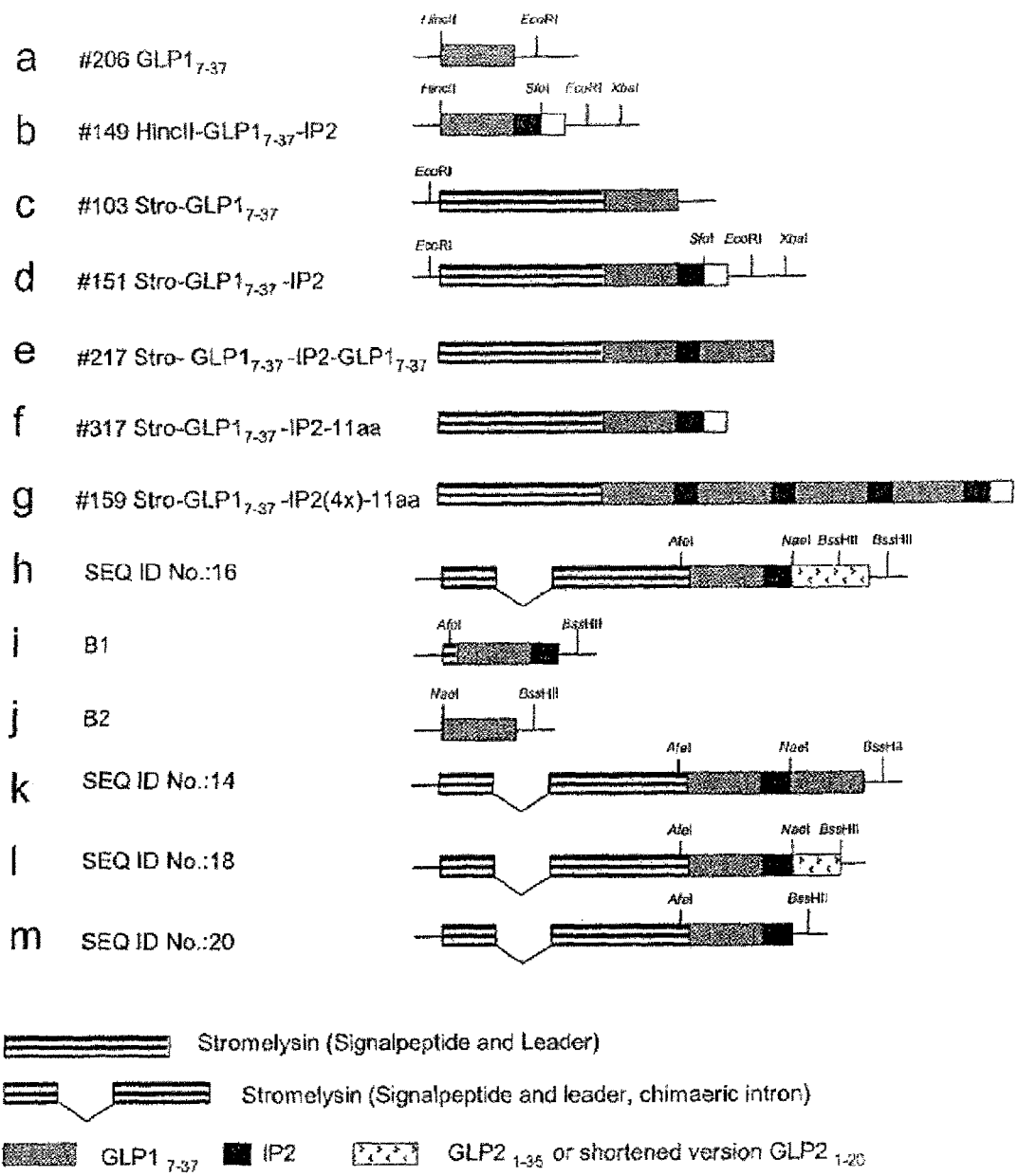
FIG. 1: shows a non-limiting overview over exemplary constructs a-m (see also Example 1), which may be contained in cells used for preparation of the inventive spherical microcapsules.

The coding sequence for GLP-1 (7-37) cDNA was synthesized synthetically, in a sequence including HincII and EcoRI sites as indicated in FIG. 1a. Separately the cDNA illustrated in FIG. 1b was synthesized, including the coding sequences for GLP-1 (7-37), IP2 and restriction sites for SfoI, EcoRI and XbaI, as illustrated in FIG. 1b. To direct GLP-1 to the secretory pathway, the heterologous signal sequence of stromelysin 3 (Acc. No. NM_005940) was used. Therefore the cDNA, encoding stromelysin signal and leader sequence was reverse transcriptase PCR amplified from human RNA, and used with the construct of FIG. 1a or FIG. 1b to form the construct shown in FIG. 1c and FIG. 1d, respectively.

The HincII/EcoRI fragment of the FIG. 1a construct is cloned into the SfoI site of the sequence of 1d to form the construct FIG. 1e. Similarly, the EcoRI fragment of FIG. 1d is cloned into the EcoRI site of an eukaryotic expression plasmid, to produce the construct shown in FIG. 1f. To form the construct shown in FIG. 1g, the HincII/XbaI fragment of the construct shown in FIG. 1b is repetitively cloned into the SfoI/XbaI site of the construct shown in FIG. 1d. FIG. 1h shows a synthesized, codon optimized sequence encoding the stromelysin leader and signal sequences interrupted by a shortened endogenous intron sequence, fused to sequences encoding human GLP-1 (7-37), IP2 and GLP-2 (1-35). The DNA sequence of the construct FIG. 1h is SEQ ID NO: 16, while SEQ ID NO: 15 also shows the sequence of the translated peptide.

Also synthesized are the sequences in FIGS. 1i and 1j. These are then used to form the construct in FIG. 1k, be cloning the NaeI/BssHII fragment of FIG. 1j into the NaeI/BssHII linearised sequence of FIG. 1h. The DNA sequence of the construct FIG. 1k is SEQ ID NO: 14, while SEQ ID NO: 13 also shows the sequence of the translated peptide. The construct of FIG. 1l is formed by BssHII digest and religation of the sequence of FIG. 1h. The DNA sequence of the construct FIG. 1l is SEQ ID NO: 18, while SEQ ID NO: 17 also shows the sequence of the translated peptide. The construct of FIG. 1m is formed by cloning the AfeI/BssHII fragment of the sequence of FIG. 1i into the AfeI/BssHII linearised sequence of FIG. 1h The DNA sequence of the construct FIG. 1m is SEQ ID NO: 20, while SEQ ID NO:19 also shows the sequence of the translated peptide.

The above constructs may be made by a person skilled in the art using routine techniques.

Example 2

Transfection, Clonal Selection and GLP-1 Expression of Mammalian Cells

Source of the cells: HEK293 (human embryonic kidney cell line, # ACC 305, DSMZ Cell Culture Collection, Germany), AtT20 (Mouse LAF1 pituitary gland tumor cell line, #87021902, European Cell Culture Collection, UK), hTERT-MSC cells are generated by Prof. Kassem, University Hospital of Odense, Denmark.

For transfection of $10^6$ cells 0.5-2 µg plasmid DNA with different constructs was used. The constructs were generated as described in Example 1. HEK293 cells were transfected by standard calcium phosphate co-precipitation method as described in Current Protocols in Molecular Biology (Ausubel et al. 1994ff Harvard Medical School Vol 2., Unit 9.1). AtT20 cells were transfected using FuGene (Roche) as described in current Protocols in Molecular Biology (Ausubel et. al. 1994ff, Harvard Medical School Vol 2., Unit 9.4). Transfection of hTERT-MSC cells was performed using the Nucleofector technology (Amaxa), a non-viral method which is based on the combination of electrical parameters and cell-type specific solutions. Using the Nucleofector device (program C17) and the Nucleofector solution VPE-100I transfection efficiencies >60% have been achieved. 48 hours after transfection selection of cell clones with stable integration of DNA into the chromosome was performed by adding the selective agent blasticidin (2 µg/ml) into the culture medium, 12-15 days later, stable transfected cell clones could be isolated and expanded for characterization.

Figure 2:
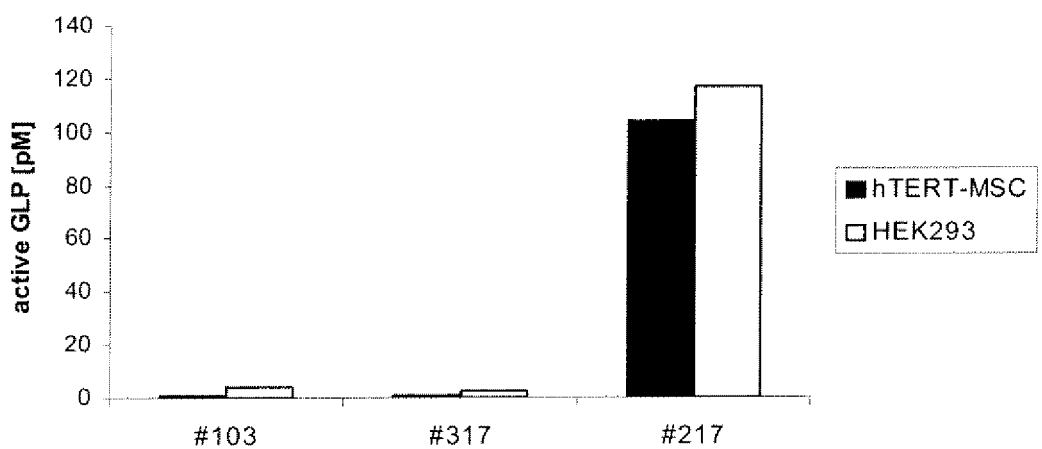
FIG. 2: depicts the results of transient expression of different GLP-1 constructs in hTERT-MSC and HEK293 cells and of active GLP-1 after transient transfection (see also Example 2), Only marginal active GLP-1 level can be found in the monomeric GLP-1 constructs #103 and #317 (having just one copy of GLP-1 (7-37)). An enormous gain in expression was observed in the dimeric GLP-1 construct #217 (having GLP-1 (7-37) as component (I) and as component (III)) both in hTERT-MSC and in HEK293 cells.

Transient expression of different GLP-1 constructs was measured in hTERT-MSC and HEK293 cells. Whereas only marginal active GLP-1 level can be found in the monomeric GLP-1 constructs #103 and #317 (having just one copy of GLP-1 (7-37) an enormous gain in expression can be found in the dimeric GLP-1 construct #217 (having GLP-1 (7-37) as component (I) and as component (III)) both in hTERT-MSC and in HEK293 cells. Results are summarized in FIG. 2. An elongation of the construct to the GLP-1 construct #159 (having lour IP2 copies as component (II) results in no further significant increase (not shown). After transfection of hTERT-MSC cells with different constructs clones were selected, which stably express GLP-1. The expression levels are shown in Table 1.

TABLE 1

| construct | cell clone | active GLP per $10^6$ cells and hour [pmol] |
|---|---|---|
| #103 GLP1$_{(7-37)}$ | 49TM113/13 | 0.4 |
| #317 GLP1$_{(7-37)}$-IP2-11aa | 71TM169/1 | 0.6 |
| #217 GLP1$_{(7-37)}$-IP2-GLP1$_{(7-37)}$ | 79TM217/13 | 2.7 |

Example 3

Western Blot Analysis of GLP-1 Peptides, Secreted from Mammalian Cells

Cell culture supernatant from GLP-1 secreting cells was separated in a 10%-20% gradient SDS PAGE (120V, 90 minutes) and transferred to a PVDF membrane (Immobilon-P Membrane 0.45 µm Millipore IPVH 00010) by semi-dry blotting (2.0 mA/cm2, 60 minutes). After methanol fixation and blocking (3% (w:v) BSA, 0.1% (v:v) Tween-20 in TBS) the membrane was immunoblotted with 1 µg/ml anti-GLP-1 antibody (HYB 147-12, Antibodyshop) at 4° C. o/n, After washing and incubation with 0.02 µg/ml detection antibody (Anti Mouse IgG, HRP conjugated, Perkin Elmer PC 2855-1197) at RT for 4 hours, chemiluminescence detection reveals the location of the protein.

Figure 3:
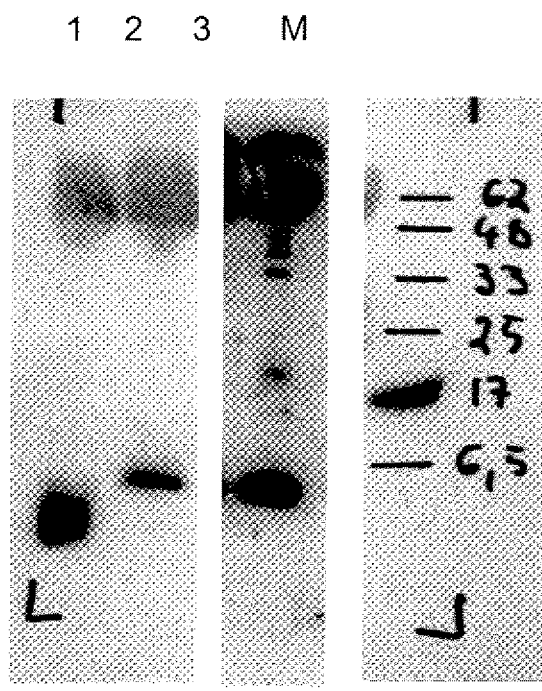

Western Blot Analysis is shown in FIG. 3 (1: 100 ng synthetic GLP-1 (7-37) dissolved in supernatant of mock transfected hTERT-MSC cells, 2: supernatant of hTERT-MSC cells (clone 79TM217/13) secreting dimeric GLP-1 from construct #217, 3: supernatant of AtT20 cells (clone 81-A-217/5) secreting dimeric GLP-1 from construct #217; M: prestained protein marker [kDa]). The results show that peptides containing GLP-1 (7-37) and a C-terminal appendix (2 and 3 in FIG. 3) are secreted from the transfected cell lines and can be detected using an anti-GLP-1 antibody, which binds to the mid-molecular epitopes of GLP-1 (7-37).

Example 4

In Vitro Plasma Stability of GLP-1 Peptides Secreted from Human Cells

HEK293 and hTERT-MSC cells were transiently transfected with constructs, encoding the heterologous stromelysin signal sequence, which is linked to GLP-1 variants encoding the following peptides:
1: GLP-1 (7-37)
2: GLP-1 (7-37)-IP2-extended with 11 AA
3: GLP1 (7-37)-IP2-GLP1 (7-37)

Cell culture supernatant, containing GLP-1 peptides secreted from cells or synthetic GLP-1 (7-37) (Bachem) was incubated with human lymphocyte enriched plasma containing dipeptidylpeptidase activity at 37° C. and 5% $CO_2$, for 3 or 4 hours. Synthetic GLP-1 (7-37) in supernatant from mock transfected cells was used as a positive control for DPP-IV activity, which was shown to be inhibited by addition of an DPP-IV inhibitor (#DPP4, Biotrend). Active GLP was measured using the GLP-1 (Active) ELISA (#EGLP-35K, Biotrend), using an antibody which binds to the N-terminal epitope of GLP-1 (7-37) discriminating the DPP-IV degraded, inactive GLP-1 (9-37) peptide.

Figure 4:
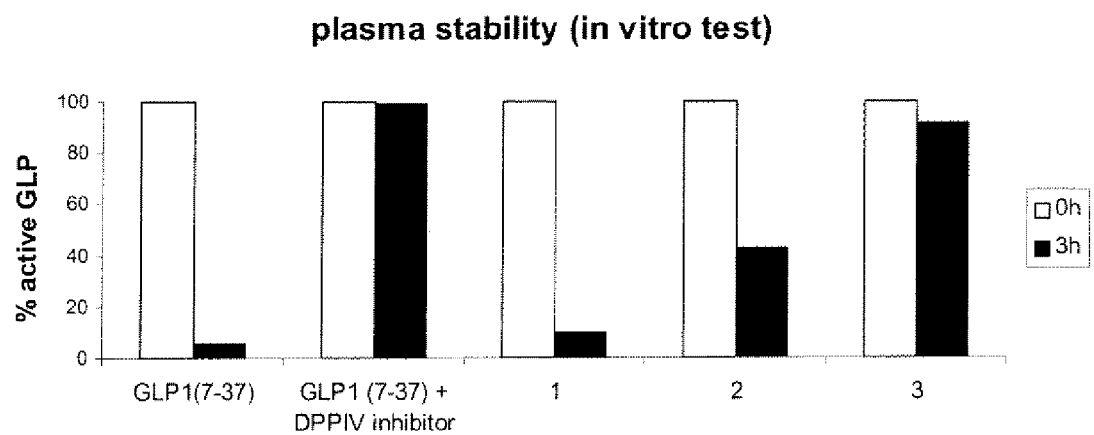
Figure 5:
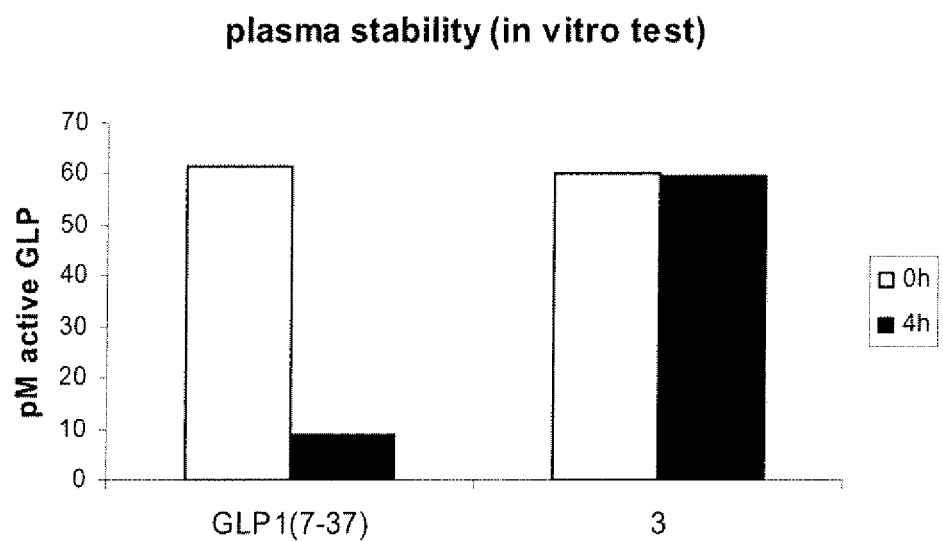
FIG. 5: shows a Western Blot Analysis of a cell culture supernatant from GLP-1 secreting cells (see also Example 3). Lane 1: 100 ng synthetic GLP-1 (7-37) dissolved in supernatant of mock transfected hTERT-MSC cells; Lane 2: supernatant of hTERT-MSC cells (clone 79TM217/13) secreting dimeric GLP-1 from construct #217; Lane 3: supernatant of AtT20 cells (clone 81-A-217/3) secreting dimeric GLP-1 from construct #217; Lane M: prestained protein marker [kDa]). The results show that peptides as defined herein containing GLP-1 (7-37) and a C-terminal appendix (2 and 3 in FIG. 3) are secreted from the transfected cell lines and can be detected using an anti-GLP-1 antibody, which binds to the mid-molecular epitopes of GLP-1 (7-37).

The results are shown in FIGS. 4 (HEK293 cells) and 5 (hTERT-MSC HEK293 and hTERT-MSC cells are both effective hosts for the gene construct. The numbering of the results for the transfected cells of types 1 to 3 is as with Example 3 (1: 100 ng synthetic GLP-1 (7-37) dissolved in supernatant of mock transfected hTERT-MSC cells, 2: supernatant of hTERT-MSC cells (clone 79TM217/13) secreting dimeric GLP-1 from construct #217, 3: supernatant of AtT20 cells (clone 81-A-217/3) secreting dimeric GLP-1 from construct #217). While construct 1 produces wild type GLP-1 which is inactivated by DPP-IV in a similar way to synthetic GLP-1, the C-terminally elongated GLP-1 forms (2 and 3 in FIG. 4, 3 in FIG. 5) are more resistant to degradation and maintain at least 40% activity. The C-terminal extended GLP-1 peptides are significantly stabilized in human plasma in vitro. The peptide with the dimeric GLP-1 sequence (3) is nearly fully stabilized to DPP-IV degradation in vitro.

Example 5

Western Blot Analysis of GLP-1 Peptides

Figure 6:
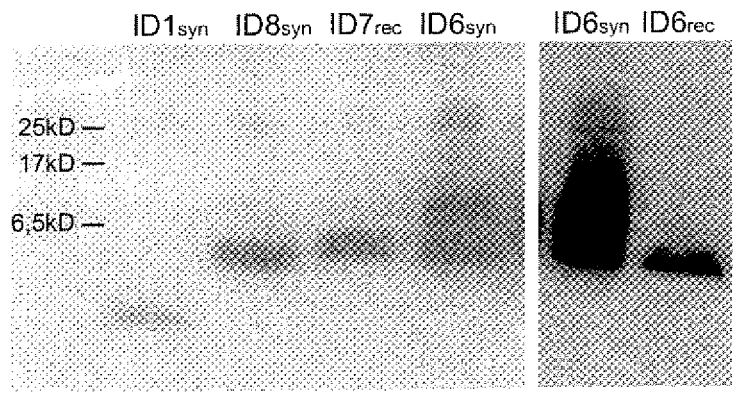
FIG. 6: shows a Western Blot for the peptides indicated below. The following values are given: SEQ ID NO: 1 (ID1syn) corresponds to GLP-1 (7-37), 31 aa, 3.3 kD; SEQ ID NO:8 (ID8 syn, CM3) corresponds to GLP-1 (7-37)-IP2, 46 aa, 5.1 kD; SEQ ID NO: 7 (ID7rec, CM2) corresponds to GLP-1 (7-37)-IP2-RR-GLP2, 83 aa, 9.4kD; SEQ ID NO: 6 (ID6syn, CM1) corresponds to GLP-1 (7-37)-IP2-RR-GLP1 (7-37), 79 aa, 8.7 kD (see also Example 5).

Various GLP-1 peptides were produced synthetically by solid phase (syn) or recombinant using *E. coli* (rec). GLP-1 peptides (31 ng SEQ ID NO:1 and 10 ng of each SEQ ID NO:6, SEQ ID NO:7, SEQ ID NO:8) were separated in a 10%-20% gradient SDS PAGE (120V, 90 minutes) and transferred to a PVDF membrane (Immobilon-P Membran 0.45 µm Millipore IPVH 00010) by semi-dry blotting (2.0 mA/cm², 60 minutes). After methanol fixation and blocking (3% (w:v) BSA, 0.1% v:v) Tween-20 in TBS) the membrane was immunoblotted with 1 µg/ml anti-GLP-1 antibody (HYB 147-12, Antibodyshop) at 4° C. o/n. After washing and incubation with 0.02 μg/ml detection antibody (Anti Mouse IgG, HRP conjugated, Perkin Elmer PC 2855-1197) at RT for 4 hours, chemiluminescence detection reveals the location of the protein. FIG. 6 shows a Western Blot for the peptides indicated. The following values can be given: SEQ ID NO: 1 (ID1syn) corresponds to GLP-1 (7-37), 31 aa, 3.3 kD; SEQ ID NO:8 (ID8 syn, CM3) corresponds to GLP-1 (7-37)-IP2, 46 aa, 5.1 kD; SEQ ID NO: 7 (ID7rec, CM2) corresponds to GLP-1 (7-37)-IP2-RR-GLP2, 83 aa, 9.4 kD; SEQ ID NO: 6 (ID6syn, CM1) corresponds to GLP-1 (7-37)-IP2-RR-GLP1 (7-37), 79 aa, 8.7 kD.

Example 6

In Vitro Human Plasma Stability of GLP-1 Cm Peptides

Synthetic GLP-1 peptides (SEQ ID NO:$1_{syn}$, SEQ ID NO:$6_{syn}$, SEQ ID NO:$7_{rec}$, SEQ ID NO:$8_{syn}$) were incubated at concentrations of 20 ng/ml with human plasma at 37° C. and 5% $CO_2$ for 3 hours. Dipeptidylpeptidase activity of the plasma was inhibited by an DPP-IV inhibitor (#DPP4, Biotrend), Active MT was measured using the GLP-1 (Active) ELISA (#EGLP-35K, Biotrend).

Figure 7:
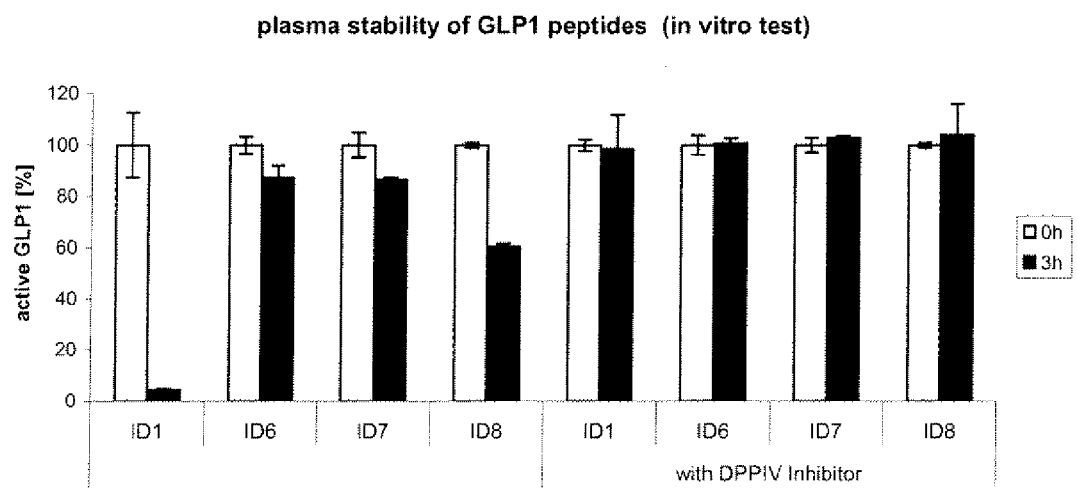
FIG. 7: illustrates plasma stability tests of GLP-1 peptides in vitro. In contrast to the native GLP-1$_{(7-37)}$ (SEQ ID NO: 1) the C-terminal elongated GLP-1 peptides SEQ ID NO: 6, SEQ ID NO: 7, and SEQ ID NO: 8 are significantly stabilized in human plasma in vitro. As control (on the right hand side) the results obtained for experiments with addition of DPP-IV inhibitor are shown. GLP-1 activity is completely maintained in these control experiments (see also Example 6).

In contrast to the native GLP-$1_{(7-37)}$ (SEQ ID NO:1) the C-terminal elongated GLP-1 peptides SEQ ID NO:6, SEQ ID NO:7, and SEQ ID NO:8 are significantly stabilized in human plasma in vitro (FIG. 7). As control (on the right hand side) the results obtained for experiments with addition of DPP-IV inhibitor are shown. GLP-1 activity is completely maintained in these control experiments.

Example 7

Bioassay In Vitro
Cyclic AMP Production

RIN-5F cells (rat islet cell tumor; ECACC No. 95090402) were grown in 24-well plates for 4 days; reaching 70% confluence, Cells were washed twice with DMEM (E15-009, PAA) before addition of 0.5 ml DMEM (E15-009, PAA) supplemented with 1% HSA (Aventis). 0.2 mM IBMX (858455, Sigma) and the test peptides. After a 20 minute incubation at 25° C., cells were washed twice with ice cold PBS. Cellular cAMP was extracted by addition of 0.1N HCl containing 0.5% Triton X-100. Cyclic AMP was quantified using the cAMP (low pH) EIA (Cat. DE0355, R&D). For stimulation $3*10^{-8}$ M SEQ ID NO:1, SEQ ID NO:$6_{syn}$, SEQ ID NO:$6_{rec}$, SEQ ID NO:$7_{rec}$, SEQ ID NO: $8_{syn}$, have been used.

Figure 8:
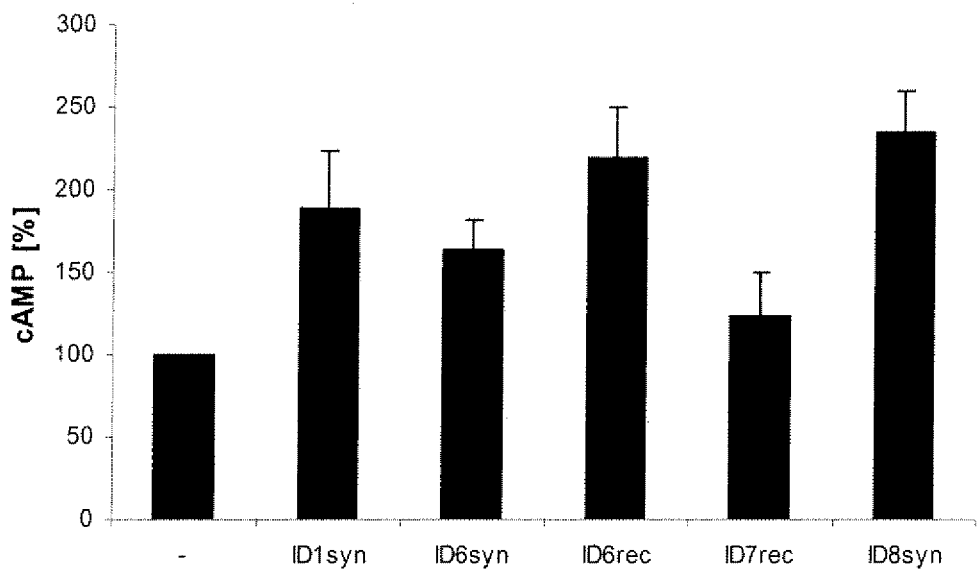
FIG. 8: shows the results for an in vitro bioassay with cyclic AMP (cAMP) Production: as can be seen from FIG. 8, 100% cAMP production corresponds to the basal production in the absence of GLP-1. GLP-1 binds to G protein-coupled receptors and stimulates cAMP production. All GLP-1 molecules tested (ID1syn, ID6syn, ID6rec, ID7rec, ID8syn) increase the cellular cAMP production (see also Example 7).

Results are shown in FIG. 8. 100% cAMP production corresponds to the basal production in the absence of GLP-1. GLP-1 hinds to G protein-coupled receptors and stimulates cAMP production. All molecules tested increase the cellular cAMP production.

Example 8

In Vivo Bioactivity 11-week-old type II diabetic mice (C57BL/Ks-Lepr$^{db/db}$, Harlan) were treated with 5 μg peptide by subcutaneous injection twice a day at 9 a.m. and 5 p.m. (n=5 per group), Blood glucose was measured before (day 0) and after treatment with GLP$^{CM}$ peptides (Day 2, 4, 7, 10) at 10 a.m. after an overnight fastening period. Data were presented in relation to blood glucose levels measured at day 0.

Figure 9:
FIG. 9: illustrates the results for in vivo bioactivity tests with GLP-1 constructs as defined herein with 11-week-old type II diabetic mice (C57BL/Ks-Lepr$^{db/db}$, Harlan). All GLP-1 peptides tested (SEQ ID NO: 6 (synthetic or recombinant) and SE ID NO: 7 (synthetic or recombinant)) have an anti-hyperglycemia effect. Best results were obtained with recombinant SEQ ID NO: 6 (CM1) and synthetic SEQ ID NO: 8 (CM3) (see also Example 8).

All GLP-1 peptides tested (SEQ ID NO:6 (synthetic or recombinant) and SEQ ID NO:7 (synthetic or recombinant) have an anti-hyperglycemia effect. Best results were obtained with recombinant SEQ ID NO:6 (CM1) and synthetic SEQ ID NO:8 (CM3). In FIG. 9 (y-axis) the relative effect of the treatment is shown, Blood glucose at day=0 was set to 1. Untreated animals undergo continuous increase in blood glucose level over time, whereas animals treated with GLP-1 peptides as defined herein display grosso modo a continuous decrease of the blood glucose level over time.

Example 9

Plasma Creation

The vector for transient and stable gene expression consists of two separate transcription units, one for the gene of interest (GOI) and one for the fusion of the suicide gene HSV thymidine kinase and the resistance gene blasticidin. For the first transcription unit, the human ubiquitin B promoter was used, and for the second transcription unit the human ferritin promoter was used The plasmid is based on plasmid pCM+, having 7,919 base pairs, shown schematically in FIG. 10.

Figure 10:
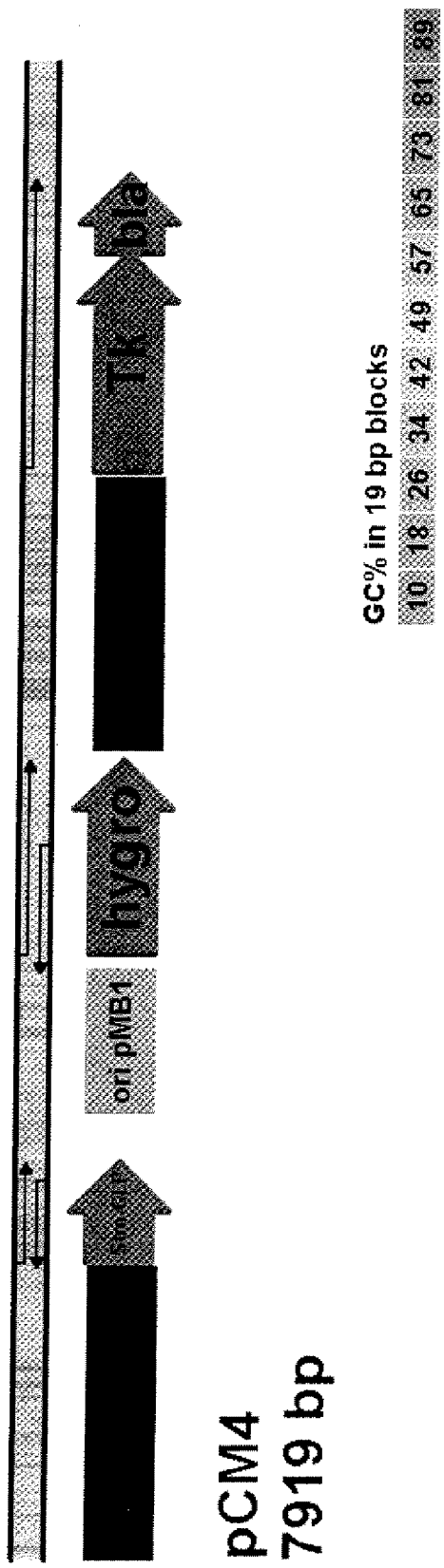
FIG. 10: depicts an exemplary vector used for transient and stable gene expression. The vector consists of two separate transcription units, one for the gene of interest (GOI) and one for the fusion of the suicide gene HSV thymidine kinase and the resistance gene blasticidin. For the first transcription unit, the human ubiquitin B promoter was used, and for the second transcription unit the human ferritin promoter was used (see also Example 9)

As shown in FIG. 10, transcription unit 1, comprises the following components:

| | |
|---|---|
| CMVenh: | immediate early enhancer human cytomegalovirus |
| ubiB human: | ubiquitin promoter B |
| Stro-GLP: | fusion gene, coding for signal peptide and leader sequence of stromelysin and GLPI constructs |
| ori pMBI: | E coli minimal origin of replication. |
| Hygro: | hygromycin B resistance gene. |
| | Transcription unit 2. |
| SV 40 enh: | SV40 enhancer. |
| FerH: | Human ferritin H promoter combined with 5'UTR of the murine EFI gene. |
| Tk-bla: | fusion gene coding for herpes simplex virus type 1 thymidine kinase and blasticidine resistance gene. |

For transient expression the circular plasmid was used. For the selection of stable expressing cell clones, the plasmid was linearised and bacterial sequences (pMB1 origin and hygromycin gene) eliminated.

Example 10

Production of Mesenmchymal Stem Cell Line.

The mesenchymal stein cell line was generated by Prof. Kassem, University Hospital of Odense, Denmark (published in Simonsen et al., 2002, Nature Biotechnology 20 m, 592-596) according to following criteria:
Origin The production cell line consists of mesenchymal stem cells (MSC), isolated from bone marrow aspirates of a healthy male donor (age 33).
Immortalisation Cells were immortalized by introduction of the coding sequence of the telomerase reverse transcriptase. Retroviral transduction was performed by packaging the GCsam retroviral vector in which the expression of the transgene is driven by the Moloney murine leukemia virus long terminal repeat in PG13. Transduction was performed on day 9 (PDL 12) of culture. The cell line has so far been cultivated until population doubling level (PDL) of 260.

The insertion locus was tested by fluorescence in situ hybridization and southern blot. There is only one insertion locus of ecotopic hTERT on chromosome 5 (5q13-31). Analysis was performed at PDL 186. Giemsa banding and comparative genomic hybridization revealed that hMSC-TERT did not develop any numerical or structural chromosomal abnormalities at PDL 96 and maintained a normal diploid male karyotype. Tumorigenity was tested in immunodeficient mice after subcutaneous implantation for six months and was found negative for PDL 80.

Flow Cytometry (FACS) Analysis

Cells were cultured in standard growth medium to 80% confluence. Cells were trypsinised and assayed for size and granularity by FACScan flow cytometer (Becton-Dickinson). For surface marker studies trypsinised cells were stained with antibodies directly conjugated to a fluorescent dye (FITC-conjugated mouse anti human CD44 monoclonal antibody, #CBL154F, Cymbus Biotechnology; phycoerythrin-conjugated mouse anti human CD166 monoclonal antibody, #559263, BD Pharmingen) for 30 min on ice. Samples were washed and fixed with 1% of paraformaldehyde until analysis with FACScan (Becton-Dickinson).

Characterization

Figure 11:
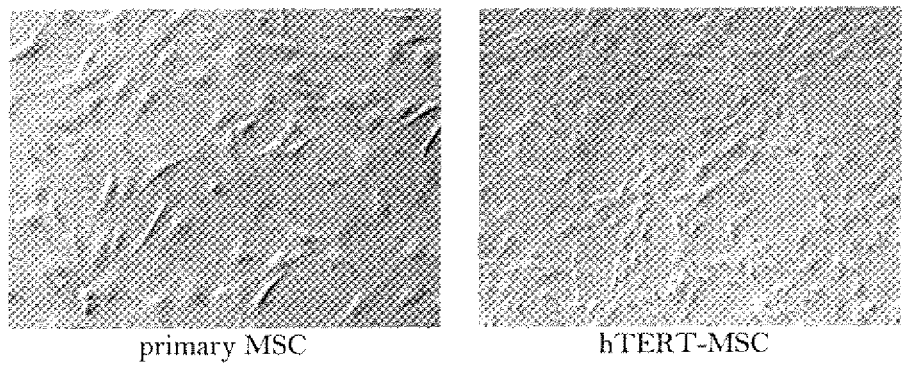
FIGS. 11, 12: illustrates characterization of cells used for inventive spherical microcapsules after immortalizing the cells in advance. As may be seen from FIG. 11, immortalized cells are still able to differentiate into adipocytes, osteocytes and chondrocytes as their non-immortalized counterparts (see FIG. 11). Immortalized cells have fibroblastic morphology and are more homogeneous regarding size and granularity as the mortal MSCs as shown by flow cytometry e.g. using CD 44 and CD166 epitope markers which are characteristic for the primary cells used here. Immortalized cells express the same CD markers as their non immortalized counterparts (see FIG. 12).
Figure 12:
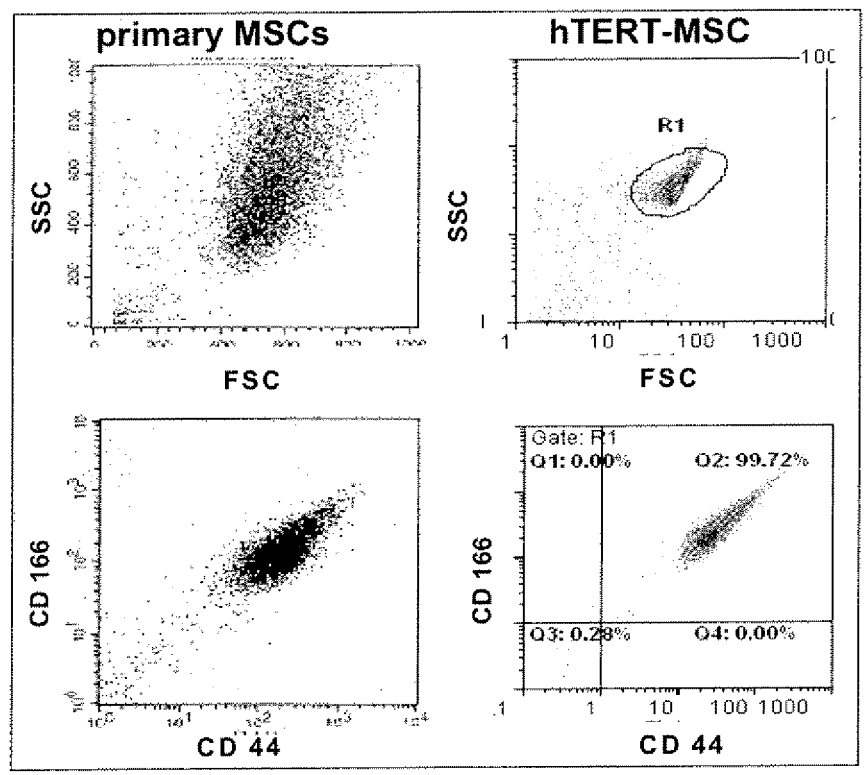

Immortalized cells are still able to differentiate into adipocytes, osteocytes and chondrocytes as their non-immortalized counterparts (see FIG. 11). Immortalized cells have fibroblastic morphology and are more homogeneous regarding size and granularity as the mortal MSCs as shown by flow cytometry e.g. using CD 44 and CD166 epitope markers which are characteristic of the primary cells used here. Immortalized cells express the same CD markers as their non immortalized counterparts (see FIG. 12).

Cultivation

| Serum containing medium: | 7% Earles MEM |
| --- | --- |
| | 10% FCS |
| | 2 mM L-Glutamine |
| | 1 mM Sodiumpyruvate |
| | 100 U/ml Penicilline |
| | 0.1 mg/ml Streptomycin |

The population doubling is between 26 and 30 hours.

Transfection and Clonal Selection

For transfection of $10^6$ cells 0.5-2 µg plasmid DNA with different GLP1 constructs was used. HEK293 cells were transfected by standard calcium phosphate co-precipitation method. AtT20 cells were transfected using FuGene (Roche).

Transfection of hTERT-MSC cells was performed using the Nucleofector technology (amaxa), a non-viral method which is based on the combination of electrical parameters and cell-type specific solutions. Using the Nucleofector device (program C17) and the Nucleofector solution VPE-1001 transfection efficiencies >60% have been achieved.

48 hours after transfection selection of cell clones with stable integration of DNA into the chromosome was performed by adding the selective agent blasticidin (2 µg/ml) into the culture medium. 12-15 days later, stable transfected cell clones could be isolated and expanded for characterization.

Expression

Transient expression of different GLP constructs was measured in hTERT-MSC and HEK293 cells. An active GLP1 level can be found in the monomeric GLP1 constructs #103 (Stro-GLP1$_{(7-37)}$) and #317 (Stro-GLP1$_{7-37}$-IP2-extended with 11aa) and an enormous gain in expression can be found in the dimeric GLP1 construct #217 (Stro-GLP1$_{7-37}$-IP2-GLP1$_{7-37}$) both in hTERT-MSC and in HEK293 cells. An elongation of construct #317 to the tetrameric GLP1 construct #159 (Stro-GLP1$_{(7-37)}$-IP2 (4x)-11aa) results in an similar activity (see also above FIG. 2). After transfection of hTERT-MSC cells with different constructs clones were selected, which stably express GLP1 (see above FIGS. 4 and 5, Example 4)

Example 11

Encapsulation

The cultivated cells to be encapsulated ere washed with PBS (PAA, Austria) and separated using trypsin/EDTA (PAA, Austria). The reaction was quickly stopped using medium (dependent on cell type, for example RPMI, PAA, Austria and the cell suspension centrifuged off (8 min at 1,200 rpm) The pellet was resuspended in PBS and the cell count determined. The desired quantity of $1.4\times10^7$ cells was centrifuged off again (8 min at 1,200 rpm). The PBS was then completely removed by suction and 60 µl pellet was resuspended without air bubbles in 80 µl PBS. This cell suspension was taken up in 560 µl of 0.8% (w/v) potassium alginate solution (an alginate with a viscosity of approximately 40 mPa·s of at 0.1% (w/v) aqueous solution at room temperature was used).

To mix the resuspended cells with the alginate solution, the solution was drawn up in a 1 ml syringe with cannulas and homogeneously mixed with the cells by way of repeated slow drawing up and drawing off. A cell concentration of $2\times10^7$ cells/ml resulted. A quantity of $2\times10^7$ cells/ml may be obtained accordingly.

For producing the microcapsules with a diameter of about 400 µm, a cannula with an internal diameter of 400 µm was used in an air-charged three-channel spray nozzle for the inner channel. The cannula was fixed in an outer nozzle with an internal diameter of 700 µm. An air ring with an opening of 1.5 mm was screwed over the two inner cannulas. The device is an adapted version of the device described in WO 00/09566. The homogeneous cell/alginate solution mixture was dripped through the described spray nozzle. For this purpose, the 1 ml syringe containing the mixture was placed on the inner channel by means of a luer connector. The cell/alginate solution mixture was pressed through the inner channel at a speed of 300 µl/min. The airflow was conveyed though the outer air ring at a speed of 2.5 l/min. The resulting microcapsules precipitated into a barium-containing precipitation bath (20 mM BaCI, 5 mM L-histidine, 124 mM NaCl, pH 7.0±0.1, 290 mOsmol±3) which was constructed approximately 10 cm below the spray nozzle. After a dwell time of 5 min in the barium-containing precipitation bath the microcapsules were washed five times with 20 ml PBS in each case.

500 µl of the single-layer microcapsules were then taken up in 500 µl of a 0.8 (w/v) alginate solution the same as used for the core, above and homogeneously mixed. This suspension was taken up in a 1 ml syringe and connected by means of a leer connector to the inner channel (internal diameter: 400 µm) of the spray nozzle and pressed at a speed of 50 µl/min therethrough. A 5 ml syringe with a 0.8% alginate solution was connected by means of a luer connector to the second inner channel (internal diameter: 700 µm) and pressed there through at a speed of 250 µl/min. The airflow was conveyed through the outer air ring at a speed of 2.9 l/min. The resultant microcapsules precipitated into a barium-containing precipitation bath (20 mM BaCI, 5 mM L-histidine, 124 mM NaCl, pH 7.0 I 0.1, 290 mOsmol±3) which is constructed approximately 10 cm below the spray nozzle. After a dwell time of 5 min in the barium-containing precipitation bath, the microcapsules were washed four times with 20 ml PBS in each case and once with medium. Two-layer microcapsules with a total diameter of approximately 600 µm±100 µm (including the alginate layer) were produced by this process, wherein the diameter of the inner, cell containing core is 380 µm±20 µm. The concentration of cell in the core is about $2-3\times10^7$ cell/ml alginate. This results in inventive spherical microcapsules (CellBeads) with a bead volume of 0.065-0.180 µl containing approximately 1000 cells per bead. A CellBead with GLP-1 secreting cells produces on average 5 fmol active GLP per hour.

After encapsulation inventive spherical microcapsules (CellBeads) can be cultured in an foetal calf Serum (FCS) free culture media (LP02 with 10% Lipumin) produced according to GMP guidelines for at least six days without any decline in viability.

For implantation into fat tissue, the encapsulated hTERT-MSC cells were differentiated to adipocytes (see Example 12).

Example 12

Differentiation into Adipocytes (Bead)

Differentiation of mesenchymal stem cells into adipocytes by MEM based media which include insulin, dexamethasone and isobutyl xanthine has been described by Gimble at al. (1995, J. Cell Biochem. 58, 393-402) and Simonsen et al. (op cit.). In these experiments the differentiation process into adipocytes is performed in animal component free culture media. The differentiation process takes two weeks and yields >90% of adipocytes. Components typically used for animal component free culture media are as follows: DMEM/HAM's F12, HEPES, Hydrocortisone, Insulin, Triidothyronine, Biotin, DL-Pantothenic Acid Hemicalcium, Troglitazone, Octanoic acid (CA), Dexamethasone, an animal component free lipid mixture, Isobutyl methyl xanthinine.

The accumulation of intracellular triglycerides, which is a marker of adipocyte differentiation (Greenberger JS. Corticosteroid-dependent differentiation of human marrow preadipocytes in vitro. In vitro. 1979 October, 15(10):823-8) can be monitored by the dye AdipoRed, which is a solution of the hydrophilic stain Nile Red (Greenspan P, Mayer E P, Fowler S D. Nile red: a selective fluorescent stain for intracellular lipid droplets. J. Cell Biol. 1985 March, 100(3):965-73). The monitoring was carried out according to the instruction manual AdipoRed Assay Reagent (#PT-7009, Cambrex).

Glycerol-3-phosphate dehyrdogenase (GPDH) is highly expressed in mature adipocytes (Sottile V, Seuwen K. A high-capacity screen for adipogenic differentiation. Anal. Biochem. 2001 Jun. 1; 293(1):124-8). The activity of this enzyme was measured to assess adipogenic differentiation of the cells according to the instruction manual Glycerol-3-phosphate dehydrogenase (GPDH) activity assay kit (#MK426, Takara).

FABP4/aP2 is an intracellular lipid binding protein which is expressed specifically in mature adipocytes (Graves R A, Tontonoz P, Platt K A, Ross S R, Spiegelman B M. Identification of a fat cell enhancer: analysis of requirements for adipose tissue-specific gene expression. J Cell Biochem, 1992 July, 49(3):219-24). FABP4 positive cells can therefore be classified as mature adipocytes. After methanol fixation and blocking, immunostaining was carried out with rabbit anti-FABP4 polyclonal antibody (#100044944, IBL, Hamburg) and Cy-3-conjugated anti-rabbit IgG (#111-166-006 Dianova). The viability of differentiated adipocytes is similar to undifferentiated cells. However the proliferation which is observed in undifferentiated inventive spherical microcapsule (CellBeads) cultures does not take place in differentiated inventive spherical microcapsule (CellBeads) cultures.

Example 13

Western Blot Analysis of GLP-1

Figure 13:
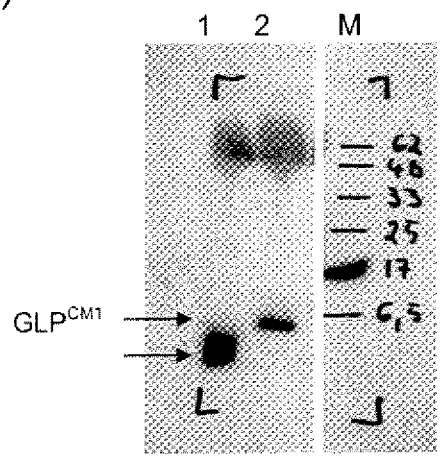
FIGS. 13, 14, 15: show a Western Blot Analysis of GLP-1 secretion with different cell types (hTERT-MSC cells.
Figure 13:
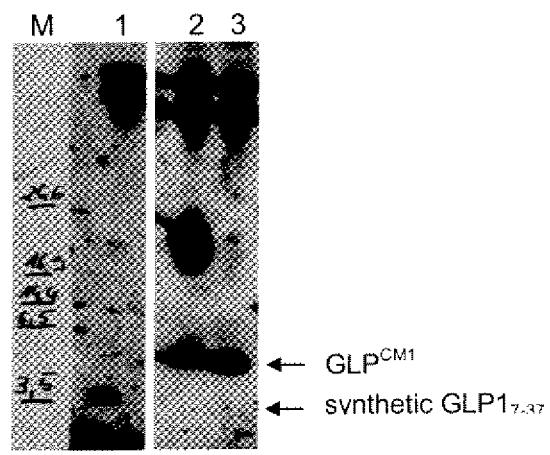
Figure 14:
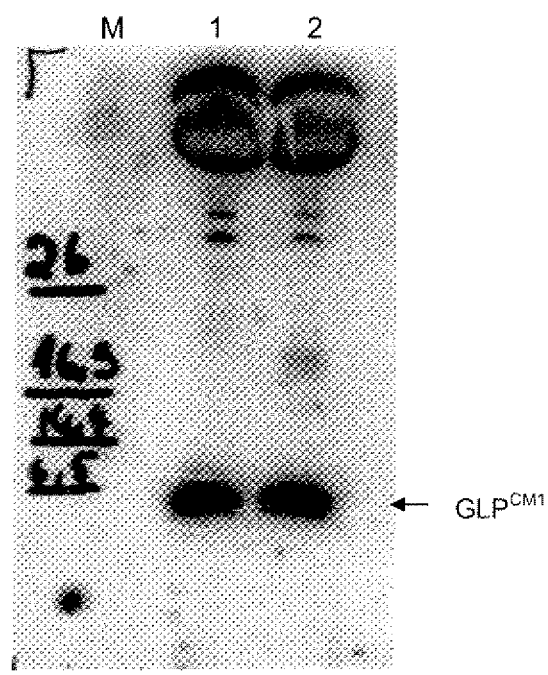
Figure 15:
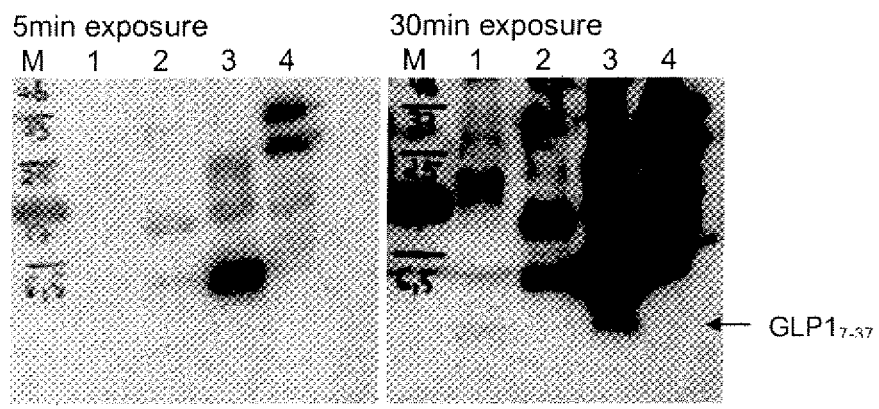

The encapsulated differentiated transfected adipocytes or other cell types are grown in a medium (see above). Cell culture supernatant was separated in a 10%-20% gradient SDS PAGE (120 V, 90 minutes) and transferred to a PVDF membrane (Immobilon-P Membran 0.45 µm Millipore IPVH 00010) by semi-dry blotting (2.0 mA/cm$^2$, 60 minutes). After methanol fixation and blocking (3% (w/v) BSA, 0.1% (v/v) Tween-20 in TBS) the membrane was immunoblotted with 1 pg/ml anti-GLP1 antibody (HYB 147-12, Antibodyshop) at 4° C. o/n. After washing and incubation with 0.02 µg/ml detection antibody (Anti Mouse IgG, HRP conjugated, Perkin Elmer PC 2855-1197) at room temperature for 4 hours, chemiluminescence detection reveals the location of the protein. The results are shown in FIGS. 13, 14 and 15 which indicate the cell type (hTERT-MSC, AtT20 or HEK293 cells) and the clone number. The results show that the constructs of GLP-1/C, terminal peptide are secreted from the transfected cell lines, i.e. the protein has the expected molecular weight. Additionally, it binds to anti-GLP-1 antibody which binds to the N terminal end of GLP-1 (7-37).

Example 14

Immunoprecipitation of the Peptide

For immunoprecipitation of the GLP1$^{CM}$ peptides, culture supernatant was preincubated o/n at 4° C. with Protein-G-Agarose (20 µl Agarose/ml supernatant). Unspecific bound protein was eliminated by a filtration through a 0.2 µm filter. After incubation with 1 µg/ml Anti-GLP1 capture antibody (HYB 147-12, Antibodyshop) for 12 h at 4° C., Protein-G Agarose was added for 2 h at RT. Precipitation was done by centrifugation followed by repeated washing steps with PBS. The immunoprecipitate was boiled in Lämmli Loading buffer, separated on a 10%-20% SDS PAGE gel and immunobloted as described.

Figure 16:
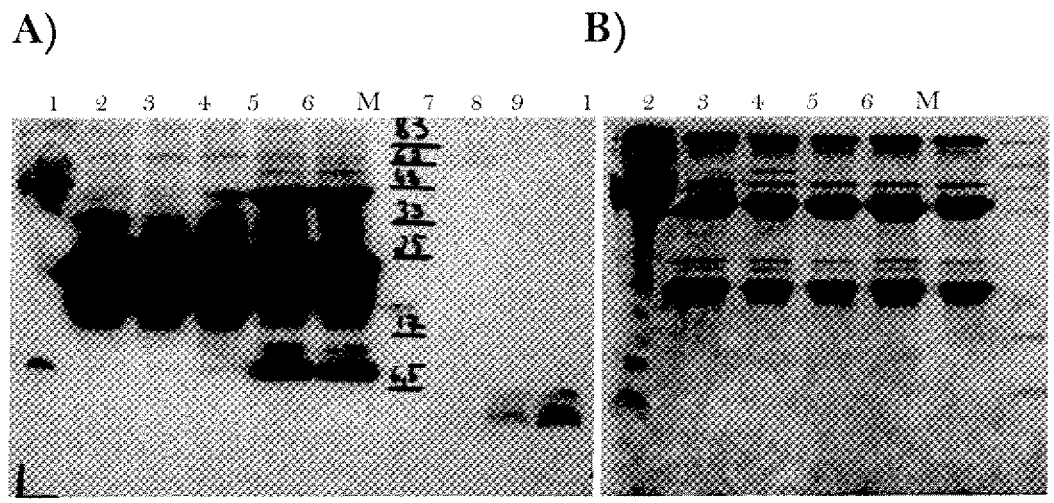
FIG. 16: shows an immunoprecipitation of GLP1$^{CM}$ peptides. Immunoprecipitation of GLP$^{CM1}$ peptide from cell culture supernatant by using Anti-GLP1 capture antibody HYB 147-12 or HYB 147-12 (Antibodyshop) leads to resulting in accumulation op the GLP$^{CM1}$ peptide and elimination of cross-contaminating proteins. 1: supernatant of GLP$^{CM1}$ secreting hTERT-MSC cells (clone 79TM217/13), 2: Immunoprecipitation with Protein G but without GLP1 antibody, 3: Immunoprecipitation with Protein G and GLP1 antibody sc-7782 (Santa Cruz), 4: Immunoprecipitation with Protein G and GLP1 antibody sc-26637 (Santa Cruz), 5: Immunoprecipitation with Protein G and GLP1 antibody HYB147-12 (Antibodyshop), 6: Immunoprecipitation with Protein G and GLP1 antibody HYB147-08 (Antibodyshop), 7: 10 ng synthetic GLP1$_{7-37}$, 8: 31 ng synthetic GLP1$_{7-37}$, 9: 100 ng synthetic GLP1$_{7-37}$, Immunoprecipitation with the GLP1, antibody's HYB147-08 and HYB147-12 results in an accumulation of the GLP$^{CM1}$ peptide, thereby eliminating cross-contaminating proteins in the supernatant (see lane 1 Coomassie stain).

Immunoprecipitation of the GLP$^{CM1}$ peptide from cell culture supernatant can be performed by using the Anti-GLP1 capture antibody HYB 147-12 or HYB 147-12 (Antibodyshop) resulting in accumulation op the GLP$^{CM1}$ peptide and elimination of cross-contaminating proteins. The results are shown in FIGS. 16 A and B.

Example 15

Figure 17:
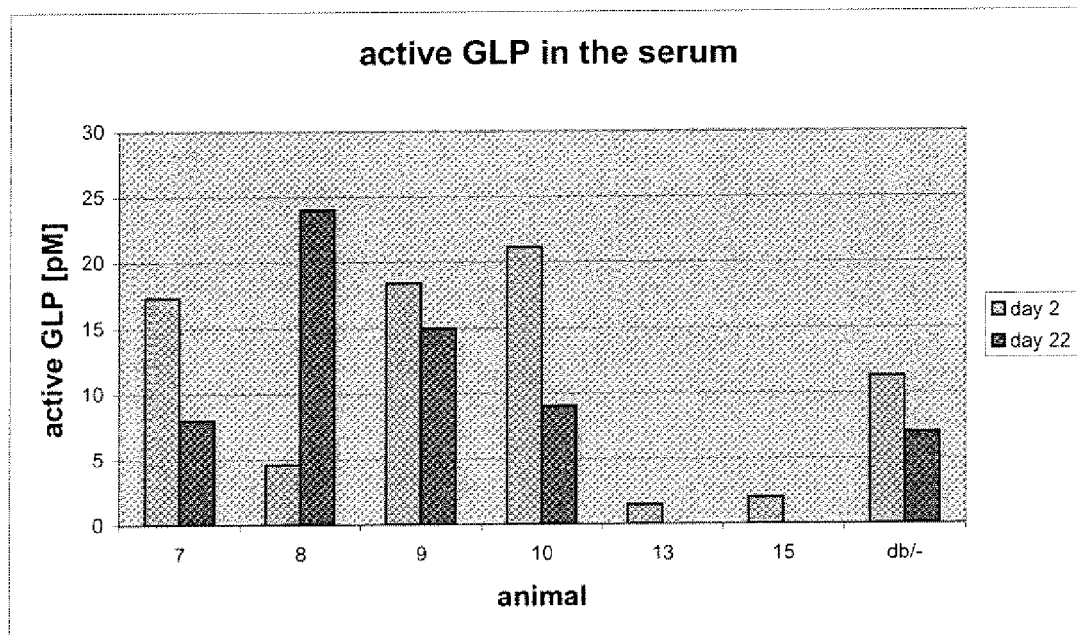
FIG. 17: illustrates an animal trial with inventive spherical microcapsules (CellBeads) in db/db mice. The mouse model used was type II diabetic mice C57/KS-RJ db/db (recessive mutation in the leptin receptor) with implanted murine GLP/CM1 (SEQ ID NO: 6) secreting CellBeads. The GLP secreting cell line was AtT20. Active GLP was measured in the serum of diabetic mice at day 2 and day 22 after implantation of inventive spherical microcapsules (CellBeads) using the GLP-1 (Active) ELISA (#EGLP-35K, Biotrend): The columns represent.

Animal Trial: Testing of Inventive Spherical Microcapsules (CellBeads) in dbldb Mice The mouse model used herein was type II diabetic mice C57/Ks-RJ db/db (recessive mutation in the leptin receptor). For animal trials murine GLP/CM1 (SEQ ID NO: 6) secreting inventive spherical microcapsules (CellBeads) was implanted into 12 week old C57/KS-RJ db mice. The GLP secreting cell line was AtT20, a murine pituitary gland tumour cell line transfected as above. Inventive spherical microcapsules (CellBeads) were injected through a 19 G needle. Different implantation sites (muscle, fat) and implantation volumes (10 µl, 100 µl) have been tested. Active GLP was measured in the serum of diabetic mice at day 2 and day 22 after implantation of inventive spherical microcapsules (CellBeads) using the GLP-1 (Active) ELISA (#EGLP-35K. Biotrend). As a read out for the efficacy the blood glucose level of the fasted animals were measured and IPGTTs (i.p. glucose tolerance tests: i.p. injection of glucose in an overnight fasted mice followed by measurement of blood glucose in the following 2 h) were done. Active GLP-1 was found in the Serum of transplanted animals at a mean concentration of 15 pM at day 2 and 14 pM at day 22 after transplantation of inventive spherical microcapsules (CellBeads) secreting wildtype GLP1CM1 (n=4) (see FIG. 17).

A significant normalization of the fasted glucose levels in diabetic mice can be achieved by implantation of inventive spherical microcapsules (CellBeads) secreting wildtype GLP1CM1 (SEQ ID NO: 6) or the analog GLP1CM1(G8) (SEQ ID NO: 6 but with the second residue substituted by G) in both muscle (hind leg) and fat (neck fat pad) (FIGS. 18 and 19). Also the IPGTT results (FIG. 20) confirmed efficacy in glucose metabolization in that the glucose level at the point of injection (t=O) is about the same as normal mice (contrasted with elevated levels for diabetic mice). Also, although the level rises more in the treated mice than normal mice, this level returns to normal relatively quickly.

The invention claimed is:

1. A spherical or non-spherical microcapsule comprising at least one surface coating and one core, wherein the at least one surface coating comprises cross-linked polymers, and wherein the core comprises cross-linked polymers and cells capable of expressing and secreting a fusion peptide comprising SEQ ID NO: 10 or a peptide having an identity of at least 95% with SEQ ID NO: 10 or SEQ ID NO: 6 or a peptide having an identity of at least 95% with SEQ ID NO: 6, and wherein the cells contained in the core of the spherical microcapsule are selected from human mesenchymal stem cells, differentiated cells derived from human mesenchymal stem cells, including osteoblasts, chondrocytes, fat cells (adipocytes), or neuron-like cells including brain cells.

2. The spherical or non-spherical microcapsule according to claim 1, wherein the cross-linked polymer of the core and/or the at least one surface coating comprises biopolymers.

3. The spherical or non-spherical microcapsule according to claim 1, wherein the cross-linked polymer of the core and/or the at least one surface coating comprises an alginate.

4. The spherical or non-spherical microcapsule according to claim 1, wherein the cross-linked polymer of the core and/or the at least one surface coating comprises a chemically identical polymer in identical or differing concentrations, wherein the polymers further may have different molecular weights and/or may he cross-linked differently.

5. The spherical or non-spherical microcapsule according to claim 1, wherein the core has a diameter of about 20 to about 2000 µm and wherein the at least one surface coating has a thickness of about 10 to about 2000 µm.

6. The spherical or non-spherical microcapsule according to claim 1, wherein the microcapsule comprises 1, 2, 3, 4, 5, 6, 7, 8, 9, 10 or more surface coatings.

7. The spherical or non-spherical microcapsule according to claim 1, wherein the microcapsule comprises an additional external surface coating consisting of polycations.

8. The spherical or non-spherical microcapsule according to claim 7, wherein the additional external surface coating consists of Poly-L-Lysine.

9. The spherical or non-spherical microcapsule according to claim 1, wherein the cells contained in the core of the spherical microcapsule are selected (in vitro) from human mesenchymal stem cells, wherein the cells differentiate in vitro or in vivo into fat cells (adipocytes), suitable for transplantation into fat tissue.

10. A phaanaceutical composition comprising a spherical or non-spherical microcapsule according to claim 1 and optionally a pharmaceutically acceptable carrier.

11. The spherical or non-spherical microcapsule according to claim 1, secreting a fusion peptide consisting of SEQ ID NO: 10 and SED ID NO: 6 or a peptide having an identity of at least 95% with SEQ ID NO: 10 or SEQ ID NO: 6.

* * * * *